(12) United States Patent
Hührlimann et al.

(10) Patent No.: US 11,905,517 B2
(45) Date of Patent: Feb. 20, 2024

(54) **OPTIMIZED HOST/VECTOR SYSTEM FOR PRODUCING PROTECTIVE MONO- AND MULTIVALENT SUBUNIT VACCINES ON THE BASIS OF THE YEAST *KLUYVEROMYCES LACTIS***

(71) Applicant: VEROVACCINES GMBH, Halle/Saale (DE)

(72) Inventors: Hans Caspar Hührlimann, Leipzig (DE); Martina Behrens, Halle (DE); Mandy Gebauer, Schwerin (DE); Karin Breunig, Berlin (DE); Sven-Erik Behrens, Halle (DE)

(73) Assignee: VEROVACCINES GMBH, Halle/Saale (DE)

( * ) Notice: Subject to any disclaimer, the term of this patent is extended or adjusted under 35 U.S.C. 154(b) by 372 days.

(21) Appl. No.: 16/958,170

(22) PCT Filed: Dec. 19, 2018

(86) PCT No.: PCT/DE2018/000379
§ 371 (c)(1),
(2) Date: Jun. 26, 2020

(87) PCT Pub. No.: WO2019/129321
PCT Pub. Date: Jan. 4, 2019

(65) Prior Publication Data
US 2021/0230612 A1 Jul. 29, 2021

(30) Foreign Application Priority Data

Dec. 27, 2017 (DE) ...................... 10 2017 012 109.5

(51) Int. Cl.
*A61P 31/14* (2006.01)
*A61P 31/16* (2006.01)
*A61K 39/12* (2006.01)
*A61K 39/145* (2006.01)
*C12N 15/81* (2006.01)
*A61K 9/00* (2006.01)
*C12N 1/16* (2006.01)
*A61K 39/00* (2006.01)

(52) U.S. Cl.
CPC .......... *C12N 15/815* (2013.01); *A61K 9/006* (2013.01); *A61K 9/0019* (2013.01); *A61K 39/12* (2013.01); *A61K 39/145* (2013.01); *A61P 31/14* (2018.01); *A61P 31/16* (2018.01); *C12N 1/16* (2013.01); *A61K 2039/523* (2013.01); *A61K 2039/54* (2013.01); *A61K 2039/542* (2013.01); *A61K 2039/552* (2013.01); *A61K 2039/70* (2013.01); *C12N 2720/10034* (2013.01); *C12N 2760/16134* (2013.01); *C12N 2770/24334* (2013.01)

(58) Field of Classification Search
None
See application file for complete search history.

(56) References Cited

U.S. PATENT DOCUMENTS

2015/0190486 A1* 7/2015 Breunig ............... C07K 14/005
435/254.2

FOREIGN PATENT DOCUMENTS

WO 2010/054649 5/2010
WO 2013/107436 7/2013

OTHER PUBLICATIONS

Jorrit-Jan Krijger et al. "A novel, lactase-based selection and strain improvement strategy for recombinant protein expression in Kluyveromyces lactis, art 112" Microbial Cell Factories, vol. 11, No. 1, pp. 1-12, Aug. 20, 2012.
Arnold Marina et al. "Protective Vaccination against Infectious Bursal Disease Virus with Whole Recombinant *Kluyveromyces lactis* Yeast Expressing the Viral VP2 Subunit", vol. 7, No. 9, 01, pp. e42870.1-e42870.11, Sep. 1, 2012.
Takako Iwata et al. "Efficient secretion of human lysozyme from the yeast. *Kluyveromyces lactis*" Biotechnology Leiters, Springer Netherlands, Dordrecht, vol. 26, No. 23, , pp. 1803-1808, Dec. 1, 2004.
Mustilli AC et al. "Comparison of secretion of a hepatitis C virus glycoprotein in *Saccharomyces cerevisiae* and Kluyveromyces lactis", Research in Microbiology, Elsevier, Amsterdam, NL, vol. 150, No. 3, pp. 179-187, Apr. 1, 1999.
Constance Mehlgarten et al. "Divergent Evolution of the Transcriptional Network Controlled by Snf1-Interacting Protein Sip4 in Budding Yeasts", PLOS One, vol. 10, No. 10, p. e0139464, Jun. 1, 2015.
Albert J.J. Van Ooyen et al. "Heterologous protein production in the yeast *Kluyveromyces lactis*", FEMS Yeast Research, GB, NL, vol. 6, No. 3, pp. 381-392, May 1, 2006.

* cited by examiner

*Primary Examiner* — Benjamin P Blumel
(74) *Attorney, Agent, or Firm* — JMB Davis Ben-David

(57) ABSTRACT

The invention relates to recombinant *Kluyveromyces lactis* (*K. lactis*) yeasts which are capable of the highly efficient expression of one or more foreign proteins and are suitable for use as a vaccine for generating a protective immune response against pathogens. The invention provides in particular *K. lactis* strains for the targeted cloning of foreign antigen-coding nucleic acids into the yeast genome of the *K. lactis* strain, which is characterized in that the *K. lactis* strain has integrated expression cassettes for foreign antigens as an alternative or in addition to the KlLAC4 locus on the KlURA3-20 locus (KLLA0E22771g) and/or on the KlMET5-1 locus (KLLA0B03938g). The invention further relates to integrative expression vectors and to methods for producing the *K. lactis* strains of the invention as well as to the use thereof as vaccines.

Figure 1:
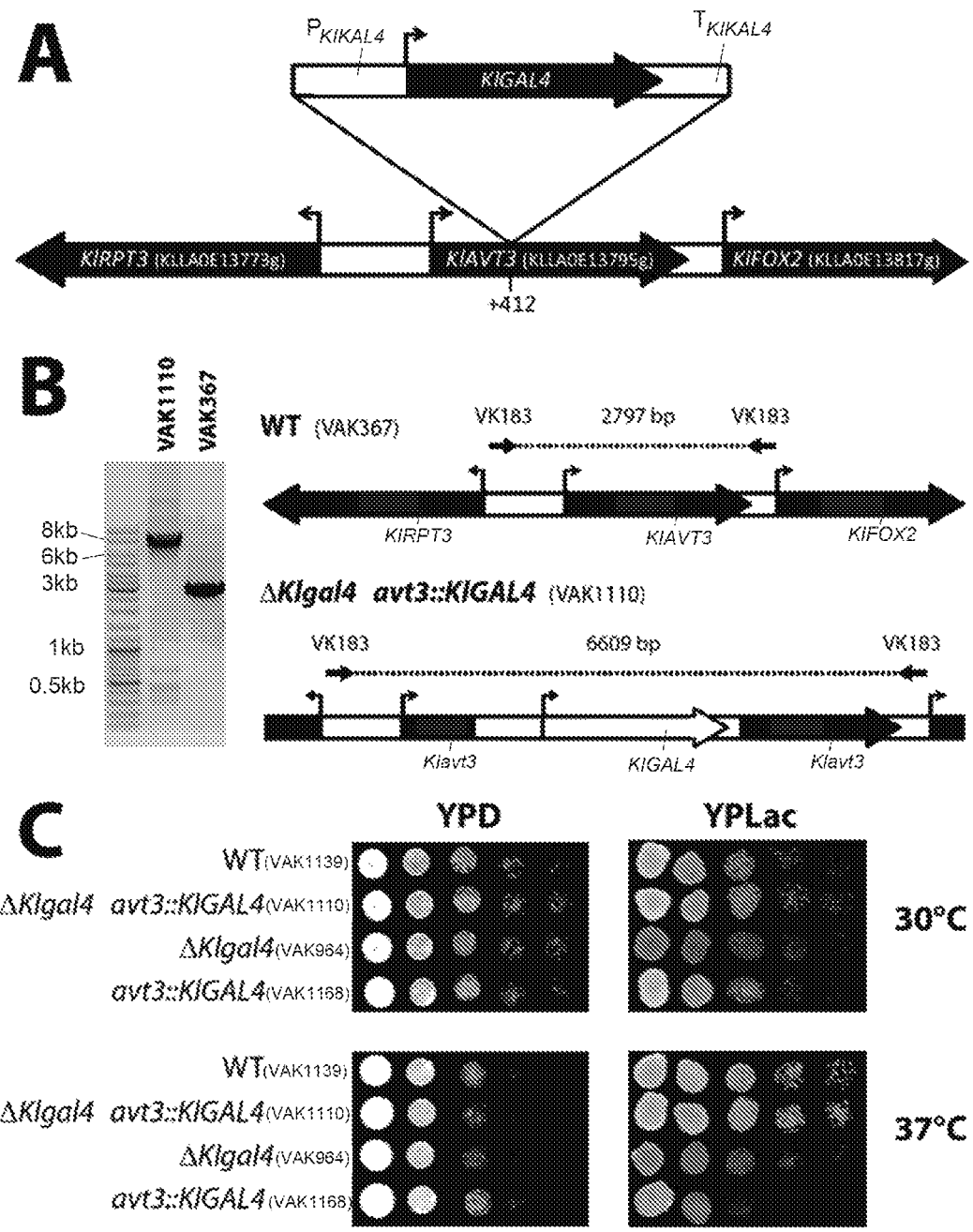

17 Claims, 14 Drawing Sheets
Specification includes a Sequence Listing.

Figure 9

Figure 10

SEQUENCE LISTING

```
<160> NUMBER OF SEQ ID NOS: 25

<210> SEQ ID NO 1
<211> LENGTH: 5042
<212> TYPE: DNA
<213> ORGANISM: Kluyveromyces lactis

<400> SEQUENCE: 1
atgaatatca atatcaagaa agattctgga gggaatgggt ccgatttacc tcgatggaac      60
gattctccgg tgggaagttt agggtcgttt aatgggagaa gaagatcgat gtccttctct     120
gaatcagtaa acttcgcaag aaatactcag aacccattgg atatgtcagc tcaggaaatg     180
agaggattga atggggttcag aagatctttc atcgctcata agtcgttgaa acttcatggg    240
aagacaccga acttatcac taggaatttc aacgagttct tgacgttata cggccatttc     300
gctggtgaag atttgtccga ggatgaggaa acagaaactg aggtggagac tgatgaagat    360
gaggacgaag aagctgcgct tcttcgtcat ggtattaggg gcctgcgcca cctcgacaat    420
ttcaaacgta tcagagtgct ttgccaattg ttcggcagca gtcttcatac ctcttacgat    480
ggcagggtat ggcgttacaa ggttatcagt atataggaca ccgaccttga tcttctgagg    540
cagttcagct tctctccaag gaataggat actagtagta tcagattccc aaggcttacc     600
gtcattaatg taatgtttca taaagtaatc cagctcttca atagatcctc tacgccggac    660
gcatcgtggc cggcatcacc ggcgccacag gtgcggttgc tggcgcctat atcgccgaca    720
tcaccgatgg ggaagatcgg gctcgccact tcgggctcat gagcgcttgt ttcggcgtgg    780
gtatggtggc aggccccgtg gccgggggac tgttgggcgc catctccttg catgcaccat    840
tccttgcggc ggcggtgctc aacggcctca acctactact gggctgcttc ctaatgcagg    900
```

```
agtcgcataa gggagagcgt cgatcgacct ttgacattcg ctgttcaaag ttaccacagc    960
agcaattgat ccaagctaac tcacggcacg ggcgtagcaa gtgaaccgtc gatattgagc   1020
agtgtatgaa tatgcattcg taccagtatt ttgtgtgatc acgcaggact ttacggtttc   1080
acggaccgga acagaccgta ttcctgtcct aagtgtaat gtatgggtgt gatctctgtc    1140
ctccgccttt cccatacaaa agttgctttg aaaagaagt aactgcaaaa tcatagataa    1200
tgacactttg aataactaga ataacaact tcggaccctt gctcaattca agtaagacaa    1260
tatatagcgt acctgccgtt cttccaagtg agggtttgtt ctgttggttc agaaatccca   1320
ggatattcag agttttttaa agcttttctt agagtcaagg cactttttta caccaattgt   1380
actagtaccc aactaaacat aaaagatca gcaaccatcc aaatggttta cgatttgacc    1440
atttgaacat cacagatctg aactttactc cgactgattg tttttactat acgaaatggg   1500
tagtagggcc tccaattcgc cttctttttc aagtaaggcg aaacgttac tgccatcgga    1560
gtataaaaag aatgcggtta agaaggaaac aatacgcaat ggcaagaaaa ggaaattgcc   1620
tgatacagaa tcctcagatc ctgagtttgc aagtcggcgt ttgatagcta atgaaactgg   1680
cactgatgcg gtgagtaatg gtaacaaaaa tgatagcaat gccaacaaca acaacaacaa   1740
caacaacaag aaatcaagtg aagtaatgca ccaggcgtgc gatgcttgca ggaagaagaa   1800
gtggaaatgt tccaagacag taccgacttg cacgaactgt ctgaaataca atttagactg   1860
tgtctactct ccgcaagttg ttaggactcc gttgacaaga gcacatttaa cagagatgga   1920
aaatagggtt gcagagttgg aacagttttt gaaagaactt ttcccagttt gggatatcga   1980
taggttactt cagcaaaaag atacatacag gattagggaa ttgcttacta tgggttctac   2040
aaatactgtt ccgggacttg catcgaataa tatcgattca tcgttagaac agcccgttgc   2100
ctttggtact gcgcagccgg cacaatcttt gtcaactgat ccagcagtac aatctcaagc   2160
ctatccaatg caaccggtac cgatgacaga gcttcaatct atcaccaatc ttcgacacac   2220
gccatcactt ctggatgaac agcaaatgaa cacgatttcc acggcaacgc tgcggaacat   2280
gtactcttca ggtaacaata taacaacttt gggtaacatc tctggtctat cacctgttac   2340
agaggcattc ttccgttggc aggaaggtga acgtcaatc gataatagtt attttggaaa    2400
aggttcaatt ttgttttggt tgaaccaatt actatcatca gaaaagatcg ctggcgttac   2460
atcaaaagta ggcaatgaca ttaacactaa taataataat ataaaccatc agaagctacc   2520
tctaatacta aacaataata ttactcataa tgtgtcggac ataaccacaa caagtacatc   2580
ttcaaacaaa agggcaatgt ctcctctttc tgccaatgac tctgtatatc tcgctaaaag   2640
agagacaata tccgcgtata tcgatgcgta cttcaagcac tatcatgcgc tatatccgtt   2700
ggtcagtaag gaaatgtttt tcgctcagta taatgatcaa attaaaccag aaacgttga   2760
gatatggcac atcttactaa acgcggtatt agctttgggt tcatggtgct ctaattcatg   2820
ttcaagtcac catactctct attaccaaaa cgcattatca tatttgtcca ccgctgtatt   2880
ggaaacaggg tccacagatt taaccatagc actcatactt ttaacgcatt atgttcaaaa   2940
gatgcataag ccaaacactg catggagtct cataggactt tgtagccata tggctacatc   3000
gttgggatta caccgggatc taccaaactc aacgatacat gatcagcaac tccgtagagt   3060
attgtggtgg actatttatt gcacgggatg cgatctctca ttagagactg aaggccctc    3120
attattgccc aatcttcagg ctattgatat accattacca gcttcatctg ccactatcaa   3180
agaaccaagc atatattcct ccatcataca agaatcccaa tggtctcaaa tattgcaaca   3240
```

| | |
|---|---:|
| gaaattgtca aataactcat atcagcaaag tgcaggtgaa tgtctctcat ggttcgatag | 3300 |
| tgttcaagca tttttagacc actggcctac tcctagtacc gaagctgaac tcaaagcctt | 3360 |
| aaatgaaact caactagatt ggctaccatt agtgaagttc cggccatact ggatgttcca | 3420 |
| ttgttcccta atatcacttt tctcagtttt ttttgaagaa gatgcccccaa ccgacaacaa | 3480 |
| cgtcatacgg tgcaaggagt tatgccttca actttcaagc agaaatatat ttagcgtggc | 3540 |
| cacttttgta cggagctatg cattcaactc actttcctgt tggtacgcga cacattatct | 3600 |
| tgttagaagc gcattagtgc ctctacattt cgcatctcgg atatctccac agcacgcctt | 3660 |
| gtgggagaca gttaaagcgc aattattatc agcccatgaa gcgatgggta tattgtcaca | 3720 |
| agaatcttcc ttggccgcta aatttgatgg gatattaacc aagaattatt ctgaaatact | 3780 |
| acaaagagaa ggcatcaaca aaagccaact gatgccacca ccaactccat tgctacaatc | 3840 |
| aaccagtttc tcggacctac tttcactgtg gtcagcaaac gcagaagacg ctccgagagt | 3900 |
| cagtaattcc cagatgcctc aatcgatcac tatcacggac tctttgctac agtcatcaac | 3960 |
| aactcaaatg agacctccaa ccacatctgg atggcctgat accaacaact tcctgaatcc | 4020 |
| atcgacccaa cagctattca acaccacaac aatggacgat gtgtacaact atatatttga | 4080 |
| taacgacgag taagaaatct ctcttttccg tagtcaattg ggacagcatc aattcatgta | 4140 |
| tttactttt gttcagtagc tatcaaatag ctatccaacg agaccactgg tacgaacagt | 4200 |
| gtccatcatg cacattgtag gtaacccagg gagcggatcg gtatggcgaa gagacttcat | 4260 |
| cgatggccat cgatgatgac gaaggtagtt cggaaaataa cgatatccag caacaacagc | 4320 |
| agctgaagca gcagcagcag cacttgcata agaagaaaag aaatacgtcc accacgaagg | 4380 |
| cggtacttct ccttctaaag tcgttcgtag gtaccggggt tcttttttcta cctagagctt | 4440 |
| tccataacgg tgggtggttg ttcagtacgc tgtgtctttt gttctgcgcc acggtgtctt | 4500 |
| tctactgctt catcctgttg atagacacga agactgctgt tggagtggat ggatacggtg | 4560 |
| aattgggttc acgtttattc ggacccaaat tgaagttcac tgtccttttca tcgattgtac | 4620 |
| tctcgcaaat cggatttgct gctgcttata ctgtgttcac tgcaacaaac ttgcaggcat | 4680 |
| tcttcaaaca tgtcttttct ctcgaatact cgttaatctt ctggattatg atccaactag | 4740 |
| cattctattt gccgctatca ttgactagaa acattgcaag actcagtgcc accgctttgg | 4800 |
| tagcagatct tttcattctc ttgggtctag tatacgtcta ttattattcc agtttctata | 4860 |
| tttggaacca tggcatcgct tcggattcca tggtgtcttt caacaaatcg gactggacgt | 4920 |
| tatttattgg aactgcgata ttcacatatg agggtatcgg tctcttgatc ccaatccatg | 4980 |
| aatctatgga aaacctgca catttcaaac cggcattgat gtacgtcatc ctcgttgtaa | 5040 |
| ca | 5042 |

<210> SEQ ID NO 2
<211> LENGTH: 2349
<212> TYPE: DNA
<213> ORGANISM: Artificial sequence
<220> FEATURE:
<223> OTHER INFORMATION: Synthetic polynucleic acid

<400> SEQUENCE: 2

| | |
|---|---:|
| cgtaattctg tctttaatca ttaacactga ctgaaggata taattataag acaacacaca | 60 |
| gagactttg tttgctgttt agcttacact ttccagctat attgaatagc atatatatgt | 120 |
| tccagaagct acaaccacct tgaactacag cccaactcaa cattgaaagt tactgccttt | 180 |
| atataccttg atacaccatt tagacctcca attaaccgat tgtccttgtc ataatgagct | 240 |

```
agagtagcaa ggtatcaaca acagtatgga catcttattg tcaactttct agtacggagg        300
gaagaatccc gaatatgtta atctgacgc gcgggtattg ctaagtcacg ttgcaggccc         360
acgcagaccc gagtttcttt cttacaaaag cgtgtacaca cgtaaacgcg ctcggtgcac        420
cgaacggcca gggtcggggt tcattcggta tagagccacg caggtaactt gccaattcca        480
aaaaaaatta aatgacgata ctagtaacca aggaaaagga acagatagat aaaattccga        540
gactgtcaaa ttaggttttt ttcttttttt ttggcgggag tcagtgggcc gaaatatgtt        600
cttggcctag aacttaatct ggtttgatca tgccaatact tgcctgagtg cccgactttt        660
tgcccaccct cttgccttct gtctatcctt caaaacccac ctgttttcca gccgtatctt        720
cgctcgcatc tacacatact gtgccatatc ttgtgtgtag ccggacgtga ctatgaccaa        780
aaacaaacaa ggagaactgt tcgccgattt gtaacactcc tgcatccatc caagtgggta       840
tgcgctatgc aatgttaagc taggtcaggt cagaccaggt ccaaggacag caacttgact       900
gtatgcaacc tttaccatct ttgcacagaa catacttgta gctagctagt tacacttatg        960
gaccgaaaag gcaccccacc atgtctgtcc ggctttagag tacggccgca gaccgctgat      1020
ttgccttgcc aagcagtagt cacaatgcat cgcatgagca cacgggcacg ggcacgggca      1080
caggaaccat tggcaaaaat accagataca ctataccgac gtatatcaag cccaagttta      1140
aaattcctaa atttccgcgg ggatcgactc ataaaatagt aaccttctaa tgcgtatcta      1200
ttgactacca accattagtg tggttgcaga aggcggaatt cgtcgacgaa cttgtttaat      1260
tattatgggg caggcgagag ggggaggaat gtatgtgtgt gaggcgggcg agacggagcc      1320
atccaggcca ggtagaaata gagaaagccg aatgttagac aatatggcag cgtagtagag      1380
taggtaggta ggcaagtact gctagcaaag aggagaaggg taagctcact cttcgcattc      1440
cacaccgtta gtgtgtcagt ttgaacaaaa aaacaatcat cataccaatt gatggactgt      1500
ggactggctt ttggaacggc ttttcggact gcgattattc gtgaggaatc aaggtaggaa      1560
tttggtcata tttacggaca acagtgggtg attcccatat ggagtaggaa aacgagatca      1620
tggtatcctc agatatgttg cggaattctg ttcaccgcaa agttcagggt gctctggtgg      1680
gtttcggttg gtctttgctt tgcttctccc ttgtcttgca tgttaataat agcctagcct      1740
gtgagccgaa acttagggta ggcttagtgt tggaacgtac atatgtatca cgttgacttg      1800
gtttaaccag gcgacctggt agccagccat acccacacac gttttttgta tcttcagtat      1860
agttgtgaaa agtgtagcgg aaatttgtgg tccgagcaac agcgtctttt tctagtagtg      1920
cggtcggtta cttggttgac attggtattt ggactttgtt gctacaccat tcactacttg      1980
aagtcgagtg tgaagggtat gatttctagt ggtgaacacc tttagttacg taatgttttc      2040
attgctgttt tacttgagat ttcgattgag aaaaaggtat ttaatagctc gaatcaatgt      2100
gagaacagag agaggatgtt cttccctaac tcgaaggta tatgaggctt gtgtttctta       2160
ggagaattat tattcttttg ttatgttgcg cttgtagttg gaaaaggtga agagacaaaa      2220
gctggaattg tgagcggata acaagctcaa cacttgaaat ttaggaaaga gcagaatttg      2280
gcaaaaaaaa taaaaaaaaa ataaacacac atactcatcg agaagctgta ccgtcgacgg      2340
cgcgccatg                                                              2349
```

<210> SEQ ID NO 3
<211> LENGTH: 7964
<212> TYPE: DNA
<213> ORGANISM: Artificial sequence
<220> FEATURE:

<223> OTHER INFORMATION: Synthetic polynucleic acid
<220> FEATURE:
<221> NAME/KEY: Variant
<222> LOCATION: (6628)..(6629)
<223> OTHER INFORMATION: nn is aa, ag, or ga

<400> SEQUENCE: 3

| | | | | | |
|---|---|---|---|---|---|
| aggtggcact | tttcggggaa | atgtgcgcgg | aaccccctatt | tgtttatttt | tctaaataca | 60 |
| ttcaaatatg | tatccgctca | tgagacaata | accctgataa | atgcttcaat | aatattgaaa | 120 |
| aaggaagagt | atgagtattc | aacatttccg | tgtcgccctt | attccctttt | ttgcggcatt | 180 |
| ttgccttcct | gtttttgctc | acccagaaac | gctggtgaaa | gtaaaagatg | ctgaagatca | 240 |
| gttgggtgca | cgagtgggtt | acatcgaact | ggatctcaac | agcggtaaga | tccttgagag | 300 |
| ttttcgcccc | gaagaacgtt | ttccaatgat | gagcactttt | aaagttctgc | tatgtggcgc | 360 |
| ggtattatcc | cgtattgacg | ccgggcaaga | gcaactcggt | cgccgcatac | actattctca | 420 |
| gaatgacttg | gttgagtact | caccagtcac | agaaaagcat | cttacggatg | gcatgacagt | 480 |
| aagagaatta | tgcagtgctg | ccataaccat | gagtgataac | actgcggcca | acttacttct | 540 |
| gacaacgatc | ggaggaccga | aggagctaac | cgcttttttg | cacaacatgg | gggatcatgt | 600 |
| aactcgcctt | gatcgttggg | aaccggagct | gaatgaagcc | ataccaaacg | acgagcgtga | 660 |
| caccacgatg | cctgtagcaa | tggcaacaac | gttgcgcaaa | ctattaactg | gcgaactact | 720 |
| tactctagct | tcccggcaac | aattaataga | ctggatggag | gcggataaag | ttgcaggacc | 780 |
| acttctgcgc | tcggcccttc | cggctggctg | gtttattgct | gataaatctg | gagccggtga | 840 |
| gcgtgggtct | cgcggtatca | ttgcagcact | ggggccagat | ggtaagccct | cccgtatcgt | 900 |
| agttatctac | acgacgggga | gtcaggcaac | tatggatgaa | cgaaatagac | agatcgctga | 960 |
| gataggtgcc | tcactgatta | agcattggta | actgtcagac | caagtttact | catatatact | 1020 |
| ttagattgat | ttaaaacttc | atttttaatt | taaaaggatc | taggtgaaga | tcctttttga | 1080 |
| taatctcatg | accaaaatcc | cttaacgtga | gttttcgttc | cactgagcgt | cagaccccgt | 1140 |
| agaaaagatc | aaaggatctt | cttgagatcc | ttttttctg | cgcgtaatct | gctgcttgca | 1200 |
| aacaaaaaaa | ccaccgctac | cagcggtggt | ttgtttgccg | gatcaagagc | taccaactct | 1260 |
| ttttccgaag | gtaactggct | tcagcagagc | gcagatacca | aatactgttc | ttctagtgta | 1320 |
| gccgtagtta | ggccaccact | tcaagaactc | tgtagcaccg | cctacatacc | tcgctctgct | 1380 |
| aatcctgtta | ccagtggctg | ctgccagtgg | cgataagtcg | tgtcttaccg | ggttggactc | 1440 |
| aagacgatag | ttaccggata | aggcgcagcg | gtcgggctga | acggggggtt | cgtgcacaca | 1500 |
| gcccagcttg | gagcgaacga | cctacaccga | actgagatac | ctacagcgtg | agctatgaga | 1560 |
| aagcgccacg | cttcccgaag | ggagaaaggc | ggacaggtat | ccggtaagcg | gcagggtcgg | 1620 |
| aacaggagag | cgcacgaggg | agcttccagg | gggaaacgcc | tggtatcttt | atagtcctgt | 1680 |
| cgggtttcgc | cacctctgac | ttgagcgtcg | atttttgtga | tgctcgtcag | ggggggcggag | 1740 |
| cctatggaaa | aacgccagca | acgcggcctt | tttacggttc | ctggccttt | gctggccttt | 1800 |
| tgctcacatg | ttctttcctg | cgttatcccc | tgattctgtg | gataaccgta | ttaccgcctt | 1860 |
| tgagtgagct | gataccgctc | gccgcagccg | aacgaccgag | cgcagcgagt | cagtgagcga | 1920 |
| ggaagcggaa | gagcgcccaa | tacgcaaacc | gcctctcccc | gcgcgttggc | cgattcatta | 1980 |
| atgcagctgg | cacgacaggt | ttcccgactg | gaaagcgggc | agtgagcgca | acgcaattaa | 2040 |
| tgtgagttag | ctcactcatt | aggcaccca | ggctttacac | tttatgctcc | cggctcgtat | 2100 |
| gttgtgtgga | attgtgagcg | gataacaatt | tcacacagga | aacagctatg | accatgatta | 2160 |

```
cgccaagcgc gcaattaacc ctcactaaag ggaacaaaag ctgggtaccg ggcccggtga    2220
cctcattgca gtcgtttata ctcctcagga gaacgcagtt gcgacctcat ataatcaagc    2280
aaaagaagac cggcagtagt tccaggaata attgccaaag tattcctagt aaaacccttta   2340 tataaccaag caatggtttc tctcttactt ctcttcatga aaagaacac atgctcgaat     2400 gtatccaagt atgagttgta atagatgtga aacctactac tgcctttggg tatccttatt   2460
ttcgtatttg gaatatttcc tatagttgta ctagacgttg atggtagatt tttgagataa   2520
atatcgtacg cttcaagtct agagacgtgg attttctgta gctttaggaa cgggaattgc   2580
accgattgaa gaacaaaagc tgctgtaaca cctccaataa aaatgaaaac tcttgaatac   2640
cacatttcct cttaggaga aattaaccttt ggtttcttcg tttcaatctt attaccatct   2700
tcatcgaaaa atatatccga gagtcttgtg ttctgcaccg tatatttag ttccctataa    2760 ttcttgataa aatctaacat caattggcga attggtcctc tgatcatttc aaaagtagtg   2820
aaatacaatg caaagccaaa ggattctctt atgaatgata tccaaaccc ccaaagcag     2880 ccaatcaaac caatctctct gatcttatca cgactataaa gccatagatt atcatatttt   2940
tttgcgctgg ataaaagttc atcaatgttt gctcttgtat aaatggcatc tattggagct   3000
gagacaatgg cttgtgcagc acctgcaagg aatcctgctc ttaaaaaatc aaacatatta   3060
tgttgaaaag cttgatctgt agccctcaac ggaaaattat tcaaagtggc taaataagta   3120
gtgtatagca caactcccgc cagcgaattg gctactaatg gcggtaaaat tctgtcaggt   3180
atgactttcc aaccatatct gttcaatgct ttagtgacga ttccgattga agagttctcc   3240
aaataataag tatactttgg attccaaaac cgatacctcg aacttcgtac ttttgtctcg   3300
gactgtgtat tatcgctacc tgtaagaagt actcgaatgt aatgagtata gtcaaatcta   3360
gctggtctga acaattttaa cggagtcctc atgtaaaag atgttagttg atacaccata    3420
gatcttccac cagcagtagc agcacccaca agagaagagg tttggtttga taatgaattg   3480
acatttgctt tatctgaaac atcttccaat ctcttgttgg catcagaaga catcactgtc   3540 tcttccccctt aatgatcact tgaacaaaac tccgataggg tatagtcaat atgtgaaact   3600
ggacactata tcaaagcaaa aagtagtgtt ggatgctaaa tgggatcgtt ttatttaggt   3660
tctatcgagg agaaaaagcg acaagaagag atagaccatg gataaatgat tatgttctaa   3720
acactcctca gaagctcatc gaactgtcat cctgcgtgaa gattaaaatc caacttagaa   3780
atttcgagct tcgaaccgcg gcccgggctc gagcgtaatt ctgtctttaa tcattaacac   3840
tgactgaagg atataattat aagacaacac acagagactt ttgtttgctg tttagcttac   3900
actttccagc tatattgaat agcatatata tgttccagaa gctacaacca ccttgaacta   3960
cagcccaact caacattgaa agttactgcc tttatatacc ttgatacacc atttagacct   4020
ccaattaacc gattgtcctt gtcataatga gctagagtag caaggtatca acaacagtat   4080
ggacatctta ttgtcaactt tctagtacgg agggaagaat cccgaatatg ttaaatctga   4140
cgcgcgggta ttgctaagtc acgttgcagg cccacgcaga cccgagtttc tttcttacaa   4200
aagcgtgtac acacgtaaac gcgctcggtg caccgaacgg ccagggtcgg ggttcattcg   4260
gtatagagcc acgcaggtaa cttgccaatt ccaaaaaaaa ttaaatgacg atactagtaa   4320
ccaaaggaaa ggaacagata gataaaattc cgagactgtc aaattaggtt ttttctttt    4380 tttttggcgg gagtcagtgg gccgaaatat gttcttggcc tagaacttaa tctggtttga   4440
tcatgccaat acttgcctga gtgcccgact ttttgcccac cctcttgcct tctgtctatc   4500
```

```
cttcaaaacc cacctgtttt ccagccgtat cttcgctcgc atctacacat actgtgccat    4560
atcttgtgtg tagccggacg tgactatgac caaaaacaaa caaggagaac tgttcgccga    4620
tttgtaacac tcctgcatcc atccaagtgg gtatgcgcta tgcaatgtta agctaggtca    4680
ggtcagacca ggtccaagga cagcaacttg actgtatgca acctttacca tctttgcaca    4740
gaacatactt gtagctagct agttacactt atggaccgaa aaggcacccc accatgtctg    4800
tccggcttta gagtacggcc gcagaccgct gatttgcctt gccaagcagt agtcacaatg    4860
catcgcatga gcacacgggc acgggcacgg gcacaggaac cattggcaaa ataccagat    4920 acactatacc gacgtatatc aagcccaagt ttaaaattcc taaatttccg cggggatcga    4980
ctcataaaat agtaaccttc taatgcgtat ctattgacta ccaaccatta gtgtggttgc    5040
agaaggcgga attctcccctt cttcgaattc agcttgcttt ttcattttt attttccatt    5100 tttcagtttt tgtttgtgtc gaatttagcc agttgcttct ccaagatgaa aaaaacccct    5160
gcgcagtttc tgtgctgcaa gatcctaatc gacttttcca ccccccacaa aagtaaatgt    5220
tcttttgtta cattcgcgtg ggtagctagc tccccgaatc ttcaaaggac ttagggactg    5280
cactacatca gagtgtgttc acctggtttg ctgcctggtt tgaaagaaaa gagcagggaa    5340
ctcgcgggtt cccggcgaat aatcatgcga tagtcctttg gccttccaag tcacatgtag    5400
agtagacaac agacagggag ggcaggaagg atctttcact gagatcctgt atcttgttgg    5460
gtaagtcgga tgaaagggga atcgtatgag attggagagg atgcggaaga ggtaacgcct    5520
tttgttaact tgtttaatta ttatggggca ggcgagaggg ggaggaatgt atgtgtgtga    5580
ggcgggcgag acggagccat ccaggccagg tagaaataga gaaagccgaa tgttagacaa    5640
tatggcagcg tagtagagta ggtaggtagg caagtactgc tagcaaagag gagaagggta    5700
agctcactct tcgcattcca caccgttagt gtgtcagttt gaacaaaaaa acaatcatca    5760
taccaattga tggactgtgg actggctttt ggaacggctt ttcggactgc gattattcgt    5820
gaggaatcaa ggtaggaatt tggtcatatt tacggacaac agtgggtgat tcccatatgg    5880
agtaggaaaa cgagatcatg gtatcctcag atatgttgcg gaattctgtt caccgcaaag    5940 tcagggtgc tctggtgggt ttcggttggt cttttgctttg cttctccctt gtcttgcatg    6000
ttaataatag cctagcctgt gagccgaaac ttagggtagg cttagtgttg gaacgtacgt    6060
atgtatcacg ttgacttggt ttaaccaggc gacctggtag ccagccatac ccacacacgt    6120
tttttgtatc ttcagtatag ttgtgaaaag tgtagcggaa atttgtggtc gagcaacag    6180 cgtcttttc tagtagtgcg gtcggttact tggttgacat tggtatttgg actttgttgc    6240
tacaccattc actacttgaa gtcgagtgtg aagggtatga tttctagtgg tgaacaccctt    6300 tagttacgta atgttttcat tgctgttta cttgagattt cgattgagaa aaaggtatt    6360 aatagctcga atcaatgtga gaacagagag aggatgttct tccctaactc gaaaggtata    6420
tgaggcttgt gtttcttagg agaattatta ttcttttgtt atgttgcgct tgtagttgga    6480
aaaggtgaag agacaaaagc tggaattgtg agcggataac aagctcaaca cttgaaattt    6540
aggaaagagc agaatttggc aaaaaaaata aaaaaaata acacacata ctcatcgaga    6600 agctgtaccg tcgacggcgc gccatgtnng cggccgcctc gactcagtac tgacaataaa    6660
aagattcttg ttttcaagaa cttgtcattt gtatagtttt tttatattgt agttgttcta    6720
ttttaatcaa atgttagcgt gatttatat ttttttcgcc tcgacatcat ctgcccagat    6780
gcgaagttaa gtgcgcagaa agtaatatca tgcgtcaatc gtatgtgaat gctggtcgct    6840
atactgctgt cgattcgata ctaacgccgc catccagtgt cgaaaacgag ctctcgacac    6900
```

-continued

| | |
|---|---|
| gcgtcacaag cttcggagac aatcatatgg gagaagcaat tggaagatag aaaaaaggta | 6960 |
| ctcggtacat aaatatatgt gattctgggt agaagatcgg tctgcattgg atggtggtaa | 7020 |
| cgcattttt tacacacatt acttgcctcg agcatcaaat ggtggttatt cgtggatcta | 7080 |
| tatcacgtga tttgcttaag aattgtcgtt catggtgaca cttttagctt tgacatgatt | 7140 |
| aagctcatct caattgatgt tatctaaagt catttcaact atctaagatg tggttgtgat | 7200 |
| tgggccattt tgtgaaagcc agtacgccag cgtcaataca ctcccgtcaa ttagttgcac | 7260 |
| catgtccaca aaatcatata ccagtagagc tgagactcat gcaagtccgg ttgcatcgaa | 7320 |
| acttttacgt ttaatggatg aaaagaagac caatttgtgt gcttctcttg acgttcgttc | 7380 |
| gactgatgag ctattgaaac ttgttgaaac gttgggtcca tacatttgcc ttttgaaaac | 7440 |
| acacgttgat atcttggatg atttcagtta tgagggtact gtcgttccat tgaaaagcatt | 7500 |
| ggcagagaaa tacaagttct tgatatttga ggacagaaaa ttcgccgata tcggtaacac | 7560 |
| agtcaaatta caatatacat cgggcgttta ccgtatcgca gaatggtctg atatcaccaa | 7620 |
| cgcccacggg gttactggtg ctggtattgt tgctggcttg aaacaaggtg cgcaagaggt | 7680 |
| caccaaagaa ccaaggggat tattgatgct tgctgaattg tcttccaagg gttctctagc | 7740 |
| acacggtgaa tatactaagg gtaccgagct ccaattcgcc ctatagtgag tcgtattacg | 7800 |
| cgcgctcact ggccgtcgtt ttacaacgtc gtgactggga aaaccctggc gttacccaac | 7860 |
| ttaatcgcct tgcagcacat ccccctttcg ccagctggcg taatagcgaa gaggcccgca | 7920 |
| ccgatcgccc ttcccaacag ttgcgcagcc tgaatggcga atgg | 7964 |

```
<210> SEQ ID NO 4
<211> LENGTH: 9728
<212> TYPE: DNA
<213> ORGANISM: Artificial sequence
<220> FEATURE:
<223> OTHER INFORMATION: Synthetic polynucleic acid
<220> FEATURE:
<221> NAME/KEY: Variant
<222> LOCATION: (4962)..(4963)
<223> OTHER INFORMATION: nn is aa, ag, or ga

<400> SEQUENCE: 4
```

| | |
|---|---|
| tcagctctgg gagaaacttg gtgtttccgg tgcaactgtc cctgatgaac caaagccgat | 60 |
| caccaatgaa gatatcaaaa ttgcttccaa tttcctcaga ggtacaattg tggaagggct | 120 |
| acaagatgaa tcaactggtg caatttctgc gtgggatcag caattaacca agttccatgg | 180 |
| tatctatatg caagatgatc gtgatataag agacactagg aagagtcaag gtcttgaacc | 240 |
| ttattacatt tcatgtcaa gagttagatt accaggtgga aaggccaatc cagatcaatg | 300 |
| gttgattctt gatcacttag cagacaaaac tggtaacggt acagttaaaa ttaccaccag | 360 |
| agcaactttc caattgcatg gtgttgttaa gcacaattta aagcacacta tcagagctat | 420 |
| gaattccacc ttgatggaca ctttagcggc gtgtggtgat gttaacagaa atgtcatgct | 480 |
| ttctgctttg cctgctaatg ccacggttca caaacaaatt gcagacgttg gtacatatct | 540 |
| ttctgaacgt ttcttgcctc aaacaacggc gtatcacgaa atttggttag agggtccaga | 600 |
| caaggatgat gaagatcctt cttggccaga gacctacaga aaaagacaag aaggtcctat | 660 |
| aaagaagaag aaaactcttg ttgccggtaa tgcattagtt gatgcggaac cagtctatgg | 720 |
| tccaacatac ttaccaagaa agttcaagat caatattact gttccaccct tcaatgatgt | 780 |
| cgatgtgtgg tccagtgacg ttggtttgat tgctataatt gatgaaccaa ctcaaactct | 840 |

```
aacaggtttc aatctctatg ttggtggtgg tatggggagt acccacaaca acaaaaagac    900
atacccaaga acaggttcgt tgttcgggta tgtctccgta gcagatgtgg gagatgccat    960
tgaaaaggtg atgattgttc aaagagatca tggtgatcgt accaaccgta agcacgctcg   1020
tttaaagtac actgttgatg atttgaccat tgaaggttac aagcagaagg tcgaagaact   1080
atggggcaag aagtttgaac ctgctgctgc gtatgagatc aaatcaaaca ttgattactt   1140
cggttgggta aaggatgaaa ctggactaaa tcatttcact gccttcattg aaaatggtag   1200
agtggaagat acagtagagc tgcctcagaa aacaggtttc aggaaaattg cacagttgat   1260
gaagaaagat aacttcggtc acttcagatt aaccggtaac caacacgttc ttatctcaga   1320
cgttgatgac gagcatttag acgaagttaa agctatcatg aacaagtaca agctagacaa   1380
cacgaacttc agtggattga ggttatcgtc tgctgcatgt gttgctttgc aacctgtgg    1440
tttggctatg gccgaatctg aacgttattt gcctgtttta atcacaaagc tggagaatgc   1500
attagaagag tatgggttac gccacgattc tattgtcatg agaatgactg gttgtccaaa   1560
tggttgtgct cgtccatggt tagctgaggt tgctttagtg ggtaaagccc caggaactta   1620
taatctatta ctcggaggtg ttattacgg tcaaagattg aacaaactat acagagcatc    1680
catcaaagaa gatgaaattt tagccacatt gaaacctcta tttaagaggt ggtccttgga   1740
aagactcgaa ggtgaacact tcggggattt cgtcattaga gtaggtgtta tcaaaccaac   1800
cttggaaggt aaatacttcc atgatgatct tccagaagaa gctctatgag ggagccaact   1860
cctttcatat gggagggccg catcatgtaa ttagttatgt cacgcttaca ttcacgccct   1920
cccccacat ccgctctaac cgaaaaggaa ggagttagac aacctgaagt ctaggtccct    1980
atttattttt ttatagttat gttagtatta agaacgttat ttatatttca aattttctt    2040
ttttttctgt acagacgcgt gtacgcatgt aacattatac tgaaaacctt gcttgagaag   2100
gttttgggac gctcgaaggc tttaatttgc ggccccgggg ctcgagcgta attctgtctt   2160
taatcattaa cactgactga aggatataat tataagacaa cacacagaga cttttgtttg   2220
ctgtttagct tacactttcc agctatattg aatagcatat atatgttcca gaagctacaa   2280
ccaccttgaa ctacagccca actcaacatt gaaagttact gccttatat acctggatac    2340
accatttaga cctccaatta accgattgtc cttgtcataa tgagctagag tagcaaggta   2400
tcaacaacag tatggacatc ttattgtcaa ctttctagta cggagggaag aatcccgaat   2460
atgttaaatc tgacgcgcgg gtattgctaa gtcacgttgc aggcccacgc agacccgagt   2520
ttctttctta caaaagcgtg tacacacgta aacgcgctcg gtgcaccgaa cggccagggt   2580
cggggttcat tcggtataga gccacgcagg taacttgcca attccaaaaa aaattaaatg   2640
acgatactag taaccaaagg aaaggaacag atagataaaa ttccgagact gtcaaattag   2700
gttttttttct ttttttttgg cgggagtcag tgggccgaaa tatgttcttg gcctagaact   2760
taatctggtt tgatcatgcc aatacttgcc tgagtgcccg acttttttgcc caccctcttg   2820
ccttctgtct atccttcaaa acccacctgt tttccagccg tatcttcgct cgcatctaca   2880
catactgtgc catatcttgt gtgtagccgg acgtgactat gaccaaaaac aaacaaggag   2940
aactgttcgc cgatttgtaa cactcctgca tccatccaag tgggtatgcg ctatgcaatg   3000
ttaagctagg tcaggtcaga ccaggtccaa ggacagcaac ttgactgtat gcaacccttta  3060
ccatctttgc acagaacata cttgtagcta gctagttaca cttatggacc gaaaaggcac   3120
cccaccatgt ctgtccggct ttagagtacg gccgcagacc gctgatttgc cttgccaagc   3180
agtagtcaca atgcatcgca tgagcacacg ggcacgggca cgggcacagg aaccattggc   3240
```

```
aaaaatacca gatacactat accgacgtat atcaagccca agtttaaaat tcctaaattt   3300 ccgcgggat  cgactcataa aatagtaacc ttctaatgcg tatctattga ctaccaacca   3360
ttagtgtggt tgcagaaggc ggaattctcc cttcttcgaa ttcagcttgc ttttcattt    3420 tttatttcc  attttcagt  ttttgtttgt gtcgaattta gccagttgct tctccaagat   3480 gaaaaaacc  cctgcgcagt ttctgtgctg caagatccta atcgactttt ccacccca     3540 caaaagtaaa tgttcttttg ttacattcgc gtgggtagct agctccccga atcttcaaag   3600
gacttaggga ctgcactaca tcagagtgtg ttcacctggt ttgctgcctg gtttaaaga    3660 aaagagcagg gaactcgcgg gttcccggcg aataatcatg cgatagtcct ttggccttcc   3720
aagtcacatg tagagtagac aacagacagg gagggcagga aggatctttc actgagatcc   3780
tgtatcttgt tgggtaagtc ggatgaaagg ggaatcgtat gagattggag aggatgcgga   3840
agaggtaacg cctttttgtta acttgtttaa ttattatggg gcaggcgaga ggggaggaa   3900 tgtatgtgtg tgaggcgggc gagacggagc catccaggcc aggtagaaat agagaaagcc   3960
gaatgttaga caatatggca gcgtagtaga gtaggtaggt aggcaagtac tgctagcaaa   4020
gaggagaagg gtaagctcac tcttcgcatt ccacaccgtt agtgtgtcag tttgaacaaa   4080
aaaacaatca tcataccaat tgatggactg tggactggct tttggaacgg cttttcggac   4140
tgcgattatt cgtgaggaat caaggtagga attttggtcat atttacggac aacagtgggt  4200
gattcccata tggagtagga aaacgagatc atggtatcct cagatatgtt gcggaattct   4260
gttcaccgca aagttcaggg tgctctggtg ggtttcggtt ggtctttgct ttgcttctcc   4320
cttgtcttgc atgttaataa tagcctagcc tgtgagccga aacttagggt aggcttagtg   4380
ttggaacgta cgtatgtatc acgttgactt ggtttaacca ggcgacctgg tagccagcca   4440
tacccacaca cgttttttgt atcttcagta tagttgtgaa aagtgtagcg gaaatttgtg   4500
gtccgagcaa cagcgtcttt ttctagtagt gcggtcggtt acttggttga cattggtatt   4560
tggactttgt tgctacacca ttcactactt gaagtcgagt gtgaagggta tgatttctag   4620
tggtgaacac ctttagttac gtaatgtttt cattgctgtt ttacttgaga tttcgattga   4680
gaaaaaggta tttaatagct cgaatcaatg tgagaacaga gagaggatgt tcttccctaa   4740
ctcgaaaggt atatgaggct tgtgtttctt aggagaatta ttattctttt gttatgttgc   4800
gcttgtagtt ggaaaaggtg aagagacaaa agctggaatt gtgagcggat aacaagctca   4860
acacttgaaa tttaggaaag agcagaattt ggcaaaaaaa ataaaaaaaa aataaacaca   4920
catactcatc gagaagctgt accgtcgacg gcgcgccatg tnngcggccg cctcgactca   4980
gtactgacaa taaaaagatt cttgttttca agaacttgtc atttgtatag ttttttttata  5040 ttgtagttgt tctattttaa tcaaatgtta gcgtgattta tatttttttt cgcctcgaca   5100
tcatctgccc agatgcgaag ttaagtgcgc agaaagtaat atcatgcgtc aatcgtatgt   5160
gaatgctggt cgctatactg ctgtcgattc gatactaacg ccgccatcca gtgtcgaaaa   5220
cgagctcggg agccaactcc tttcatatgc tcccacctgg ccacccaccc acacacacat   5280
acatacacaa acacaaacga tttgtttatt taaatattta ttttgtacat tgtcgcatag   5340
aaaatgcata tttatctgac gttcttcttc gttacgccct ttcatggttt aagggatgac   5400
tcaatttaca ctatcctgca aggtgctaca acaatgtatt agtcaggtga tcgcaaattg   5460
catggaatat ccatggtatc accaaagaag tttcaatctt aaagtcctct ggaaaacctt   5520
tcttactgtg ctttgaaaag accttattcg tattcttacc ctttcaataa atgaccgtgg   5580
```

```
ttttttttttg ttatcgttat aatattagac cataaaatat cgtttacgta aacggtcgac   5640
cttgtcaacg agaaaaaagg aaacaagtcc aacgttattc tagaggtagc cttcatagtt   5700
tcaactggaa ctactccaaa ttatattttc aaaccttcaa agtatgttga ggtttactca   5760
tgtgcttaat aatggggcga aacgctctgc tcttagttta ggaagaagct acttgcgtgg   5820
tttcggttcc atgcatggac ctcgagttgc tgtttcaact ttaatcaaaa aagacaagaa   5880
acctaatggc tttcgtggta tgttggcttt atttgtaggt atcggaacac tcgctgtaag   5940
cgggctttct acaaacttat acaatgatca aaatgttaag gaagatcctt ggaaaagtgt   6000
gtctgttgat aagtctattg acccgttttcc aactgagtta aaggctcctg agttccccat   6060
ttctactgaa tatgttatgt taggctttgg tataaggtcg gttactttca ttagtttcaa   6120
agtttatggg ttaggtatct atgctgcaaa agaggatttg ggattaatcc ctaaagtatt   6180
ggattcaaac tttctttcta ctgcgttcat tgatttcgac tccagtaaaa gtcatcagga   6240
gaatttgaag actgctttag acaaccctga acttccaga attctcatta caacttatt    6300 ggatagtgga atcagattgg tcgcaaaaat cacacctatc agaaacactg acttcaacca   6360
tctcaaagac ggtcttgtga atccattct tgggcatccg gatagtaaaa aggatgaaga   6420
taggttaacg aatggattac aacaattacg cgatgctttc tcaagaaaag gttcagtacc   6480
aaagaataac gatttattga ttgaattgca agccaacgga tatttgcaag tatcctattt   6540
cgatagaaaa acaggagaat ccaccacaat gggacaggta aaagagacat tgatcggtaa   6600
attactcttc agtcaatatt taagtggacc taaaccgtta agtccaagca caaaagattc   6660
tgtggtatct aaattagtta cattggctta agacacgtgt caagcttgat atcctgcatt   6720
aatgaatcgg ccaacgcgcg gggagaggcg gtttgcgtat gggcgctct ccgcttcct    6780 cgctcactga ctcgctgcgc tcggtcgttc ggctgcggcg agcggtatca gctcactcaa   6840
aggcggtaat acggttatcc acagaatcag gggataacgc aggaaagaac atgtgagcaa   6900
aaggccagca aaaggccagg aaccgtaaaa aggccgcgtt gctggcgttt ttccataggc   6960 tccgccccc tgacgagcat cacaaaaatc gacgctcaag tcagaggtgg cgaaacccga   7020
caggactata aagataccag gcgtttcccc ctggaagctc cctcgtgcgc tctcctgttc   7080
cgaccctgcc gcttaccgga tacctgtccg cctttctccc ttcgggaagc gtggcgcttt   7140
ctcatagctc acgctgtagg tatctcagtt cggtgtaggt cgttcgctcc aagctgggct   7200
gtgtgcacga accccccgtt cagcccgacc gctgcgcctt atccggtaac tatcgtcttg   7260
agtccaaccc ggtaagacac gacttatcgc cactggcagc agccactggt aacaggatta   7320
gcagagcgag gtatgtaggc ggtgctacag agttcttgaa gtggtggcct aactacggct   7380
acactagaag aacagtattt ggtatctgcg ctctgctgaa gccagttacc ttcggaaaaa   7440
gagttggtag ctcttgatcc ggcaaacaaa ccaccgctgg tagcggtggt ttttttgttt   7500
gcaagcagca gattacgcgc agaaaaaaag gatctcaaga agatcctttg atcttttcta   7560
cggggtctga cgctcagtgg aacgaaaact cacgttaagg gattttggtc atgagattat   7620
caaaaaggat cttcacctag atcctttta attaaaaatg aagttttaaa tcaatctaaa   7680
gtatatatga gtaaacttgg tctgacagtt accaatgctt aatcagtgag gcacctatct   7740
cagcgatctg tctatttcgt tcatccatag ttgcctgact ccccgtcgtg tagataacta   7800
cgatacggga gggcttacca tctggcccca gtgctgcaat gataccgcga gacccacgct   7860
caccggctcc agatttatca gcaataaacc agccagccgg aagggccgag cgcagaagtg   7920
gtcctgcaac tttatccgcc tccatccagt ctattaattg ttgccgggaa gctagagtaa   7980
```

```
gtagttcgcc agttaatagt ttgcgcaacg ttgttgccat tgctacaggc atcgtggtgt    8040
cacgctcgtc gtttggtatg gcttcattca gctccggttc ccaacgatca aggcgagtta    8100
catgatcccc catgttgtgc aaaaaagcgg ttagctcctt cggtcctccg atcgttgtca    8160
gaagtaagtt ggccgcagtg ttatcactca tggttatggc agcactgcat aattctctta    8220
ctgtcatgcc atccgtaaga tgcttttctg tgactggtga gtactcaacc aagtcattct    8280
gagaatagtg tatgcggcga ccgagttgct cttgcccggc gtcaatacgg gataataccg    8340
cgccacatag cagaacttta aaagtgctca tcattggaaa acgttcttcg gggcgaaaac    8400
tctcaaggat cttaccgctg ttgagatcca gttcgatgta acccactcgt gcacccaact    8460
gatcttcagc atcttttact ttcaccagcg tttctgggtg agcaaaaaca ggaaggcaaa    8520
atgccgcaaa aaagggaata agggcgacac ggaaatgttg aatactcata ctcttccttt    8580
ttcaatatta ttgaagcatt tatcagggtt attgtctcat gagcggatac atatttgaat    8640
gtatttagaa aaataaacaa ataggggttc cgcgcacatt tccccgaaaa gtgccacctg    8700
acgtctaaga aaccattatt atcatgacat taacctataa aaataggcgt atcacgaggc    8760
cctttcgtct cgcgcgtttc ggtgatgacg gtgaaaacct ctgacacatg cagctcccgg    8820
agaaagaaag acgttggtct ctacgctatg aactttggta acgcttacgt cgcatctgtt    8880
gctgtttatt catcatacac acagctactt acatcatttg tcgaagcttc taaatttgtt    8940
ggaccatcaa tcattctagc gtacttgcca tacaactcag aaagagacac tccactagaa    9000 gtttaaaag aaaccaaaat tggtgtcgaa agtggttact ggcctttata caggttttaac    9060 ccttacgaag aacgcgacga ccaagttttc aaattggact cctctgttat caaacaacaa    9120
ctgaaggact ttttagaccg agagaataag ctcactcttc tagctcaaaa gtccccagag    9180
cttgccagaa atttgaagca ttccgcctca gatgcgattc aattgaaaca agacagaagg    9240
gctaaagcag cattcgatca actcttagaa ggtctctctg gccctcctct tcacatttat    9300
catgcttctg acggtggcaa tgcagctaat ttagcaaaaa gattgggtac aagggcatct    9360
gctagaggtc taaaaactat tgtactatca atggaagaca ttgttctaga agagttacca    9420
ggtgaagaga atgttgtatt tataacgtca actgctggtc aaggtgaatt ccctcaagat    9480
ggtaaggcat tttgggatgc tctgaagtct ctactgacc tcgatttagc ttctttgaat    9540
ttctccgtgt ttggtttagg tgactctgca tactggccac gtaaggaaga cgcccattac    9600
tacaacaaac ccgctaagga tttgttcaag agattagaat tgctttctgg tcaagaacta    9660
gtttctttgg gattgggtga tgaccaggat gccgatggtt atcaaacagg ctatgctgtg    9720
tgggaagc                                                             9728
```

<210> SEQ ID NO 5
<211> LENGTH: 2794
<212> TYPE: DNA
<213> ORGANISM: Artificial sequence
<220> FEATURE:
<223> OTHER INFORMATION: Synthetic polynucleic acid

<400> SEQUENCE: 5

```
cgtaattctg tctttaatca ttaacactga ctgaaggata taattataag acaacacaca      60 gagactttg tttgctgttt agcttacact ttccagctat attgaatagc atatatatgt     120
tccagaagct acaaccacct tgaactacag cccaactcaa cattgaaagt tactgccttt     180 ataccttg atacaccatt tagacctcca attaaccgat tgtccttgtc ataatgagct     240
```

```
agagtagcaa ggtatcaaca acagtatgga catcttattg tcaactttct agtacggagg    300
gaagaatccc gaatatgtta aatctgacgc gcgggtattg ctaagtcacg ttgcaggccc    360
acgcagaccc gagtttcttt cttacaaaag cgtgtacaca cgtaaacgcg ctcggtgcac    420
cgaacggcca gggtcggggt tcattcggta tagagccacg caggtaactt gccaattcca    480
aaaaaaatta aatgacgata ctagtaacca aggaaagga acagatagat aaaattccga    540
gactgtcaaa ttaggttttt ttcttttttt ttggcgggag tcagtgggcc gaaatatgtt    600
cttggcctag aacttaatct ggtttgatca tgccaatact tgcctgagtg cccgactttt    660
tgcccaccct cttgccttct gtctatcctt caaaacccac ctgttttcca gccgtatctt    720
cgctcgcatc tacacatact gtgccatatc ttgtgtgtag ccggacgtga ctatgaccaa    780
aaacaaacaa ggagaactgt tcgccgattt gtaacactcc tgcatccatc caagtgggta    840
tgcgctatgc aatgttaagc taggtcaggt cagaccaggt ccaaggacag caacttgact    900
gtatgcaacc tttaccatct ttgcacagaa catacttgta gctagctagt tacacttatg    960
gaccgaaaag gcaccccacc atgtctgtcc ggctttagag tacggccgca gaccgctgat   1020
ttgccttgcc aagcagtagt cacaatgcat cgcatgagca cacgggcacg ggcacgggca   1080
caggaaccat tggcaaaaat accagataca ctataccgac gtatatcaag cccaagttta   1140
aaattcctaa atttccgcgg ggatcgactc ataaaatagt aaccttctaa tgcgtatcta   1200
ttgactacca accattagtg tggttgcaga aggcggaatt ctcccttctt cgaattcagc   1260
ttgcttttc attttttatt ttccattttt cagttttgt ttgtgtcgaa tttagccagt   1320
tgcttctcca agatgaaaaa aaccccctgcg cagtttctgt gctgcaagat cctaatcgac   1380
ttttccaccc cccacaaaag taaatgttct tttgttacat tcgcgtgggt agctagctcc   1440
ccgaatcttc aaaggactta gggactgcac tacatcagag tgtgttcacc tggtttgctg   1500
cctggtttga agaaaagag cagggaactc gcgggttccc ggcgaataat catgcgatag   1560
tcctttggcc ttccaagtcg catgtagagt agacaacaga cagggagggc aggaaggatc   1620
tttcactgag atcctgtatc ttgttgggta agtcggatga aagggaatc gtatgagatt   1680
ggagaggatg cggaagaggt aacgcctttt gttaacttgt ttaattatta tggggcaggc   1740
gagaggggga ggaatgtatg tgtgtgaggc gggcgagacg gagccatcca ggccaggtag   1800
aaatagagaa agccgaatgt tagacaatat ggcagcgtag tagagtaggt aggtaggcaa   1860
gtactgctag caaagaggag aagggtaagc tcactcttcg cattccacac cgttagtgtg   1920
tcagtttgaa caaaaaaaca atcatcatac caattgatgg actgtggact ggcttttgga   1980
acggcttttc ggactgcgat tattcgtgag gaatcaaggt aggaatttgg tcatatttac   2040
ggacaacagt gggtgattcc catatggagt aggaaaacga gatcatggta tcctcagata   2100
tgttgcggaa ttctgttcac cgcaaagttc agggtgctct ggtgggtttc ggttggtctt   2160
tgctttgctt ctcccttgtc ttgcatgtta ataatagcct agcctgtgag ccgaaactta   2220
gggtaggctt agtgttggaa cgtacatatg tatcacgttg acttggttta accaggcgac   2280
ctggtagcca gccataccca cacacgtttt ttgtatcttc agtatagttg tgaaaagtgt   2340
agcggaaatt tgtggtccga gcaacagcgt ctttttctag tagtgcggtc ggttacttgg   2400
ttgacattgg tatttggact tgttgctac accattcact acttgaagtc gagtgtgaag   2460
ggtatgattt ctagtggtga acacctttag ttacgtaatg ttttcattgc tgttttactt   2520
gagatttcga ttgagaaaaa ggtatttaat agctcgaatc aatgtgagaa cagagagagg   2580
atgttcttcc ctaactcgaa aggtatatga ggcttgtgtt tcttaggaga attattattc   2640
```

```
tttgttatg ttgcgcttgt agttggaaaa ggtgaagaga caaaagctgg aattgtgagc    2700
ggataacaag ctcaacactt gaaatttagg aaagagcaga atttggcaaa aaaaataaaa    2760
aaaaaataaa cacacatact catcgagaag ctgt                                2794
```

<210> SEQ ID NO 6
<211> LENGTH: 2329
<212> TYPE: DNA
<213> ORGANISM: Artificial sequence
<220> FEATURE:
<223> OTHER INFORMATION: Synthetic polynucleic acid

<400> SEQUENCE: 6

```
cgtaattctg tctttaatca ttaacactga ctgaaggata taattataag acaacacaca      60 gagactttttg tttgctgttt agcttacact ttccagctat attgaatagc atatatatgt    120
tccagaagct acaaccacct tgaactacag cccaactcaa cattgaaagt tactgccttt    180
atataccttg atacaccatt tagacctcca attaaccgat tgtccttgtc ataatgagct    240
agagtagcaa ggtatcaaca acagtatgga catcttattg tcaactttct agtacggagg    300
gaagaatccc gaatatgtta aatctgacgc gcgggtattg ctaagtcacg ttgcaggccc    360
acgcagaccc gagtttcttt cttacaaaag cgtgtacaca cgtaaacgcg ctcggtgcac    420
cgaacggcca gggtcggggt tcattcggta tagagccacg caggtaactt gccaattcca    480
aaaaaaatta aatgacgata ctagtaacca aaggaaagga acagatagat aaaattccga    540
gactgtcaaa ttaggttttt ttctttttt ttggcgggag tcagtgggcc gaaatatgtt    600
cttggcctag aacttaatct ggtttgatca tgccaatact tgcctgagtg cccgacttt    660 tgcccaccct cttgccttct gtctatcctt caaaacccac ctgttttcca gccgtatctt    720
cgctcgcatc tacacatact gtgccatatc ttgtgtgtag ccggacgtga ctatgaccaa    780
aaacaaacaa ggagaactgt tcgccgattt gtaacactcc tgcatccatc caagtgggta    840
tgcgctatgc aatgttaagc taggtcaggt cagaccaggt ccaaggacag caacttgact    900
gtatgcaacc tttaccatct ttgcacagaa catacttgta gctagctagt tacacttatg    960
gaccgaaaag gcaccccacc atgtctgtcc ggctttagag tacggccgca gaccgctgat   1020
ttgccttgcc aagcagtagt cacaatgcat cgcatgagca cacgggcacg ggcacgggca   1080
caggaaccat tggcaaaaat accagataca ctataccgac gtatatcaag cccaagttta   1140
aaattcctaa atttccgcgg ggatcgactc ataaaatagt aaccttctaa tgcgtatcta   1200
ttgactacca accattagtg tggttgcaga aggcggaatt cgtcgacgaa cttgtttaat   1260
tattatgggg caggcgagag ggggaggaat gtatgtgtgt gaggcgggcg agacggagcc   1320
atccaggcca ggtagaaata gagaaagccg aatgttagac aatatggcag cgtagtagag   1380
taggtaggta ggcaagtact gctagcaaag aggagaaggg taagctcact cttcgcattc   1440
cacaccgtta gtgtgtcagt ttgaacaaaa aacaatcat cataccaatt gatggactgt   1500
ggactggctt ttggaacggc ttttcggact gcgattattc gtgaggaatc aaggtaggaa   1560
tttggtcata tttacggaca acagtgggtg attcccatat ggagtaggaa aacgagatca   1620
tggtatcctc agatatgttg cggaattctg ttcaccgcaa agttcagggt gctctggtgg   1680
gtttcggttg gtctttgctt tgcttctccc ttgtcttgca tgttaataat agcctagcct   1740
gtgagccgaa acttagggta ggcttagtgt tggaacgtac atatgtatca cgttgacttg   1800
gtttaaccag gcgacctggt agccagccat acccacacac gttttttgta tcttcagtat   1860
```

```
agttgtgaaa agtgtagcgg aaatttgtgg tccgagcaac agcgtctttt tctagtagtg    1920
cggtcggtta cttggttgac attggtattt ggactttgtt gctacaccat tcactacttg    1980
aagtcgagtg tgaagggtat gatttctagt ggtgaacacc tttagttacg taatgttttc    2040
attgctgttt tacttgagat ttcgattgag aaaaaggtat ttaatagctc gaatcaatgt    2100
gagaacagag agaggatgtt cttccctaac tcgaaggta tatgaggctt gtgtttctta    2160
ggagaattat tattcttttg ttatgttgcg cttgtagttg aaaaggtga agagacaaaa    2220 gctggaattg tgagcggata acaagctcaa cacttgaaat ttaggaaaga gcagaatttg    2280
gcaaaaaaaa taaaaaaaaa ataaacacac atactcatcg agaagctgt                2329

<210> SEQ ID NO 7
<211> LENGTH: 1638
<212> TYPE: DNA
<213> ORGANISM: Artificial sequence
<220> FEATURE:
<223> OTHER INFORMATION: Synthetic polynucleic acid

<400> SEQUENCE: 7
gcggggatcg actcataaaa tagtaacctt ctaatgcgta tctattgact accaaccatt      60
agtgtggttg cagaaggcgg aattctccct tcttcgaatt cagcttgctt tttcattttt     120
tattttccat ttttcagttt ttgtttgtgt cgaatttagc cagttgcttc tccaagatga     180 aaaaacccc tgcgcagttt ctgtgctgca agatcctaat cgacttttcc accccccaca     240
aaagtaaatg ttcttttgtt acattcgcgt gggtagctag ctccccgaat cttcaaagga     300
cttagggact gcactacatc agagtgtgtt cacctggttt gctgcctggt ttgaaagaaa     360
agagcaggga actcgcgggt tcccggcgaa taatcatgcg atagtccttt ggccttccaa     420
gtcgcatgta gagtagacaa cagacaggga gggcaggaag gatctttcac tgagatcctg     480
tatcttgttg ggtaagtcgg atgaagggg aatcgtatga gattggagag gatgcggaag     540
aggtaacgcc ttttgttaac ttgtttaatt attatgggc aggcgagagg gggaggaatg     600
tatgtgtgtg aggcgggcga acggagcca tccaggccag gtagaaatag agaaagccga     660
atgttagaca atatggcagc gtagtagagt aggtaggtag gcaagtactg ctagcaaaga     720
ggagaagggt aagctcactc ttcgcattcc acaccgttag tgtgtcagtt tgaacaaaaa     780
aacaatcatc ataccaattg atggactgtg gactggcttt tggaacggct tttcggactg     840
cgattattcg tgaggaatca aggtaggaat ttggtcatat ttacggacaa cagtgggtga     900
ttcccatatg gagtaggaaa acgagatcat ggtatcctca gatatgttgc ggaattctgt     960
tcaccgcaaa gttcagggtg ctctggtggg tttcggttgg tctttgcttt gcttctccct   1020
tgtcttgcat gttaataata gcctagcctg tgagccgaaa cttagggtag gcttagtgtt   1080
ggaacgtaca tatgtatcac gttgacttgg tttaaccagg cgacctggta gccagccata   1140
cccacacacg ttttttgtat cttcagtata gttgtgaaaa gtgtagcgga aatttgtggt   1200
ccgagcaaca gcgtcttttt ctagtagtgc ggtcggttac ttggttgaca ttggtatttg   1260
gactttgttg ctacaccatt cactacttga agtcgagtgt gaagggtatg atttctagtg   1320
gtgaacacct ttagttacgt aatgttttca ttgctgtttt acttgagatt tcgattgaga   1380 aaaggtatt taatagctcg aatcaatgtg agaacagaga gaggatgttc ttccctaact   1440 cgaaggtat atgaggcttg tgtttcttag gagaattatt attcttttgt tatgttgcgc   1500
ttgtagttgg aaaaggtgaa gagacaaaag ctggaattgt gagcggataa caagctcaac   1560
acttgaaatt taggaagag cagaatttgg caaaaaaaat aaaaaaaaaa taaacacaca   1620
```

-continued tactcatcga gaagctgt                                                      1638

<210> SEQ ID NO 8
<211> LENGTH: 1081
<212> TYPE: DNA
<213> ORGANISM: Artificial sequence
<220> FEATURE:
<223> OTHER INFORMATION: Synthetic polynucleic acid

<400> SEQUENCE: 8
aacttgttta attattatgg ggcaggcgag aggggagga atgtatgtgt gtgaggcggg         60
cgagacggag ccatccaggc caggtagaaa tagagaaagc cgaatgttag acaatatggc       120
agcgtagtag agtaggtagg taggcaagta ctgctagcaa agaggagaag ggtaagctca       180
ctcttcgcat tccacaccgt tagtgtgtca gtttgaacaa aaaaacaatc atcataccaa       240
ttgatggact gtggactggc ttttggaacg gcttttcgga ctgcgattat tcgtgaggaa       300
tcaaggtagg aatttggtca tatttacgga caacagtggg tgattcccat atggagtagg       360
aaaacgagat catggtatcc tcagatatgt tgcggaattc tgttcaccgc aaagttcagg       420
gtgctctggt gggtttcggt tggtctttgc tttgcttctc ccttgtcttg catgttaata       480
atagcctagc ctgtgagccg aaacttaggg taggcttagt gttggaacgt acatatgtat       540
cacgttgact tggtttaacc aggcgacctg gtagccagcc ataccacac acgttttttg       600
tatcttcagt atagttgtga aaagtgtagc ggaaatttgt ggtccgagca acagcgtctt       660
tttctagtag tgcggtcggt tacttggttg acattggtat ttggactttg ttgctacacc       720
attcactact tgaagtcgag tgtgaagggt atgatttcta gtggtgaaca cctttagtta       780
cgtaatgttt tcattgctgt tttacttgag atttcgattg agaaaaaggt atttaatagc       840
tcgaatcaat gtgagaacag agagaggatg ttcttcccta actcgaaagg tatatgaggc       900
ttgtgtttct taggagaatt attattcttt tgttatgttg cgcttgtagt tggaaaaggt       960
gaagagacaa aagctggaat tgtgagcgga taacaagctc aacacttgaa atttaggaaa      1020
gagcagaatt tggcaaaaaa aataaaaaaa aaataaacac acatactcat cgagaagctg      1080
t                                                                    1081

<210> SEQ ID NO 9
<211> LENGTH: 20
<212> TYPE: DNA
<213> ORGANISM: Artificial sequence
<220> FEATURE:
<223> OTHER INFORMATION: Primer

<400> SEQUENCE: 9
gagcccacca cctgctcctg                                                    20

<210> SEQ ID NO 10
<211> LENGTH: 25
<212> TYPE: DNA
<213> ORGANISM: Artificial sequence
<220> FEATURE:
<223> OTHER INFORMATION: Primer

<400> SEQUENCE: 10
ctgatgtatt gcgctcctta ctaac                                              25

<210> SEQ ID NO 11
<211> LENGTH: 20
<212> TYPE: DNA

```
<213> ORGANISM: Artificial sequence
<220> FEATURE:
<223> OTHER INFORMATION: Primer

<400> SEQUENCE: 11
cccagatgcg aagttaagtg                                                      20

<210> SEQ ID NO 12
<211> LENGTH: 29
<212> TYPE: DNA
<213> ORGANISM: Artificial sequence
<220> FEATURE:
<223> OTHER INFORMATION: Primer

<400> SEQUENCE: 12
tacaacagat cacgtgatct ttttgtaag                                            29

<210> SEQ ID NO 13
<211> LENGTH: 28
<212> TYPE: DNA
<213> ORGANISM: Artificial sequence
<220> FEATURE:
<223> OTHER INFORMATION: Primer

<400> SEQUENCE: 13
gatttcgtaa ccctattgtt catgaatg                                             28

<210> SEQ ID NO 14
<211> LENGTH: 475
<212> TYPE: DNA
<213> ORGANISM: Artificial sequence
<220> FEATURE:
<223> OTHER INFORMATION: Synthetic polynucleic acid

<400> SEQUENCE: 14
ttctcccttc ttcgaattca gcttgctttt tcattttta ttttccattt ttcagttttt          60
gtttgtgtcg aatttagcca gttgcttctc caagatgaaa aaaaccctg cgcagtttct        120 gtgctgcaag atcctaatcg acttttccac cccccacaaa agtaaatgtt cttttgttac       180
attcgcgtgg gtagctagct ccccgaatct tcaaaggact tagggactgc actacatcag       240
agtgtgttca cctggttgc tgcctggttt gaaagaaaag agcagggaac tcgcgggttc        300
ccggcgaata atcatgcgat agtcctttgg ccttccaagt cgcatgtaga gtagacaaca       360
gacagggagg gcaggaagga tctttcactg agatcctgta tcttgttggg taagtcggat       420
gaaaggggaa tcgtatgaga ttggagagga tgcggaagag gtaacgccctt ttgtt           475

<210> SEQ ID NO 15
<211> LENGTH: 52
<212> TYPE: DNA
<213> ORGANISM: Artificial sequence
<220> FEATURE:
<223> OTHER INFORMATION: Primer

<400> SEQUENCE: 15
tatagggcga attggagctc cgccggcgga agaggtaacg ccttttgtta ac                52

<210> SEQ ID NO 16
<211> LENGTH: 44
<212> TYPE: DNA
<213> ORGANISM: Artificial sequence
<220> FEATURE:
<223> OTHER INFORMATION: Primer

<400> SEQUENCE: 16
```

```
ctaaacggaa ctcgcattta aatctcgttt tcgacactgg atgg          44
```

<210> SEQ ID NO 17
<211> LENGTH: 55
<212> TYPE: DNA
<213> ORGANISM: Artificial sequence
<220> FEATURE:
<223> OTHER INFORMATION: Primer

<400> SEQUENCE: 17

```
gcgagttccg tttagacgcg tttaaacttg tttaattatt atggggcagg cgaga    55
```

<210> SEQ ID NO 18
<211> LENGTH: 40
<212> TYPE: DNA
<213> ORGANISM: Artificial sequence
<220> FEATURE:
<223> OTHER INFORMATION: Primer

<400> SEQUENCE: 18

```
cggggaatgc gctgcttttc gacactggat ggcggcgtta              40
```

<210> SEQ ID NO 19
<211> LENGTH: 43
<212> TYPE: DNA
<213> ORGANISM: Artificial sequence
<220> FEATURE:
<223> OTHER INFORMATION: Primer

<400> SEQUENCE: 19

```
gcagcgcatt ccccgggtac cgctctcgac taggtgatta gcg          43
```

<210> SEQ ID NO 20
<211> LENGTH: 51
<212> TYPE: DNA
<213> ORGANISM: Artificial sequence
<220> FEATURE:
<223> OTHER INFORMATION: Primer

<400> SEQUENCE: 20

```
aaaagctggg taccgggccc actagtcgag agttaaccgt gactacagct a    51
```

<210> SEQ ID NO 21
<211> LENGTH: 11582
<212> TYPE: DNA
<213> ORGANISM: Artificial sequence
<220> FEATURE:
<223> OTHER INFORMATION: Synthetic polynucleic acid

<400> SEQUENCE: 21

```
ggacgcgccc tgtagcggcg cattaagcgc ggcgggtgtg gtggttacgc gcagcgtgac    60
cgctacactt gccagcgccc tagcgcccgc tcctttcgct ttcttccctt cctttctcgc   120
cacgttcgcc ggctttcccc gtcaagctct aaatcggggg ctccctttag ggttccgatt   180
tagtgcttta cggcacctcg accccaaaaa acttgattag ggtgatggtt cacgtagtgg   240
gccatcgccc tgatagacgg ttttttcgccc tttgacgttg gagtccacgt tctttaatag   300
tggactcttg ttccaaactg gaacaacact caacccctatc tcggtctatt cttttgattt   360
ataagggatt ttgccgattt cggcctattg gttaaaaaat gagctgattt aacaaaaatt   420
taacgcgaat tttaacaaaa tattaacgtt tacaatttcg cgccattcgc cattcaggct   480
gcgcaactgt tgggaagggc gatcggtgcg ggcctcttcg ctattacgcc agctggcgaa   540
```

```
aggggggatgt gctgcaaggc gattaagttg ggtaacgcca gggttttccc agtcacgacg    600
ttgtaaaacg acggccagtg aattgtaata cgactcacta tagggcgaat tggagctccg    660
ccggcggaag aggtaacgcc ttttgttaac ttgtttaatt attatggggc aggcgagagg    720
gggaggaatg tatgtgtgtg aggcgggcga gacggagcca tccaggccag gtagaaatag    780
agaaagccga atgttagaca atatggcagc gtagtagagt aggtaggtag gcaagtactg    840
ctagcaaaga ggagaagggt aagctcactc ttcgcattcc acaccgttag tgtgtcagtt    900
tgaacaaaaa aacaatcatc ataccaattg atggactgtg gactggcttt tggaacggct    960
tttcggactg cgattattcg tgaggaatca aggtaggaat ttggtcatat ttacggacaa   1020
cagtgggtga ttcccatatg gagtaggaaa acgagatcat ggtatcctca gatatgttgc   1080
ggaattctgt tcaccgcaaa gttcaggtgt ctctggtggg tttcgttgg tctttgcttt    1140 gcttctccct tgtcttgcat gttaataata gcctagcctg tgagccgaaa cttagggtag   1200
gcttagtgtt ggaacgtaca tatgtatcac gttgacttgg tttaaccagg cgacctggta   1260
gccagccata cccacacacg ttttttgtat cttcagtata gttgtgaaaa gtgtagcgga   1320
aatttgtggt ccgagcaaca gcgtcttttt ctagtagtgc ggtcggttac ttggttgaca   1380
ttggtatttg gactttgttg ctacaccatt cactacttga agtcgagtgt gaagggtatg   1440
atttctagtg gtgaacacct ttagttacgt aatgttttca ttgctgtttt acttgagatt   1500
tcgattgaga aaaggtatt taatagctcg aatcaatgtg agaacagaga gaagatgttc    1560
ttccctaact cgaaaggtat atgaggcttg tgtttcttag gagaattatt attcttttgt   1620
tatgttgcgc ttgtagttgg aaaaggtgaa gagacaaaag ctggaattgt gagcggataa   1680
caagctcaac acttgaaatt taggaaagag cagaatttgg caaaaaaaat aaaaaaaaaa   1740
taaacacaca tactcatcga gaagctgtac cgtcgacggc gcgccgatgt ccaacttaca   1800
agaccaaacc caacaaatcg tccctttat cagatcctta ttaatgccta ctaccggtcc    1860
tgcttctatt cctgatgaca ccttggaaaa acacaccttg agatccgaaa cttcaaccta   1920
taacttgact gtcggtgaca ctggttctgg tttaatcgtt ttcttccctg gttttcctgg   1980
ttcaattgtc ggtgcccact ataccttaca aggtaacggt aactataagt tcgatcaaat   2040
gttgttgacc gcccaaaatt tgcctgcctc ctataactat tgtagattgg tttctagatc   2100
tttaaccgtc agatcatcca ctttgcctgg tggtgtctat gctttgaacg gtacaatcaa   2160
cgctgtcaca tttcaaggtt ccttgtccga attgaccgat gtctcctata acggtttaat   2220
gtccgctact gccaatatca atgacaaaat tggtaacgtc ttagtcggtg aaggtgttac   2280
tgttttgagt ttgccaacct cttatgactt gggttatgtc agattgggtg accctattcc   2340
tgctatcggt ttagacccaa aaatggttgc cacttgtgac tctagtgata gaccaagagt   2400
ctataccatc actgctgccg atgactatca attctcctcc caatatcaac ctggtggtgt   2460
cactatcacc ttgttctctg ccaacatcga cgctataaca tctttgtccg tcggtggtga   2520
attggtattc caaacctccg tccatggttt agtattgggt gccaccatct atttgattgg   2580
tttcgacggt acaaccgtca ttactagagc cgttgctgcc aacaatggtt taaccactgg   2640
tactgacaac ttgatgccat tcaacttggt aatccctacc aacgaaatca cacaaccaat   2700
cacatccatc aaattggaaa ttgtcacctc caaatccggt ggtcaagccg gtgaccaaat   2760
gtcatggagt gctagaggtt cattagccgt aaccatccac ggtggtaact atcctggtgc   2820
cttgagacct gtcactttag tcgcctatga aagagttgct actggttccg tcgttactgt   2880
tgccggtgtt tcaaacttcg aattgatccc aaacccagaa ttggccaaaa acttggttac   2940
```

```
cgaatatggt agattcgacc ctggtgctat gaactataca aaattgatct tatccgaaag   3000
agacagattg ggtatcaaaa ctgtctggcc tactagagaa ataccgact ttagagaata    3060 tttcatggaa gtcgccgact taaattcccc attgaaaatc gccggtgcct ttggttttaa   3120
ggacatcatt agagccatta gaagaatagc cgtctgagcg gccgcctcga ctcagtactg   3180
acaataaaaa gattcttgtt ttcaagaact tgtcatttgt atagttttt tatattgtag    3240 ttgttctatt ttaatcaaat gttagcgtga tttatattt ttttcgcctc gacatcatct    3300
gcccagatgc gaagttaagt gcgcagaaag taatatcatg cgtcaatcgt atgtgaatgc   3360
tggtcgctat actgctgtcg attcgatact aacgccgcca tccagtgtcg aaaacgagat   3420
ttaaatgcga gttccgttta gacgcgttta aacttgttta attattatgg ggcaggcgag   3480
agggggagga atgtatgtgt gtgaggcggg cgagacggag ccatccaggc caggtagaaa   3540
tagagaaagc cgaatgttag acaatatggc agcgtagtag agtaggtagg taggcaagta   3600
ctgctagcaa agaggagaag ggtaagctca ctcttcgcat tccacaccgt tagtgtgtca   3660
gtttgaacaa aaaaacaatc atcataccaa ttgatggact gtggactggc ttttggaacg   3720
gcttttcgga ctgcgattat tcgtgaggaa tcaaggtagg aatttggtca tatttacgga   3780
caacagtggg tgattcccat atggagtagg aaaacgagat catggtatcc tcagatatgt   3840
tgcggaattc tgttcaccgc aaagttcagg gtgctctggt gggtttcggt tggtctttgc   3900
tttgcttctc ccttgtcttg catgttaata atagcctagc ctgtgagccg aaacttaggg   3960
taggcttagt gttggaacgt acatatgtat cacgttgact tggtttaacc aggcgacctg   4020
gtagccagcc atacccacac acgttttttg tatcttcagt atagttgtga aaagtgtagc   4080
ggaaatttgt ggtccgagca acagcgtctt tttctagtag tgcggtcggt tacttggttg   4140
acattggtat ttggactttg ttgctacacc attcactact tgaagtcgag tgtgaagggt   4200
atgatttcta gtggtgaaca cctttagtta cgtaatgttt tcattgctgt tttacttgag   4260
atttcgattg agaaaaaggt atttaatagc tcgaatcaat gtgagaacag agagaagatg   4320
ttcttcccta actcgaaagg tatatgaggc ttgtgtttct taggagaatt attattcttt   4380
tgttatgttg cgcttgtagt tggaaaaggt gaagagacaa aagctggaat tgtgagcgga   4440
taacaagctc aacacttgaa atttaggaaa gagcagaatt tggcaaaaaa aataaaaaaa   4500
aaataaacac acatactcat cgagaagctg taccgtcgac ggcgcgccga tgtccaactt   4560
acaagaccaa acccaacaaa tcgtcccttt tatcagatcc ttattaatgc ctactaccgg   4620
tcctgcttct attcctgatg acaccttgga aaaacacacc ttgagatccg aaacttcaac   4680
ctataacttg actgtcggtg acactggttc tggtttaatc gttttcttcc ctggttttcc   4740
tggttcaatt gtcggtgccc actataccct acaaggtaac ggtaactata agttcgatca   4800
aatgttgttg accgcccaaa atttgcctgc ctcctataac tattgtagat tggtttctag   4860
atctttaacc gtcagatcat ccactttgcc tggtggtgtc tatgctttga acggtacaat   4920
caacgctgtc acatttcaag gttccttgtc cgaattgacc gatgtctcct ataacggttt   4980
aatgtccgct actgccaata tcaatgacaa aattggtaac gtcttagtcg gtgaaggtgt   5040
tactgttttg agtttgccaa cctccttatga cttgggttat gtcagattgg gtgaccctat   5100
tcctgctatc ggtttagacc caaaaatggt tgccacttgt gactctagtg atagaccaag   5160
agtctatacc atcactgctg ccgatgacta tcaattctcc tcccaatatc aacctggtgt   5220
tgtcactatc accttgttct ctgccaacat cgacgctata acatctttgt ccgtcggtgg   5280
```

```
tgaattggta ttccaaacct ccgtccatgg tttagtattg ggtgccacca tctatttgat    5340
tggtttcgac ggtacaaccg tcattactag agccgttgct gccaacaatg gtttaaccac    5400
tggtactgac aacttgatgc cattcaactt ggtaatccct accaacgaaa tcacacaacc    5460
aatcacatcc atcaaattgg aaattgtcac ctccaaatcc ggtggtcaag ccggtgacca    5520
aatgtcatgg agtgctagag gttcattagc cgtaaccatc cacggtggta actatcctgg    5580
tgccttgaga cctgtcactt tagtcgccta tgaaagagtt gctactggtt ccgtcgttac    5640
tgttgccggt gtttcaaact cgaattgat cccaaaccca gaattggcca aaaacttggt     5700
taccgaatat ggtagattcg accctggtgc tatgaactat acaaaattga tcttatccga    5760
aagagacaga ttgggtatca aaactgtctg gcctactaga gaatataccg actttagaga    5820
atatttcatg gaagtcgccg acttaaattc cccattgaaa atcgccggtg cctttggttt    5880
taaggacatc attagagcca ttagaagaat agccgtctga gcggccgcct cgactcagta    5940
ctgacaataa aaagattctt gttttcaaga acttgtcatt tgtatagttt ttttatattg    6000
tagttgttct attttaatca aatgttagcg tgatttatat ttttttttcgc ctcgacatca    6060 tctgcccaga tgcgaagtta agtgcgcaga agtaatatc atgcgtcaat cgtatgtgaa     6120
tgctggtcgc tatactgctg tcgattcgat actaacgccg ccatccagtg tcgaaaagca    6180
gcgcattccc cgggtaccgc tctcgactag gtgattagcg gggggagatg aaaagtgtta    6240
caacgtttgt ctcgcaccct gtaaccttat actattgaac aaaccaacta aacaaaaaa      6300 aaaaactact atcaacaaaa cttcgagctt taacccaagt tatcaattgt ttaaaatgac    6360
tctaaatttc taatacccct tattctttcta ttcttcttct tcttttttaac tatatctact   6420 tatattctat taaatatcac atttacgttt gtattacatg actactcttg tcaaccagga    6480
cgttagtggt cctaacctc aggttcagcc ggctcatagt cttccgaatc gtacattatt      6540
catcgctcgg acctctccat tccgttatttt tatccactct ttgttcctct caattcaaga   6600
attattcact ttaaccactt caacgaaatc aaataaaact ccgtcgaatc agtacagtca    6660
ggaatcacca ccctggacac tcccttccat tgtgtttgtg tttgtgtttg tactttcatt    6720
cattgtccct ttttgacaat ataaaggtta acagagagc tatagtatat cttgggacaa      6780 tgtgattta gtcactttga agtgttatt atttgatcca gtgtacacaa tatctcggca      6840
ggacggcacc atggcttgcc ttattcctga gaatttaagg aacccaaaa aggttcacga      6900 aaatagattg cctactaggg cttactacta tgatcaggat attttcgaat ctctcaatgg    6960
gccttgggct tttgcgttgt tgatgcacc tcttgacgct ccggatgcta agaatttaga     7020
ctgggaaacg gcaagaaat ggagcaccat ttctgtgcca tcccattggg aacttcagga     7080
agactggaag tacggtaaac caatttcac gaacgtacag tacccctatcc caatcgacat   7140 cccaaatcct cccactgtaa atcctactgg tgtttatgct agaacttttg aattagattc    7200
gaaatcgatt gagtcgttcg agcacagatt gagatttgag ggtgtggaca attgttacga    7260
gctttatgtt aatggtcaat atgtgggttt caataagggg tcccgtaacg gggctgaatt    7320
tgatatccaa aagtacgttt ctgagggcga aaacttagtg gtcgtcaagg ttttcaagtg    7380
gtccgattcc acttatatcg aggaccaaga tcaatggtgg ctctctggta tttcagagag   7440
cgtttcttta ctaaaattgc ctaagaaggc ccatattgaa gacgttaggg tcactacaac    7500
ttttgtggac tctcagtatc aggatgcaga gctttctgtg aaagttgatg tccagggttc    7560
ttcttatgat cacatcaatt tcacacttta cgaacctgaa gatggatcta agtttacga     7620 tgcaagctct ttgttgaacg aggagaatgg gaacacgact ttttcaacta aagaatttat    7680
```

```
ttccttctcc accaaaaaga acgaagaaac agctttcaag atcaacgtca aggccccaga    7740
acattggacc gcagaaaatc ctactttgta caagtaccag ttggatttaa ttggatctga    7800
tggcagtgtg attcaatcta ttaagcacca tgttggtttc agacaagtgg agttgaagga    7860
cggtaacatt actgttaatg gcaaagacat tctctttaga ggtgtcaaca gacatgatca    7920
ccatccaagg ttcggtagag ctgtgccatt agattttgtt gttagggact tgattctaat    7980
gaagaagttt aacatcaatg ctgttcgtaa ctcgcattat ccaaaccatc ctaaggtgta    8040
tgacctcttc gataagctgg gcttctgggt cattgacgag gcagatcttg aaactcatgg    8100
tgttcaagag ccatttaatc gtcatacgaa cttggaggct gaatatccag atactaaaaa    8160
taaactctac gatgttaatg cccattactt atcagataat ccagagtacg aggtcgcgta    8220
cttagacaga gcttcccaac ttgtcctaag agatgtcaat catccttcga ttattatctg    8280
gtccttgggt aacgaagctt gttatggcag aaaccacaaa gccatgtaca agttaattaa    8340
acaattggat cctaccagac ttgtgcatta tgagggtgac ttgaacgctt tgagtgcaga    8400
tatctttagt ttcatgtacc aacatttgaa attatggaa aggtggagga agaaccacac     8460
tgatgaaaat ggtaagtttg aaaagccttt gatcttgtgt gagtacgcc atgcaatggg     8520 taacggtcct ggctctttga agaatatca agagttgttc tacaaggaga agttttacca    8580
aggtggcttt atctgggaat gggcaaatca cggtattgaa ttcgaagatg ttagtactgc    8640
agatggtaag ttgcataaag cttatgctta tggtggtgac tttaaggaag aggttcatga    8700
cggagtgttc atcatggatg gtttgtgtaa cagtgagcat aatcctactc cgggccttgt    8760
agagtataag aaggttattg aacccgttca tattaaaatt gcgcacggat ctgtaacaat    8820
cacaaataag cacgacttca ttacgacaga ccacttattg tttatcgaca aggacacggg    8880
aaagacaatc gacgttccat cttaaagcc agaagaatct gttactattc cttctgatac      8940
aacttatgtt gttgccgtgt tgaaagatga tgctggtgtt ctaaaggcag gtcatgaaat    9000
tgcctggggc caagctgaac ttccattgaa ggtacccgat tttgttacag agacagcaga    9060
aaaagctgcg aagatcaacg acggtaaacg ttatgtctca gttgaatcca gtggattgca    9120
ttttatcttg gacaaattgt tgggtaaaat tgaaagccta aaggtcaagg gtaaggaaat    9180
ttccagcaag tttgagggtt cttcaatcac tttctggaga cctccaacga ataatgatga    9240 acctaggga tttaagaact ggaagaagta caatattgat ttaatgaagc aaaacatcca      9300
tggagtgagt gtcgaaaaag gttctaatgg ttctctagct gtagtcacgg ttaactctcg    9360
actagtgggc ccgtaccca gcttttgttc cctttagtga gggttaattc cgagcttggc      9420
gtaatcatgg tcatagctgt ttcctgtgtg aaattgttat ccgctcacaa ttccacacaa    9480
catacgagcc ggaagcataa agtgtaaagc ctggggtgcc taatgagtga gctaactcac    9540
attaattgcg ttgcgctcac tgcccgcttt ccagtcggga aacctgtcgt gccagctgca    9600
ttaatgaatc ggccaacgcg cggggagagg cggtttgcgt attgggcgct cttccgcttc    9660
ctcgctcact gactcgctgc gctcggtcgt tcggctgcgg cgagcggtat cagctcactc    9720
aaaggcggta atacggttat ccacagaatc aggggataac gcaggaaaga acatgtgagc    9780
aaaaggccag caaaaggcca ggaaccgtaa aaaggccgcg ttgctggcgt ttttccatag    9840
gctccgcccc cctgacgagc atcacaaaaa tcgacgctca agtcagaggt ggcgaaaccc    9900
gacaggacta taaagatacc aggcgtttcc ccctggaagc tccctcgtgc gctctcctgt    9960
tccgaccctg ccgcttaccg gatacctgtc cgcctttctc ccttcgggaa gcgtggcgct   10020
```

```
ttctcatagc tcacgctgta ggtatctcag ttcggtgtag gtcgttcgct ccaagctggg    10080
ctgtgtgcac gaaccccccg ttcagcccga ccgctgcgcc ttatccggta actatcgtct    10140
tgagtccaac ccggtaagac acgacttatc gccactggca gcagccactg gtaacaggat    10200
tagcagagcg aggtatgtag gcggtgctac agagttcttg aagtggtggc ctaactacgg    10260
ctacactaga aggacagtat ttggtatctg cgctctgctg aagccagtta ccttcggaaa    10320
aagagttggt agctcttgat ccggcaaaca accaccgct ggtagcggtg ttttttttgt      10380
ttgcaagcag cagattacgc gcagaaaaaa aggatctcaa gaagatcctt tgatcttttc    10440
tacggggtct gacgctcagt ggaacgaaaa ctcacgttaa gggattttgg tcatgagatt    10500
atcaaaaagg atcttcacct agatcctttt aaattaaaaa tgaagtttta aatcaatcta    10560
aagtatatat gagtaaactt ggtctgacag ttaccaatgc ttaatcagtg aggcaccctat   10620 ctcagcgatc tgtctatttc gttcatccat agttgcctga ctccccgtcg tgtagataac    10680
tacgatacgg gagggcttac catctggccc cagtgctgca atgataccgc gagacccacg    10740
ctcaccggct ccagatttat cagcaataaa ccagccagcc ggaagggccg agcgcagaag    10800
tggtcctgca actttatccg cctccatcca gtctattaat tgttgccggg aagctagagt    10860
aagtagttcg ccagttaata gtttgcgcaa cgttgttgcc attgctacag gcatcgtggt    10920
gtcacgctcg tcgtttggta tggcttcatt cagctccggt tcccaacgat caaggcgagt    10980
tacatgatcc cccatgttgt gcaaaaaagc ggttagctcc ttcggtcctc cgatcgttgt    11040
cagaagtaag ttggccgcag tgttatcact catggttatg gcagcactgc ataattctct    11100
tactgtcatg ccatccgtaa gatgcttttc tgtgactggt gagtactcaa ccaagtcatt    11160
ctgagaatag tgtatgcggc gaccgagttg ctcttgcccg gcgtcaatac gggataatac    11220
cgcgccacat agcagaactt taaaagtgct catcattgga aaacgttctt cggggcgaaa    11280
actctcaagg atcttaccgc tgttgagatc cagttcgatg taacccactc gtgcacccaa    11340
ctgatcttca gcatctttta ctttcaccag cgtttctggg tgagcaaaaa caggaaggca    11400
aaatgccgca aaaaagggaa taagggcgac acggaaatgt tgaatactca tactcttcct    11460
ttttcaatat tattgaagca tttatcaggg ttattgtctc atgagcggat acatatttga    11520
atgtatttag aaaaataaac aaataggggt tccgcgcaca tttccccgaa aagtgccacc    11580
tg                                                                    11582
```

```
<210> SEQ ID NO 22
<211> LENGTH: 29
<212> TYPE: DNA
<213> ORGANISM: Artificial sequence
<220> FEATURE:
<223> OTHER INFORMATION: Primer

<400> SEQUENCE: 22
gacatcactg tctcttcccc ttaatgatc                                           29

<210> SEQ ID NO 23
<211> LENGTH: 29
<212> TYPE: DNA
<213> ORGANISM: Artificial sequence
<220> FEATURE:
<223> OTHER INFORMATION: Primer

<400> SEQUENCE: 23
tcagcaagca tcaataatcc ccttggttc                                           29
```

```
<210> SEQ ID NO 24
<211> LENGTH: 28
<212> TYPE: DNA
<213> ORGANISM: Artificial sequence
<220> FEATURE:
<223> OTHER INFORMATION: Primer

<400> SEQUENCE: 24
gaaagaaaga cgttggtctc tacgcttg                                    28

<210> SEQ ID NO 25
<211> LENGTH: 29
<212> TYPE: DNA
<213> ORGANISM: Artificial sequence
<220> FEATURE:
<223> OTHER INFORMATION: Primer

<400> SEQUENCE: 25
agattataag ttcctggggc tttacccac                                   29
```

OPTIMIZED HOST/VECTOR SYSTEM FOR PRODUCING PROTECTIVE MONO- AND MULTIVALENT SUBUNIT VACCINES ON THE BASIS OF THE YEAST *KLUYVEROMYCES LACTIS*

CROSS-REFERENCE TO RELATED APPLICATIONS

This is the U.S. National Stage of International Patent Application No. PCT/DE2018/000379 filed on Dec. 19, 2018, which in turn claims the benefit of German Patent Application No. 10 2017 012 109.5 filed on Dec. 27, 2017.

FIELD OF THE INVENTION

The invention relates to recombinant *Kluyveromyces lactis* (*K. lactis*) yeasts which are fit for highly efficient expression of one or more foreign proteins and are suitable for use as vaccine for the generation of a protective immune response against pathogens. The invention provides in particular *K. lactis* strains for targeted cloning of foreign antigen-encoding nucleic acids into the yeast genome of the *K. lactis* strain, which is characterized in that the *K. lactis* strain has integrated expression cassettes for foreign antigens at the KlURA3-20 locus (KLLA0E22771g) and/or at the KlMET5-1 locus (KLLA0B03938g) as an alternative or in addition to the KlLAC4 locus. The invention furthermore relates to integrative expression vectors and methods for generating the *K. lactis* strains of the invention and to the use thereof as vaccines.

BACKGROUND OF THE INVENTION

Vaccines are used for preventing diseases (preventive vaccines) or for treating established diseases (immunotherapeutic vaccines). In the last 100 years or so, preventive vaccination programs have substantially contributed to reducing infectious diseases. Immunotherapeutic vaccines, for instance against persistent infections with viruses, bacteria or parasites or against carcinogenic diseases, have only been developed and used for about 20 years. The goal of vaccination is the induction of a cellular (i.e., essentially T cell and NK cell-mediated) and/or humoral (i.e., essentially B cell/antibody-mediated) immune response and of an immunological memory against antigenic components of pathogens or malignant (tumorigenic) cells.

Classic vaccines contain the entire pathogen in attenuated (inactivated) or killed form, including the genetic material thereof, i.e., nucleic acids in the form of DNA or RNA. To be produced, said classic vaccines usually require special safety precautions and/or the use of infectable organisms and/or of cell cultures; moreover, said vaccines often require storage and transport that is complex and involves the use of cold chains. In addition, the use of classic vaccines involves the danger of substances from the production process (e.g., from the test animal or from the cell culture) causing adverse effects in the vaccinated individual or of the pathogen being undesirably reactivated. Problems exist in diagnostics too: for example, in the case of the vaccination of useful animals with complete pathogens, vaccinated animals cannot be differentiated from naturally infected animals, meaning that early warning systems based on the detection of new infections are unusable. So-called "subunit vaccines", which only vaccinate with defined components of the pathogen, were therefore developed. A prerequisite for the use thereof is that "major antigens" of the pathogen in question are known.

Major antigens are usually surface constituents of the pathogen that can be recognized by the immune system, for example proteins of a viral shell or of a viral capsid. In the absence of a complete virus particle, said major antigens can also induce a humoral and/or cellular immune response and an immunological memory in the host against the virus. Since further constituents of the pathogen are missing in "subunit vaccination", vaccinated individuals can be differentiated from naturally infected individuals by a differential diagnosis (Differentiating Infected from Vaccinated Animals (DIVA)); accordingly, reference is also made to a "subunit marker vaccine". Disadvantages of many subunit vaccines are an often complex production process and an often inadequate immunogenicity: whereas the pathogens themselves can be cultured efficiently (with the above-stated limitations), the major antigens thereof must be produced by gene technology by means of cost-intensive and usually inefficient methods and purified in a complex manner. Subunit vaccines thus obtained are accordingly biological material which has a short shelf life and must often be stored and transported in a cool state. For these reasons, most mass vaccines for useful animals are still based on the classic principle, which uses complete pathogens.

For example, the widespread poultry disease infectious bursal disease (IBD) is triggered by the infectious bursal disease virus (IBDV), a nonenveloped virus having a double-stranded, segmented RNA genome from the Birnaviridae family. Most vaccines against IBD are based on attenuated (weakened) or inactivated viruses. However, the problem that arises here is that, although highly attenuated non-inactivated "live viruses" and also inactivated viruses offer protection against IBD viruses of average pathogenicity, this is not the case for very virulent IBD virus strains (vvIBDV). Until recently, very virulent, attenuated viruses (intermediate hot strains) were protective against vvIBDV—these vaccine strains have, however, adverse effects in the form of the possible occurrence of immunosuppression due to transient damage to the B cells in the *Bursa fabricii*, a lymphatic organ (Rautenschlein et al. (2005)). However, even said intermediate hot vaccines do not offer complete protection against recently discovered vvIBDV strains (Negash et al. (2012); Kasanga et al. (2007)). Moreover, a problem of vaccination with highly attenuated live viruses is that maternal antibodies prevent virus replication and hence the induction of an immune response. Therefore, an effective vaccination with these vaccines is only possible three weeks after hatching (Kumar et al. (2000); Rautenschlein et al. (2005)).

For example, influenza A viruses are among the most important virus pathogens worldwide (Short et al. (2015); Silva et al. (2012)). Influenza viruses belong to the Orthomyxoviridae family; they are enveloped viruses having single-stranded, segmented RNA as the genome. Like most RNA viruses, influenza viruses are also subject to a high mutation rate. Especially the reassortment of viral RNA segments gives rise to viral descendants having new genetic and biological properties (Short et al. (2015)). Owing to the rapid evolution, the problem that arises in particular in the case of vaccinations against influenza viruses is that existing vaccines do not "catch hold" in the case of newly emerged virus variants. Accordingly, attempts have already been made for a long time to develop vaccines which exhibit cross-protection and hence also long-term protection against different influenza variants (Steel et al. (2010); Krammer and Palese (2013); Kirchenbaum and Ross (2014); Berthoud et al. (2011)).

The bovine viral diarrhea virus (BVDV) is a widespread pathogen of even-toed ungulates. BVDV is a member of the Pestivirus genus of the Flaviviridae family. The single-stranded RNA genome of these viruses is likewise subject to a high mutation rate. Moreover, in the case of pregnant animals, the fetus can become infected, and persistently infected (PI) animals are then born owing to the immunotolerance. Said PI animals spread the virus further and can, in the case of 100% virus mutation, die from so-called mucosal disease. Here too, attempts have already been made for a long time to develop vaccines which exhibit cross-protection and long-term protection against different BVD virus variants (Ridpath (2015)).

Effective subunit vaccines can address or solve these problems. In most cases, subunits are protein components of pathogens; they can be produced by gene technology in various host cells. Besides the gut bacterium *Escherichia coli*, mammalian cells or insect cells that can be propagated in cell cultures, plant cells and various fungi have been established as host systems for heterologous protein expression. Microbial systems such as bacteria and fungi can be cultivated particularly cost-effectively on a large scale.

Yeast cells of the yeast genera *Saccharomyces, Pichia* and *Kluyveromyces* have already been used routinely for decades for expressing foreign proteins. In contrast to bacteria, yeast cells have the advantage that they are eukaryotes, i.e., they resemble animal cells in many aspects, and eukaryotic proteins, i.e., proteins which are formed in animal cells and/or must be functional, can be produced cost-effectively in yeasts in native or virtually native form (Bathurst (1994); Gellissen & Hollenberg (1997)). Yeasts were initially only used for producing the foreign proteins; after expression, the proteins were purified from the yeast cells and used as subunit vaccines. Attempts have only recently been made to administer yeasts themselves or cell fractions of the yeasts as vaccines. “Yeast-based vaccines” are accordingly yeast particles which contain immunologically effective components of pathogens (antigens) and which, after administration (e.g., subcutaneous, intramuscular or oral/mucosal), can trigger in the host organism a specific immune response against said antigens and hence also against the pathogen from which said antigens originate. What is desired is induction in the vaccinated organisms of an immunological “memory” which, in the event of a subsequent infection (“challenge”), prevents multiplication and/or spreading of the corresponding pathogens and/or reduces the pathological effects of the infection. As already addressed above, the antigens are usually structural proteins of the pathogen, the encoding nucleic acid sequences (antigen-encoding genes) of which are introduced into yeast cells using gene-technology methods and allow the expression of one or more of such structural proteins. The thus generated recombinant yeasts in live form (yeast cells), in powder form after killing and drying (yeast particles) or after cell disruption and homogenization (yeast lysate) are yeast-based vaccines. After administration of the vaccines, the antigens are recognized by the immune system and cause a humoral and/or cellular immune defense.

Yeast-based vaccination is known to a person skilled in the art from the prior art. A range of US patent applications and patents, for example US 20090304741 A1, U.S. Pat. Nos. 5,830,463 A, 7,465,454 B2 and US 20070166323 A1, describe the use of *Saccharomyces cerevisiae* (*S. cerevisiae*) strains containing at least one recombinant antigen in immunotherapy. It was shown that these yeasts are effective for stimulating an immune reaction, especially a cell-mediated immune reaction.

WO 2006044923 discloses yeasts (*S. cerevisiae*) which recombinantly express various proteins of the hepatitis C virus (HCV) and which can trigger an immune reaction, especially a T cell response, against said HCV proteins and are intended to be used as vaccine against chronic hepatitis C.

WO 2007092792 describes the possible use of recombinant *S. cerevisiae* yeasts against influenza virus infections, involving use of a combination of various yeast strains, the administration of which leads to an induction of T cells, i.e., to a cellular immune response.

WO 20101054649 and WO 2013107436 describe the use of strains of the species *Kluyveromyces lactis* containing defined antigens for generating a protective humoral immune response following oral/mucosal or subcutaneous administration of entire killed yeast cells. The last-mentioned patents contain application examples in which recombinant *K. lactis* strains derived from the starting strain VAK367-D4 were successfully used for vaccination.

The possibility of using recombinant *Kluyveromyces lactis* yeasts for vaccination is known to a person skilled in the art from the prior art: (Arnold et al. (2012)); WO 20101054649 and WO 2013107436). Application examples were able to show that the subcutaneous administration of the yeast *K. lactis* expressing the VP2 capsid protein of the infectious bursal disease virus (IBDV) intracellularly via an expression cassette controlled by the LAC4 promoter triggers a humoral immune response which gives effective protection against virus infection. It was possible to show this for an IBD virus of average pathogenicity, but it has so far not been possible to show this against very virulent IBDV (vvIBDV). Earlier data showed that the effectiveness of a yeast vaccine can be increased by increasing the intracellular concentration of the viral antigen (Arnold et al. (2012)). A technical variant for achieving an increase in antigen concentration consists in introducing an additional copy of the transcription activator gene KIGAL4-1 (alias LAC9-1) into the IBDV-VP2-expressing strain (deposited strains DSM 25406 and DSM 25407) by means of integration of the pLI-1 plasmid (Krijger et al. (2012) and WO 2013107436). The generation of such *K. lactis* vaccine strains was thus hitherto based on two genetic interventions: firstly, on the integration of the antigen-encoding foreign gene and, secondly, on the integration of the KIGAL4-1 gene. However, in the hitherto practiced form, the latter regularly also led to integration of tandem repeats of the plasmid, resulting not only in cytotoxic effects owing to the strong overexpression of the activator (Breunig 1989), but also in differing copy numbers for the KIGAL4-1 and ScURA3 genes in vaccine strains generated in this manner.

The strategy of performing the expression of the foreign gene via an unmodified LAC4 promoter, as described in the abovementioned application examples (Arnold et al. (2012); WO 20101054649 and WO 2013107436), has the secondary effect that a minimal expression of the foreign gene occurs even under noninducing conditions, i.e., the promoter is open to a certain extent. When the KIGAL4-1 gene dose is increased, this effect is much more pronounced once more. Accordingly, in the case of proteins having a cytopathic effect (CPE) on the yeast cell in the case of heterologous expression, biomass formation during cultivation, for example during a fed-batch fermentation process, can be severely limited. Specifically for these cases, alternative ways which minimize gene expression under noninducing conditions must be found.

Various subunit vaccines are only effectively effective when not just one, but multiple subunits of a pathogen are used for vaccination. Moreover, the use of multiple antigen subunits in vaccination can strongly increase cross-protectivity against different variants of a pathogen. The coexpression of the same or of different antigens can also be used to reincrease the antigen concentration in the yeast cell or to generate a vaccine which protects against different pathogens.

The above-discussed strains are generally auxotrophic strains which frequently grow more poorly in complete medium than prototrophic strains. Accordingly, a rapidly performable conversion of auxotrophic yeast strains into a prototrophic form can lead to improved growth properties.

DESCRIPTION OF THE INVENTION

The object of the invention was, then, to provide new *K. lactis* vaccine strains which can overcome the disadvantages of the prior art. In particular, what should be provided are recombinant *K. lactis* strains containing a limited copy number of the KlGAL4-1 gene, integrated at a defined site in the genome. Moreover, what should be provided are strains which allow only slight expression of foreign protein or none under noninduced conditions, allow the expression of multiple copies of an antigen or the expression of multiple antigens in a yeast, which are better suited to cultivation and are usable more effectively for protective vaccination against pathogens. At the same time, heterologous genes encoding immunomodulatorily active proteins (antigens) should be integrated at defined sites of the *K. lactis* genome. In the case of selection of the searched clones having integration of foreign genes, no resistance genes should be used as selection markers. Moreover, prototrophic strains should be generated from auxotrophic strains via a simplest possible method. This should also allow the simplified fermentation of the generated yeast vaccine strains in non-supplemented, synthetic medium.

These objects were achieved by providing a modular system which contains new vectors and new, genetically modified variants of the yeast *K. lactis* and which allows the generation of vaccine strains optimized for the specific properties of the protein antigens. Via a building block-type exchange of DNA elements between the vectors, an efficient, routine cloning of foreign antigen-encoding regions into the yeast genome was achieved, independent of the foreign gene to be expressed. As a result of the targeted genomic integration of the relevant foreign genes, the yeast strains are stable over very many generations and genetically exactly defined. Owing to these properties, fermentation processes proceed reproducibly under nonselective conditions and can be standardized. The optimization of the *K. lactis* yeasts according to the invention consisted in controlling the protein production rate such that it is as high as possible, but such that it is below a threshold at which cytopathic effects of the antigens severely interfere with the efficient fermentation process. This was achieved by a genetic intervention or by a combination of multiple genetic interventions:
  i. the increase in the concentration of the lactose-inducible transcription activator,
  ii. the targeted modification of the LAC4 promoter, and/or
  iii. the step-by-step increase in the gene dose for the antigen-encoding foreign gene.

Furthermore, the optimization of the *K. lactis* yeasts according to the invention consisted in:
  iv. establishing multiple, new integration sites for foreign gene-encoding cassettes in the yeast genome in order to be able to express multiple antigens simultaneously.

In a preferred embodiment, the object of the invention is achieved by providing a *K. lactis* strain for targeted cloning of foreign gene-encoding nucleic acids into the yeast genome of the *K. lactis* strain, characterized in that the *K. lactis* strain has integrated expression cassettes for foreign antigens at the KlURA3-20 locus (KLLA0E22771g) and/or at the KlMET5-1 locus (KLLA0B03938g) as an alternative or in addition to the KlLAC4 locus. It is particularly preferred when the *K. lactis* strain has integrated expression cassettes for foreign antigens at the KlURA3-20 locus (KLLA0E22771g) and/or at the KlMET5-1 locus (KLLA0B03938g) in addition to the KlLAC4 locus. It is very particularly preferred when the *K. lactis* strain has integrated expression cassettes for foreign antigens at the KlURA3-20 locus (KLLA0E22771g) and at the KlMET5-1 locus (KLLA0B03938g) in addition to the KlLAC4 locus. Such modified *K. lactis* strains have the advantage that genes for the expression of foreign genes are integrated at specified, defined loci in the *K. lactis* genome and the copy number of the foreign genes is controllable. Furthermore, said *K. lactis* strains allow the integration of different genes for the expression of different foreign antigens at defined loci in the *K. lactis* genome.

"Foreign antigens" or "foreign proteins" in the context of this invention mean all peptides, polypeptides and proteins which are suitable for generating an immune response, preferably a protective immune response, in humans or in an animal against a pathogen or carcinogenically degenerated cells. Foreign proteins can originate from pathogens or tumors of any kind, for which antigens which are solely capable of inducing a protective immune response, preferably a protective immune response, have been characterized.

In a preferred embodiment, the foreign proteins originate from pathogens (viruses, bacteria, parasites), for which antigens which are solely capable of inducing a protective immune response, preferably a protective humoral immune response, have been characterized.

For example, these are:

Foreign Proteins Originating from Parasites

*Necator americanus*; *Ancylostoma duodenale*: ASP protein, hemoglobin-degrading proteases

*Leishmania*: gp63, 46 kD promastigote antigen, LACK

*Plasmodium*: CSP protein, CSA-1, CSA-3, EXP1, SSP2, STARP, SALSA, MSP1, MSP2, MSP3, AMA-1, GLURP, Pfs25, Pfs 28, Pvs25, Pvs 28, Pfs 48/45, Pfs 230

*Schistosoma*: TP1, Sm23, ShGSTs 26 and 28, paramyosin, parasite myosin, Sm14

Foreign Proteins Originating from Bacteria

*Mycobakterium tuberculosis*: Ag85A, Hsp65, R8307, 19 kD, 45 kD, 10.4

*Heliobacter pylori*: VacA, LagA, NAP, hsp, urease, catalase

Group A *Streptococcus*: M, SCPA peptidase, exotoxins SPEA and SPEC, fibronectin binding protein

*Streptococcus pneumonia*: PspA, PsaA, BHV 3, BHV 4

*Salmonella typhimurium*: Vi antigen

*Shigella*: LPS

*Vibrio cholera*: CTB

*Escherichia coli* ETEC: LT, LT-ST, CTB

*Yersinia pestis*: F1, V

Foreign Proteins Originating from Tumor Cells/Tumors (Tumor-Associated Antigens, TAA)
  CEA
  5T4
  MUC1
  MART1
  HER-2

Foreign proteins originating from viruses are especially preferred.
  Caliciviridae (Norwalk, HEV): NV 60 kD; HEV ORF2
  Reoviridae (Rota): VP7, VP4
  Retroviridae (HIV): Gag, Pol, Nef, Env, gp160, gp120, gp140, gp41
  Flaviviridae (genus Flavivirus: WNV, Dengue, YF, TBE, JEV): preM-Env, NS3, NS4, NS5
  Flaviviridae (genus Pestivirus BVDV, CSFV, BDV; genus Hepacivirus HCV): E1, E2, $E^{RNS}$ (Pesti), C, NS3, NS4, NS5
  Hepadnaviridae (HBV): HBS antigen
  Paramyxoviridae (Paramyxovirinae: PIV-1, PIV-2, mumps, Sendai, PIV-2, PIV-4, Morbilli): M, HN, N, F
  Paramyxoviridae (Pneumovirinae: RSV): F, G, SH, M
  Rhabdoviridae (Rabies): G
  Herpesviridae (EBV, HSV2): gp350/220 (EBV), gB2, gD2 (HSV)
  Coronaviridae (SARS): CoV, N, M, S
  Orthomyxoviridae (Influenza A, B): HA, NA, M1, M2, NP
  Papillomaviridae: L2, E6, E7

In a further embodiment of the invention, the modified *K. lactis* strains are characterized in that the expression cassettes contain the *K. lactis* LAC4-12 promoter ($P_{LAC4-12}$) or variants of said promoter, the ORF of the antigen to be expressed and the AgTEF1 terminator. Said embodiment has the advantage that the expression of foreign genes under the control of the $P_{LAC4-12}$ promoter are induced approximately equally strongly by lactose after integration at the LAC4 and/or KIURA3 and/or KIMET5 locus.

As described above, there is a positive correlation between the antigen concentration in vaccine strains and the immunogenic effect of the yeast vaccine in the target organism. To prevent a CPE in the case of excessively strong overexpression, for example due to integration of an additional KIGAL4 gene, the above-described vector system can alternatively be modified in order to rapidly and efficiently connect multiple gene copies in series and to introduce this expression cassette in one step at one of the three gene loci (see Example 5 and FIG. 7A).

In an advantageous further development of the invention, the modified *K. lactis* strains therefore contain at the KILAC4 locus or at the KIURA3-20 locus or at the KIMET5-1 locus multiple copies of a foreign antigen-encoding nucleic acid sequence that are inserted via tandem expression cassettes or multi-expression cassettes. Said expression cassettes comprise multiple copies of the antigen-encoding regions (genes) flanked in each case by the LAC4-12 promoter ($P_{LAC4-12}$) or variants of said promoter and the AgTEF1 terminator. Duplication of the gene copies of the antigen that is performed in this way can significantly increase the expression thereof via one of the respective gene loci.

In a preferred embodiment of the invention, the gene of the foreign antigen IBDV-VP2 is present in the form of a tandem expression cassette at the locus KILAC4 of the *K. lactis* strain. Said *K. lactis* strain has, compared with strains having a single copy of the gene encoding the foreign antigen IBDV-VP2, the advantage that the foreign antigen IBDV-VP2 is expressed with increased quantity. Particular preference according to this embodiment of the invention is given to the strain VAK1118 (DSM 32701), which has the gene of the foreign antigen IBDV-VP2 in the form of a tandem expression cassette at the locus KILAC4.

It is furthermore preferred when one or more copies of different foreign antigen-encoding nucleic acids are inserted via single expression cassettes, tandem expression cassettes or multi-expression cassettes at the KILAC4 locus and/or at the KIURA3-20 locus and/or at the KIMET5-1 locus of the *K. lactis* strains according to the invention. As a result, it is possible to express, firstly, different foreign antigens and, secondly, said different foreign antigens in different concentrations in the yeast cell. Particular preference according to this embodiment is given to a *K. lactis* strain in which the encoding nucleic acid sequences of the foreign antigens influenza A HA (A/Puerto Rico/8/1934(H1N1)) and influenza A M1 (A/Puerto Rico/8/1934(H1N1)) are inserted at the KILAC4 and KIURA3-20 loci of the *K. lactis* strain and are expressed. Special preference according to this embodiment of the invention is given the strain VAK1283 (DSM 32697), in which the encoding nucleic acid sequences of the foreign antigens influenza A HA (A/Puerto Rico/8/1934 (H1N1)) and influenza A M1 (A/Puerto Rico/8/1934 (H1N1)) are inserted at the KILAC4 and KIURA3-20 loci of the *K. lactis* strain.

As mentioned, it is known that the increase in the KIGAL4 gene dose can lead to raising of antigen production (Krijger et al. 2012 and WO 2013107436). The disadvantages of achieving this via the integration of the KIGAL4-expressing pLI-1 plasmid in a two-step process are stated above. Said disadvantages were overcome according to the invention by providing a stable starting strain for the integration of foreign genes that contains a second copy of the KIGAL4 gene. This ensures that all derived strains have the same genetic background and that exactly one additional KIGAL4 gene copy is present in said strains. This decreases the cytotoxicity which has been observed in the case of expression of multiple copies and reduces the steps in vaccine strain production to just one step. In addition, genetic stability is increased, since the reversible integration/excision of the plasmid is omitted. Such a strain can, for example, be produced as described in Example 1.

In a further advantageous embodiment of the invention, what is thus provided is a *K. lactis* strain which contains, in addition to the genomic KIGAL4 gene, additionally a second ectopic copy of the KIGAL4 gene. In said strain, the expression of the KIGAL4 transcription activator can be maximally increased two-fold and the expression of the foreign genes inserted into the KILAC4 locus and/or the KIURA3-20 locus and/or the KIMET5-1 locus can be increased in a defined manner via the LAC4-12 promoter or via below-described variants of said promoter. In conventional practice, plasmids encoding KIGAL4 were introduced into the cell transiently and in a multiple, uncontrolled copy number. As a result, the foreign antigen was often expressed in such a high concentration that this led to cytotoxic effects. In the case of the *K. lactis* strains of this embodiment of the invention, cytotoxic effects can be reduced or avoided with a high degree of effectiveness. Further gene loci which will be developed in the future for the same purpose (insertion of a LAC4-controlled expression cassette) can also be controlled in this way. It has been found to be advantageous when the ectopic copy of the KIGAL4 gene, which is flanked by the KIGAL4 promoter and KIGAL4 terminator, is integrated in the *K. lactis* strain at the gene locus KLLA0E13795g (Klavt3::KIGAL4-1, SEQ ID No.: 1). Special preference according to this embodiment of the invention is given to the strain VAK1111 (DSM 32696), which has these properties.

In a further preferred embodiment, the invention provides a K. lactis strain in which the encoding nucleic acid sequence of the foreign antigen IBDV-VP2 is present at the locus KlLAC4. Special preference according to this embodiment of the invention is given to the strain VAK1171 (DSM 32699). Said strain additionally contains a second, ectopic copy of the KlGAL4 gene, at which the encoding nucleic acid sequence of the foreign antigen IBDV-VP2 is likewise present. Said strain exhibits an increased expression of the foreign antigen IBDV-VP2 compared to strains without additional ectopic copy of the KlGAL4 gene.

Heterologous protein production in microorganisms is problematic when this leads to a cytopathic effect (CPE). The invention therefore provides a way to decouple the antigen production phase from the biomass accumulation phase. Owing to the inducible LAC4 promoter, this is partially possible by a fed-batch fermentation process for example, but is hampered because the promoter $P_{LAC4-12}$ is not completely closed down under noninducing conditions (i.e., open to a certain extent). In the case of antigens having a very strong CPE, what occurs as a result is a reduction in the growth rate and an induction of the cellular stress response, with disadvantageous effects for antigen production. This problem is aggravated by the doubling of the KlGAL4 gene dose and/or the increase in the number of antigen-encoding sequences (see below).

An advantageous further development of the *K. lactis* strains according to the invention therefore consists in the *K. lactis* strains having a modified promoter structure of the LAC4-12 promoter that allows only slight foreign protein expression or none under noninducing conditions. The modified structure of the LAC4-12 promoter is especially characterized in that the basal control region (BCR) of the promoter $P_{LAC4\text{-}12}$ between positions 1065 and 1540 (LR2 deletion; $P_{LAC4\text{-}12\text{-}LR2}$; SEQ ID No.: 2) is deleted (see also Example 2). As already described above, this embodiment of the invention has the advantage, compared to conventional practice, that cytotoxic effects conventionally caused by excessively strong expression of the foreign genes are reduced or avoided with a high degree of effectiveness. Preference according to this embodiment is given to *K. lactis* strains in which the encoding nucleic acid sequence of the foreign antigen influenza A HA (A/Puerto Rico/8/1934 (H1N1)) is present at the locus KlLAC4. Special preference according to this embodiment of the invention is given to the strain VAK1243 (DSM 32702). Said strain contains an LR2 deletion in the LAC4-12 promoter.

The *K. lactis* strain can also have a modified structure of the LAC4-12 promoter that allows modulation of foreign protein expression, wherein the number of binding sites for the activator KlGal4 of the promoter ("upstream activating sequences" 1, 2 and 4, 5) varies and 1, 2, 3 or 4 KlGal4-binding sites are present. In this way, it is possible to express different foreign proteins in differing concentration (quality by design) in a yeast cell. The shortened promoter variants are, inter a/ia, important for the modularity of the system in order, for example, to express proteins in the same strain in optimal stoichiometric ratios, for example for the formation of highly immunogenic virus-like particles (VLPs). It is preferred according to this embodiment of the invention when the encoding nucleic acid sequence of the foreign antigen IBDV-VP2 is inserted at the locus K/LAC4 of the *K. lactis* strain. Special preference according to this embodiment of the invention is given to the strain VAK1131 (DSM 32700). Said strain contains an LR2 deletion and a deletion of the upstream activating sequences 4 and 5 in the LAC4-12 promoter.

Part of the object of the invention was to provide *K. lactis* strains which are better suited to cultivation. This problem is solved by restoring the gene function of the alleles Kllac4, Klura3-20 and Klmet5-1 in the *K. lactis* strains according to the invention. The resultant *K. lactis* strains are prototrophic (Example 6, FIG. 8). The fermentation of the vaccine strains is thus simplified, and the establishment of the production processes is facilitated and made more cost-efficient. Preference according to this embodiment of the invention is given to *K. lactis* strains in which the encoding nucleic acid sequences of the foreign antigens BVDV E2 ectodomain (type 1, CP7), BVDV E2 ectodomain (type 2, New York 93) and BVDV Npro-NS3 (type 1, CP7) are inserted into the at the loci KlLAC4, KlURA3-20 and KlMet5-1 of the *K. lactis* strain. Special preference according to this embodiment of the invention is given to the strain VAK1400 (DSM 32698). Said strain is prototrophic.

In a particularly preferred embodiment, the invention provides a *K. lactis* strain selected from the strains VAK952 DSM 32705;
VAK1111 DSM 32696;
VAK1118 DSM 32701;
VAK1131 DSM 32700;
VAK 1171 DSM 32699;
VAK1243 DSM 32702;
VAK1283 DSM 32697;
VAK1395 DSM 32706;
VAK1400 DSM 32698

Said strains were deposited on Nov. 24, 2017 or Dec. 1, 2017 (DSM 32705, DSM 32706) at the *Deutsche Sammlung von Mikroorganismen und Zellkulturen GmbH* [German Collection of Microorganisms and Cell Cultures GmbH], DSMZ, Inhoffenstrasse 7B, 38124 Braunschweig, Germany, in accordance with the Budapest Treaty under the above-specified numbers.

In a further aspect, the invention provides integrative expression vectors, with the aid of which the *K. lactis* strains of the invention are producible.

In a preferred embodiment, the invention provides the integrative expression vectors KlpURA3 (SEQ ID No.: 3) and KlpMET5 (SEQ ID No.: 4). Said vectors contain the LAC4-12 promoter ($P_{LAC4\text{-}12}$) or variants of said promoter (as described above for the *K. lactis* strains) including the ORF of the antigen to be expressed, additionally the AgTEF1 terminator sequence and also targeting sequences which allow a targeted restoration of the functionality of the Klura3-20 and Klmet5-1 alleles after integration. The antigen-encoding sequence is cloned between the promoter sequence and terminator sequence of the expression cassette via defined restriction sites. By means of said vectors, foreign gene-expressing cassettes are integrated into the *K. lactis* genome in a stable manner, without markers and without use of antibiotic resistances. Accordingly, the strengths of this vector system are that foreign genes are easily exchangeable between the different vectors and that promoters and terminators of the expression cassettes are replaceable with others. The expression cassette consists of the $P_{LAC4\text{-}12}$ promoter and the AgTEF1 terminator, and also the foreign gene in between. The foreign gene can be exchanged via the restriction sites AscI and NotI. The $P_{LAC4\text{-}12}$ promoter can be replaced via the restriction sites SmaI and AscI in both vectors, and the terminator can be replaced via NotI and BoxI (or MluI) in KlpURA3 and via NotI and Ecl136II (or SacI) in KlpMET5. Alternative expression cassettes are cloned between the restriction sites SmaI and BoxI (or MluI) in KlpURA3, and between SmaI and Ecl136II (or SacI) in KlpMET5. Using the stated restriction enzymes, the expression cassettes are also exchanged between KlpMET5 and KlpURA3 vectors or additional expression cassettes are introduced. An improvement over the Klp3 and Klp3-MCS vectors (WO 20101054649) is that selection is carried out under noninducing conditions (without lactose), and this leads to higher transformation rates in the case of proteins with CPE and prevents a possible enrichment of transformants with reduced foreign gene expression. See also Examples 3.1 and 3.2.

In a particularly preferred embodiment of the invention, an integrative expression vector selected from KlpMET5-$P_{LAC4-12}$-Et, KlpMET5-$P_{LAC4-12-LR2}$-Et, KlpMET5-$P_{LAC4}$-Et, KlpMET5-$P_{LAC4-LR2}$ and from KlpURA3-$P_{LAC4-12}$-Et, KlpURA3-$P_{LAC4-12-LR2}$-Et, KlpURA3-$P_{LAC4}$-Et and KlpURA3-$P_{LAC4-LR2}$ (SEQ ID No.: 3 or SEQ ID No. 4 in combination with SEQ ID No.: 5, 6, 7 or 8) is provided.

The vectors KlpURA3-$P_{LAC4-12}$-Et, KlpURA3-$P_{LAC4-12-LR2}$-Et, KlpURA3-$P_{LAC4}$-Et and KlpURA3-$P_{LAC4-LR2}$ are variants of the vector KlpURA3-Et, into which the encoding nucleic acid sequence for the Etx.B-HA protein is inserted in each case. The vectors KlpURA3-$P_{LAC4-12}$-Et, KlpURA3-$P_{LAC4-12-LR2}$-Et, KlpURA3-$P_{LAC4}$-Et and KlpURA3-$P_{LAC4-LR2}$ have differences in the promoter compared to the vector KlpURA3-Et.

The vectors KlpMET5-$P_{LAC4-12}$-Et, KlpMET5-$P_{LAC4-12-LR2}$-Et, KlpMET5-$P_{LAC4}$-Et, KlpMET5-$P_{LAC4-LR2}$ are variants of the vector KlpMET5, into which the encoding nucleic acid sequence for the Etx.B-HA protein is inserted in each case. The vectors KlpMET5-$P_{LAC4-12}$-Et, KlpMET5-$P_{LAC4-12-LR2}$-Et, KlpMET5-$P_{LAC4}$-Et, KlpMET5-$P_{LAC4-LR2}$ have differences in the promoter compared to the vector KlpMET5.

In a further aspect, the invention provides a method for producing a *K. lactis* strain according to the invention, comprising the steps of:
(i) inserting the encoding nucleic acid sequence of the desired antigen into the KlpURA3 or KlpMET5 vector,
(ii) transforming a *K. lactis* culture with the modified and previously enzymatically digested vector construct,
(iii) selecting transformed *K. lactis* cells with the aid of a solid medium which does not contain uracil or/and methionine, and
(iv) optionally: restoring prototrophy.

In one embodiment of the method according to the invention, the gene sequences of multiple antigens can be inserted ectopically at the same time and expressed in a regulated manner. It is preferred when different gene sequences encoding antigens of different variants of a pathogen are inserted ectopically and expressed in a regulated manner. Furthermore, it is preferred when different gene sequences encoding antigens of different pathogens are inserted ectopically and expressed in a regulated manner.

In a further aspect, the invention provides pharmaceutical or veterinary-medicine compositions for parenteral, enteral, intramuscular, mucosal or oral administration, containing a *K. lactis* strain according to the invention, optionally in combination with customary vehicles and/or excipients. In particular, the invention provides pharmaceutical or veterinary-medicine compositions suitable for vaccination.

Preferably, the pharmaceutical or veterinary-medicine composition comprises at least one physiologically compatible vehicle, diluent, adjuvant and/or excipient. The *K. lactis* strains according to the present invention can be contained in a pharmaceutically compatible vehicle, for example in a conventional medium, such as an aqueous saline medium or a buffer solution as pharmaceutical composition for injection. Such a medium can also contain conventional pharmaceutical substances, such as, for example, pharmaceutically compatible salts for setting the osmotic pressure, buffers, preservatives and the like. The preferred media include physiological saline solution and human serum. A particularly preferred medium is PBS-buffered saline solution.

Further suitable pharmaceutically compatible vehicles are known to a person skilled in the art from, for example, Remington's Practice of Pharmacy, 13th edition and J. of Pharmaceutical Science & Technology, Vol. 52, No. 5, September-October, pages 238-311.

A further aspect of the invention provides for the use of the recombinant *K. lactis* yeasts according to the invention for vaccination, such as, for example, for generating a protective immunization, especially a protective immunization directed against a pathogen.

A corresponding method for generating a protective immunization comprises, for example, the following steps:
a) cultivating and propagating the recombinant yeasts according to the invention,
b) harvesting and inactivating the yeasts,
c) administering the recombinant yeasts according to an immunization scheme to be defined,
d) determining the titer of the antibodies formed and/or
e) detecting the immunization.

The cultivation and propagation of the recombinant yeasts according to the invention can be achieved using any conventionally available method. Particular preference is given to methods which lead to high cell yields in a cost-effective manner. These include fermentation methods, especially high-cell-density fermentation methods. Carrying out the fermentation using a fed-batch fermentation protocol has been found to be particularly advantageous.

In a preferred embodiment, the protective immunization is achieved in that the recombinant yeasts are administered orally/mucosally, intramuscularly or subcutaneously.

The recombinant yeast cells should be used in an inactivated/killed state in the method according to the invention. To this end, the yeasts are dried after cultivation and expression of the foreign genes and subsequently inactivated. The inactivation can be carried out using any conventionally available method. Particularly suitable for use in the method according to the invention are heat inactivation (e.g., heat inactivation for 2 hours at 90° C.) or γ-irradiation (e.g., with 25 or 50 kGy).

The invention also provides a method for vaccination, comprising administering a *K. lactis* strain according to the invention to a subject, for example an animal or a human, preferably an animal, in an amount sufficient for triggering an immune response, preferably a protective immune response against one or more foreign antigens, in the subject.

A particular advantage is that, using the *K. lactis* strains according to the invention, a protective immune response against one pathogen is triggered solely after a single application/immunization ("one shot") or after a double application/immunization ("prime-boost"). What has been found to be a further advantage is that, using the *K. lactis* strains according to the invention, a cross-protective immune response against different variants of a pathogen can be triggered after a single application/immunization ("one shot") or after a double application/immunization ("prime-boost"). If the *K. lactis* strains according to the invention bear and express different foreign genes against antigens of different pathogens, it is even possible to trigger a protective immune response against different pathogens after a single application/immunization ("one shot") or in a double application/immunization ("prime-boost").

SUMMARY OF THE ADVANTAGES OF THE INVENTION

The described improvements in the *K. lactis* platform result in numerous advantages:
a. A great simplification (ready to use toolbox/kit) and a high reproducibility in the construction of strains of "subunit vaccines" based on yeast is made possible. They can now be generated within a defined, short time span.
b. The yeast vaccines can contain one or more antigens; they can be customized in a flexible manner and produced in different quantities.
c. Moreover, an efficient fermentation of the prototrophic yeasts is made possible.
d. A stringent inducibility of recombinant protein production is made possible. The latter is particularly important for proteins which can trigger a CPE.
e. The targeted, stable, genomic integration of the foreign genes and the associated genetic stability of the strains offers the advantage that production processes proceed reproducibly. This is particularly important for GMP production.
f. The protectivity of the yeast vaccine is improved with the increase in recombinant antigen production that is achieved as a result of an increase in foreign gene copies and/or in KIGAL4 concentration.
g. In addition, the vaccine dose to be administered can be reduced with the increase in recombinant antigen production that is achieved as a result of an increase in foreign gene copies and/or in KIGAL4 concentration. Yeast production is thereby more cost-efficient and the compatibility of the vaccine for the vaccine recipient is improved.
h. Multivalent yeast vaccines can be used in a cross-protective or multivalent protective manner for prophylaxis against different variants of the same pathogen or against different pathogens. Apart from inactivation and admixing with an adequate adjuvant and/or a suitable liquid volume, no further downstream processing of the yeast for use as vaccine is required.

The invention is more particularly elucidated below on the basis of the drawings and exemplary embodiments.

FIG. 1 shows the characterization of a newly generated *K. lactis* background strain having two KIGAL4 copies. The presence of the second ectopic KIGAL4 copy at the identified integration site was checked and the effect of the integration on yeast growth was analyzed. A: Diagram of the integration site of the ectopic KIGAL4 copy. The integration site is indicated and the gene names are given. B: Agarose gel of PCR-amplified fragments, using the primers VK183 (5'-GAGCCCACCACCTGCTCCTG-3') (SEQ ID No.: 9) and VK184 (5'-CTGATGTATTGCGCTCCTTACTAAC-3') (SEQ ID No.: 10), of the KIAVT3 locus of a yeast strain with (VAK1110) and without (VAK367) an additionally integrated, ectopic KIGAL4 gene. The respectively expected fragment sizes are given on the right in the diagram. C: Drop test with serial tenfold dilutions (Start-OD 1) on glucose (YPD) or lactose (YPLac). The incubation was carried out at and 37° C. in each case. The growth of yeast strains having a KIGAL4 copy at the native gene locus (VAK1139), at the ectopic gene locus and deleted KIGAL4 at the native gene locus (VAK1110), having no KIGAL4 copy (ΔKIgal4; VAK964) or having two KIGAL4 copies (VAK1168) were compared. What is shown is that the defined integration of a further KIGAL4 gene only leads to marginal growth defects: said defects are only visible at 37° C. and under inducing conditions. What is clearer is the growth defect in the case of complete deletion of KIGAL4.

Figure 2:
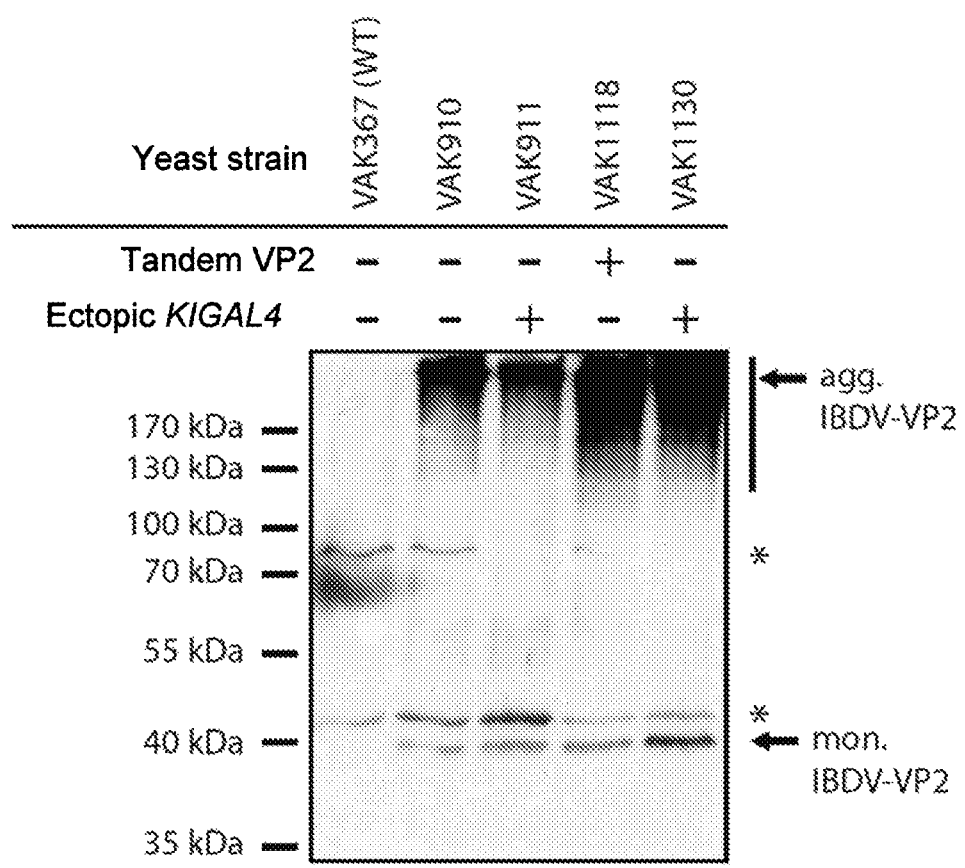

FIG. 2 shows the western blot analysis with proteins of an IBDV-VP2-producing *K. lactis* strain having an additional, ectopic KIGAL4 copy. The effect of an additional KIGAL4 copy on the LAC4-12 promoter-dependent recombinant protein production was analyzed by Western blotting. The test strain used was a yeast strain having an IBDV-VP2 expression cassette, which yeast strain was compared with other IBDV-VP2 yeast strains. The presence (+) or absence (−) of an ectopic KIGAL4 copy and of a tandem IBDV-VP2 expression cassette (see below) are indicated above. In strain VAK911, the ectopic copy was introduced by linearization of the plasmid pLI-1 by means of BstEII (Krijger et al. 2012 and WO 2013107436), and in strain VAK1130, the ectopic KIGAL4 copy was at the KIAVT3 locus (see FIG. 1). Yeast strain VAK367 was included as wild-type control without a foreign gene. The yeast strains were cultivated in YPLac for 15 h after a preliminary culture in YPD. 20 μg in each case of the protein extract were analyzed per yeast strain by means of SDS-PAGE. The immunoblotting was carried out using anti-IBDV rabbit serum (1:8000) and HRP-conjugated anti-rabbit antibody from goat (1:10 000). Multimeric (agg.) and monomeric (mon.) IBDV-VP2 are indicated on the right by arrows, nonspecific bands by asterisks. What is shown is that the ectopic expression of an additional KIGAL4 gene leads to a strong increase in foreign antigen concentration, as does the presence of a tandem expression cassette (see also below).

Figure 3:
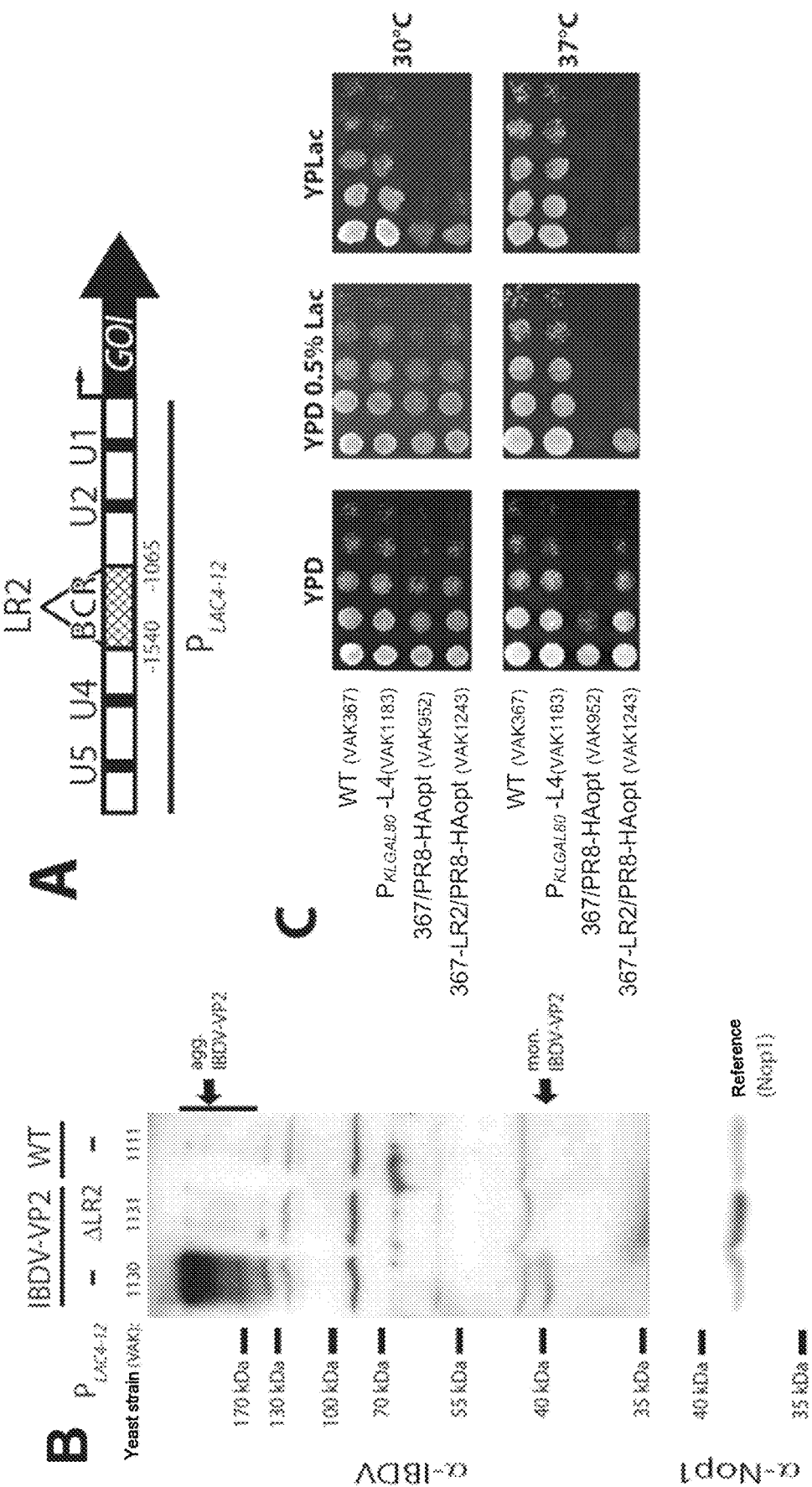

FIG. 3 illustrates the effect of LR2 deletion in the LAC4-12 promoter on noninduced, recombinant protein production and on yeast growth on glucose. The unmodified LAC4-12 promoter also exhibits a basal expression of the GOI (gene of interest) under noninducing conditions. This is particularly problematic in the case of cytotoxically acting foreign antigens. What was tested with these experiments was whether a deletion in the BC region (LR2 deletion) of the LAC4-12 promoter can reduce or even completely suppress recombinant protein production under noninducing conditions. A: Diagram of a LAC4-12 promoter ($P_{LAC4-12}$). The basal control region (BCR), the LR2 deletion and the four KIGal4-binding sites (upstream activating sequence: U1, U2, U4, U5) and also the encoding nucleic acid sequence of the foreign gene (GOI) are drawn in. B: Western blotting of IBDV-VP2 yeast strains, with (VAK1131) and without (VAK1130) LR2 deletion, after cultivation under noninducing conditions (YP 3% EtOH). VAK1111 was used as wild-type control without a foreign gene. For each yeast strain, 50 μg of protein extract were loaded onto a 12% SDS gel. The immunoblotting was carried out using anti-IBDV rabbit serum (1:5000) and HRP-conjugated anti-rabbit antibody from goat (1:10 000). The loading control KlNop1 was detected using mouse anti-Nop1 antibody (1:5000) and HRP-conjugated anti-mouse antibody from goat (1:10 000). C: Drop test with serial tenfold dilutions (Start-OD 1) on YPD, YPD containing 0.5% glucose and YPLac. The incubation was carried out at 30° C. and 37° C. in each case. The growth of the yeast strains bearing an influenza A HA foreign gene at the LAC4 locus, with (VAK1243) and without (VAK952) LR2 deletion, was compared. The yeast strain VAK367 was used as wild-type controls without a foreign gene. What is shown is that the LR2 deletion prevents the unwanted, basal foreign protein expression. Furthermore, what is shown is that the LR2 deletion improves the growth of a yeast strain expressing a cytotoxic protein (influenza hemagglutinin, HA), both under noninducing conditions and under inducing conditions. This is particularly clear at 37° C.

Figure 4:
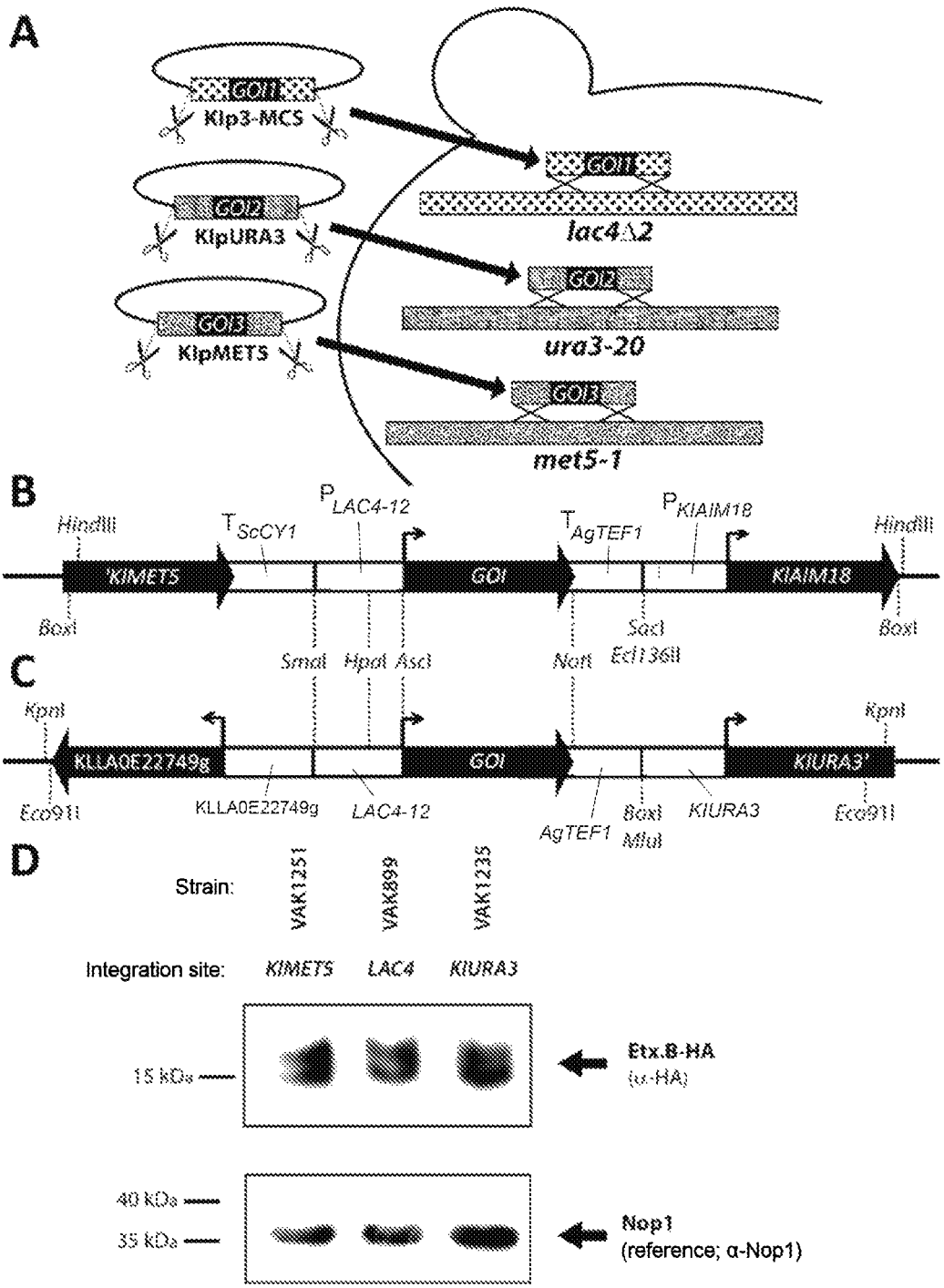

FIG. 4 shows the K/p vectors which can be used for integrating protein expression cassettes into different loci of the *K. lactis* genome. Whereas the use of the LAC4 locus (Klp3 vector system) has already been described (WO 20101054649 and WO 2013107436), the use of the KlURA3 and KlMET5 loci is new. A: Diagram of the different Klp vectors with their respective integration site in the genome. B & C: Expression cassettes and flanking ends in the KlpURA3 (B) and KlpMET5 (C) vectors that are newly described here. The different DNA sequence segments and relevant restriction sites are indicated. GOI: foreign gene (gene of interest). D: Western blotting analysis of foreign protein expression in yeast strains constructed with the aid of the Klp vectors (A, B & C). Here, the foreign gene is Etx.B-HA. The yeast 'house-keeping' KlNop1 protein (KLLA0C04389g) was detected as loading control. The yeast strains were cultivated in YPLac (+U) for 4 h after a preliminary culture in YPD (+U). For each yeast strain, 30 µg of protein extract were loaded onto a 12% SDS-PAGE. The immunoblotting was carried out using monoclonal mouse anti-HA (1:5000) and anti-KlNop1 (1:5000; Santa Cruz, TX, USA) antibodies and also HRP-conjugated anti-mouse antibody from goat (1:10 000; Jackson ImmunoResearch, PA, USA). What is shown is that, similarly to the LAC4 locus (WO 20101054649 and WO 2013107436), both KlURA3 and KlMET5 loci are usable for heterologous gene expression.

Figure 5:
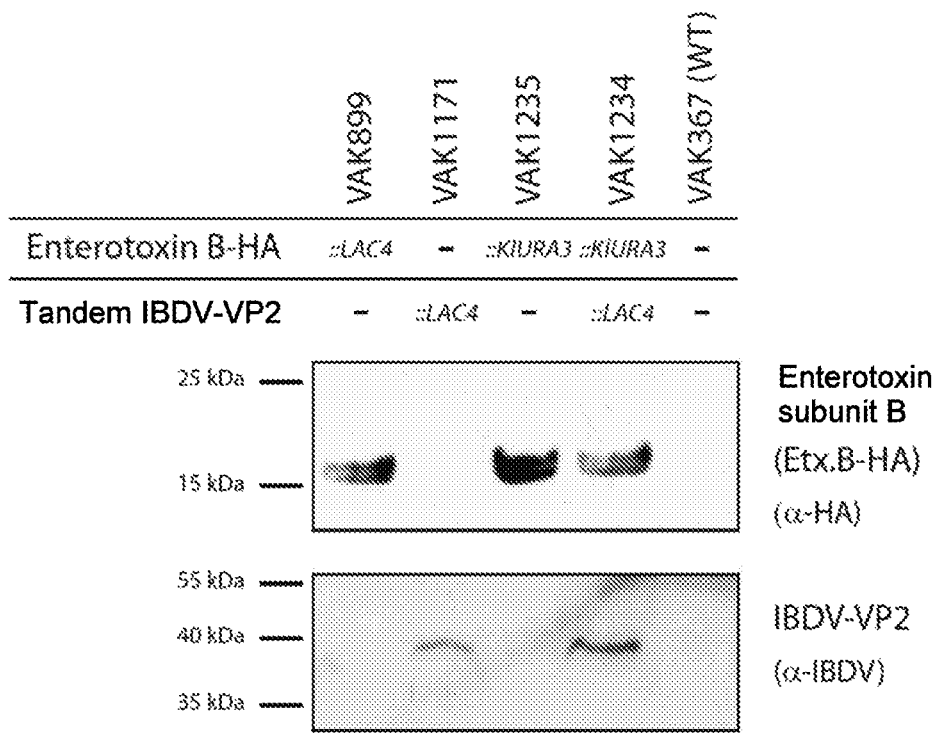

FIG. 5 shows the production of different, recombinant proteins in the same yeast strain. Said yeast strain (VAK1234) was constructed using the KlpURA3 and Klp3-MCS vectors. Western blotting analysis with proteins of a tandem IBDV VP2-expressing yeast strain (see below) into which an additional expression cassette, with Etx.B-HA as foreign gene, was introduced with the aid of the KlpURA3 vector (VAK1234). The controls used were yeast strains bearing only the expression cassette with Etx.B-HA at the LAC4 (VAK899) or KlURA3 locus (VAK1235) or only the tandem IBDV-VP2 expression cassette at the LAC4 locus (VAK1171) in the genome. The yeast strains were cultivated in YPLac for 6 h after a preliminary culture in YPD. For each yeast strain, 30 µg of protein extract were loaded onto a 12% SDS-PAGE. The detection of the proteins in the immunoblot was carried out using mouse anti-HA antibody (1:5000; Santa Cruz, TX, USA) and HRP-conjugated anti-mouse antibody from goat (1:10 000) for Etx.B-HA and using rabbit anti-IBDV antiserum (1:5000; Granzow et al. (1997)) and HRP-conjugated anti-rabbit antibody from goat (1:10 000; Jackson ImmunoResearch, PA, USA) for IBDV-VP2. What is shown is that both foreign proteins are expressed in the same yeast cell. Surprisingly, the expression level of one antigen is not limited upon coexpression of another antigen. This is clear in the comparison of the expression levels in monovalent and bivalent strains (see also FIG. 12).

Figure 6:
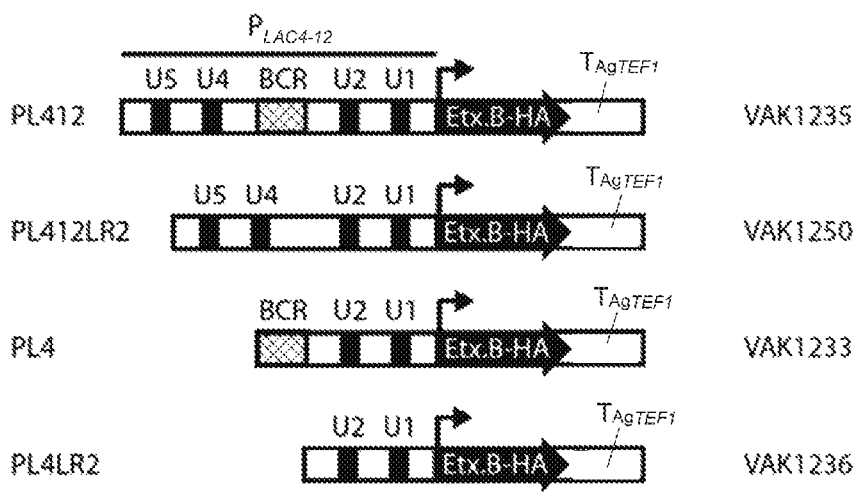
Figure 6:
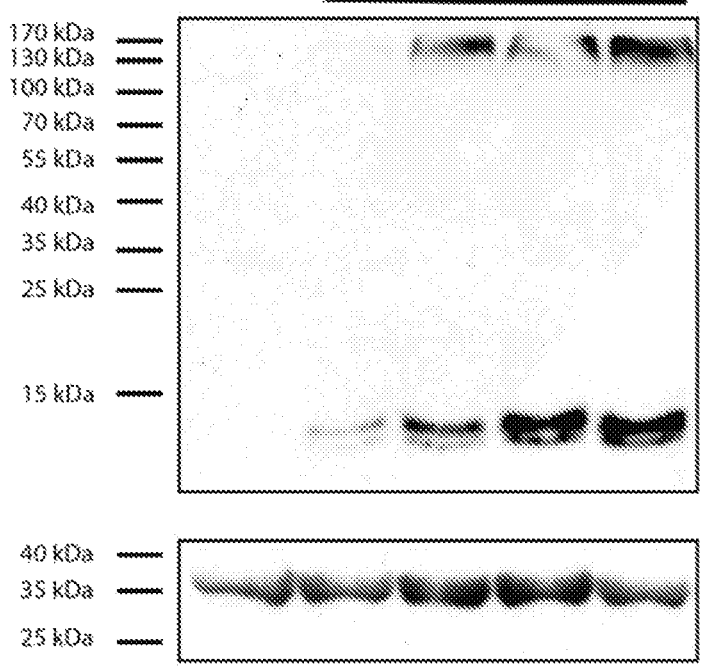

FIG. 6 shows the differently induced LAC4-12 promoter variants for expression cassettes in Klp vectors. The expression cassettes of the Klp vectors were provided with different variants of the LAC4-12 promoter. The effect of the promoter variants on the strength of induction of protein synthesis was tested on the basis of the analysis of yeast strains containing the corresponding expression cassettes with Etx.B-HA as foreign gene. A: Schematic representation of the promoter variant, the associated KlpURA3 vectors with Etx.B-HA as foreign gene and the yeast strains created therefrom. BCR: binding region of the transcription activators KlCat8 and KlSip4, transcription activators under noninducing conditions; U1, U2, U4, U5: binding regions for the transcription activator KlGal4 (upstream activating sequence). B: Western blotting analysis for characterizing the LAC4-12 promoter variants in the yeast strains created using the KlpURA3 vector (A). The yeast strains were cultivated in YPLac for 4 h after a preliminary culture in YPD. For each yeast strain, 30 lag of protein extract were loaded onto a 12% SDS-PAGE. The immunoblotting was carried out using monoclonal mouse anti-HA (1:5000) and anti-Nop1 (1:5000) antibody and also HRP-conjugated anti-mouse antibody from goat (1:10 000). What is shown is that the expression rate of the foreign gene varies depending on the nature of the promoter used.

Figure 7:
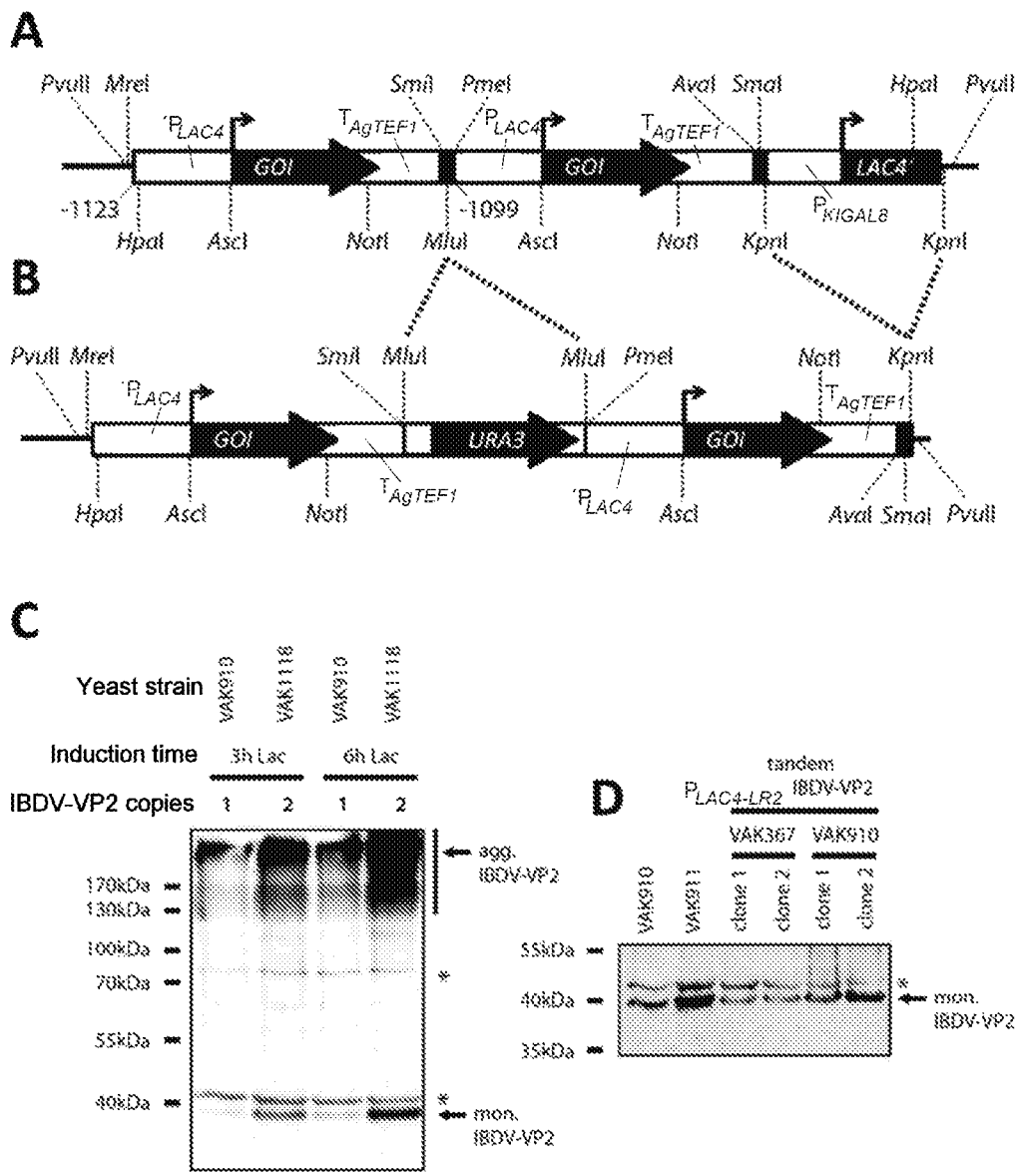

FIG. 7 shows the effect of doubling the number of foreign gene copies by means of a tandem expression cassette on recombinant protein production. The effect on recombinant protein production (IBDV-VP2) by increasing the number of foreign gene copies by means of a tandem expression cassette was tested. A: Schematic representation of the tandem expression cassette. DNA segments and relevant restriction sites are indicated. GOI: foreign gene (gene of interest). B: The tandem construct derived from (A) for random integration with the aid of an ScURA3 selection marker is depicted. C: Western blotting analysis for comparing IBDV-VP2 protein production in a yeast strain (VAK1118) having a tandem expression cassette (A) and a yeast strain (VAK910) having an expression cassette containing only one foreign gene copy. The yeast strains were cultivated in YPLac for 3 h or 6 h after a preliminary culture in YPD. For each yeast strain, 60 lag of protein extract were loaded onto a 12% SDS-PAGE. The immunoblotting was carried out using anti-IBDV rabbit serum (1:10 000) and HRP-conjugated anti-rabbit antibody from goat (1:10 000). Aggregated (agg.) and monomeric (mon.) IBDV-VP2 are indicated on the right by arrows, nonspecific bands by asterisks. D: Western analysis of yeast strains having a randomly integrated tandem IBDV-VP2 expression cassette (B) in comparison with a Klp3-MCS-generated yeast strain having one expression cassette (VAK910) and also the yeast strain derived therefrom having additional KlGAL4-1 copies (pLI-1). The yeast strains were cultivated in YPLac for 8 h after a preliminary culture in YPD. The immunoblotting was carried out as described under (b). What is shown is that the use of a tandem expression cassette significantly increases the foreign protein expression rate.

Figure 8:
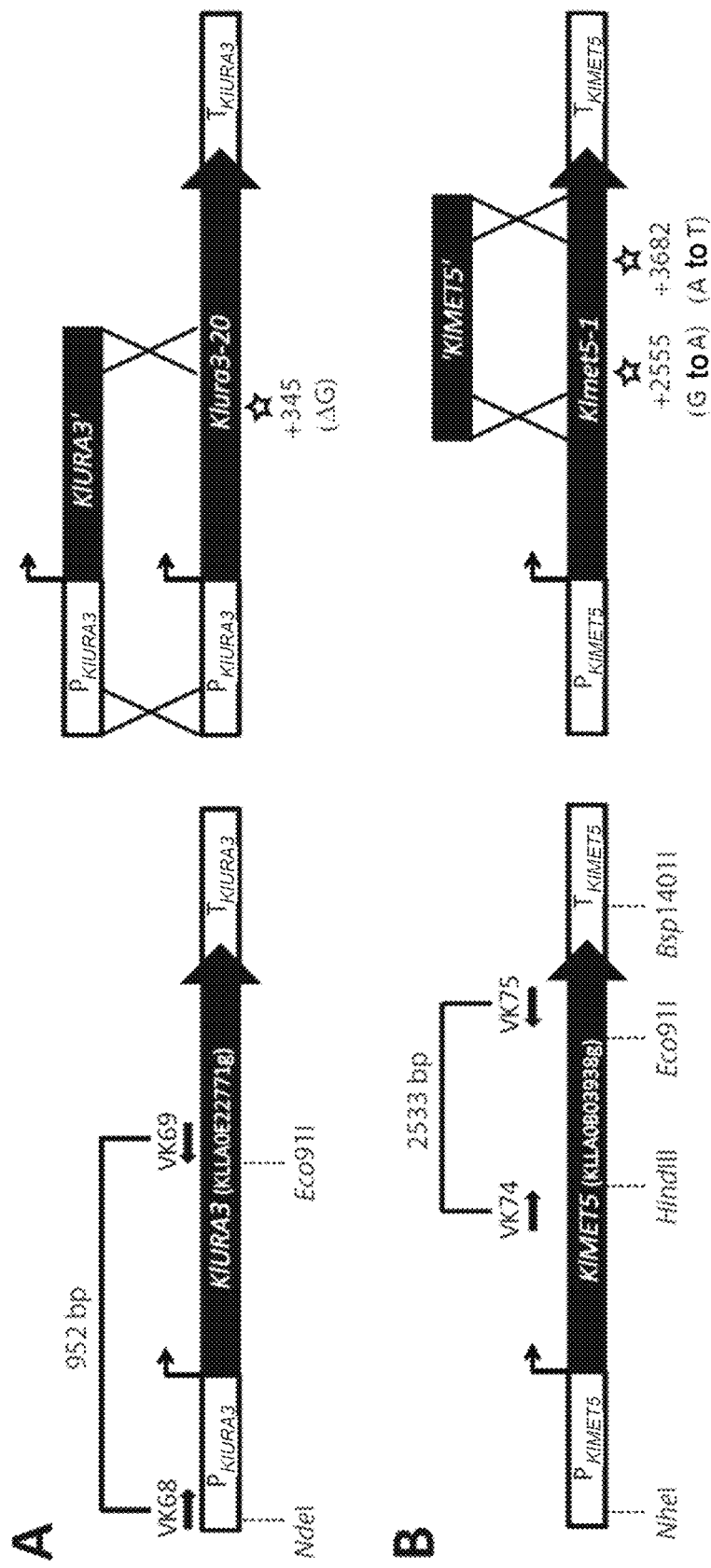

FIG. 8 shows the gene fragments for restoring the gene function of the alleles Klura3-20 and Klmet5-1 (A). Schematically depicted are the gene loci and the gene fragments, amplified using the specified primers, for KlURA3 (A) and KlMET5 (B). The mutations of the alleles Klura3-20 (A) and Klmet5-1 (B) reconstituted with these gene fragments by homologous recombination are shown as stars below the genes. The restriction sites with which the subcloned fragments are cut out are drawn in. This diagram illustrates the strategy of generating prototrophic foreign gene-expressing yeast strains at the URA3 or METS locus.

Figure 9:
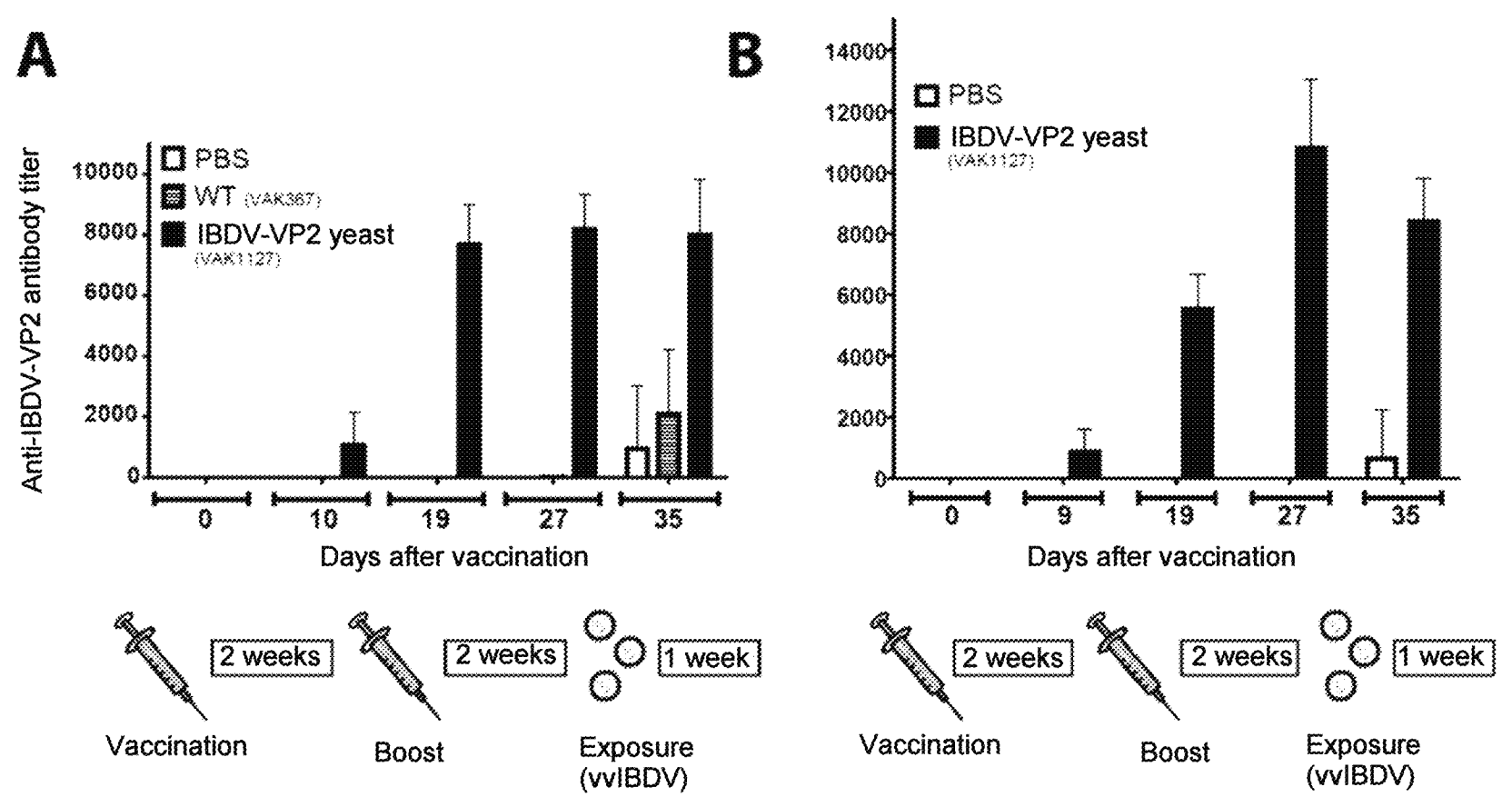

FIG. 9 illustrates, in combination with Table 1 and Table 2, the protective immunization of chickens against vvIBDV in a classic prime-boost vaccination scheme. In two experiments (A and B), groups of at least 16 SPF chickens were vaccinated subcutaneously according to a prime-boost method with lyophilized and heat-inactivated yeast cells of the genetically optimized tandem IBDV-VP2 *K. lactis* yeast strain VAK1127. The first vaccination took place two weeks after hatching (prime), and the second (boost) two weeks after that. Two weeks after the boost, a virus challenge with a vvIBDV strain (very virulent 89163/7.3) was effected. One subject group serving as infection control was subjected to a mock treatment in which only PBS or adjuvant was administered. In experiment 1 (A), the wild-type yeast (VAK367) was also administered as control. At least seven chickens per group served as control without virus challenge, and at least five in experiment 2 (B). Sera were obtained just before the first administration, before and after the challenge, and otherwise at ten-day intervals. The strength of seroconversion was determined by means of ELISA (ProFLOK IBD Plus, Synbiotics). The converted titers according to the kit information are shown. A: Experiment 2 was performed in the same way as experiment 1 (A). The mean value of the ELISA titers from 12 animals is shown with standard deviation. Both experiments show a strong development of titers of anti-IBDV VP2 antibodies in the case of the VAK1127-vaccinated animals. The associated tables summarize the results of the protection of the vaccinated animals against challenge with the vvIBDV: in both vaccination experiments, it was possible to achieve complete protection against the viral infection.

Figure 10:
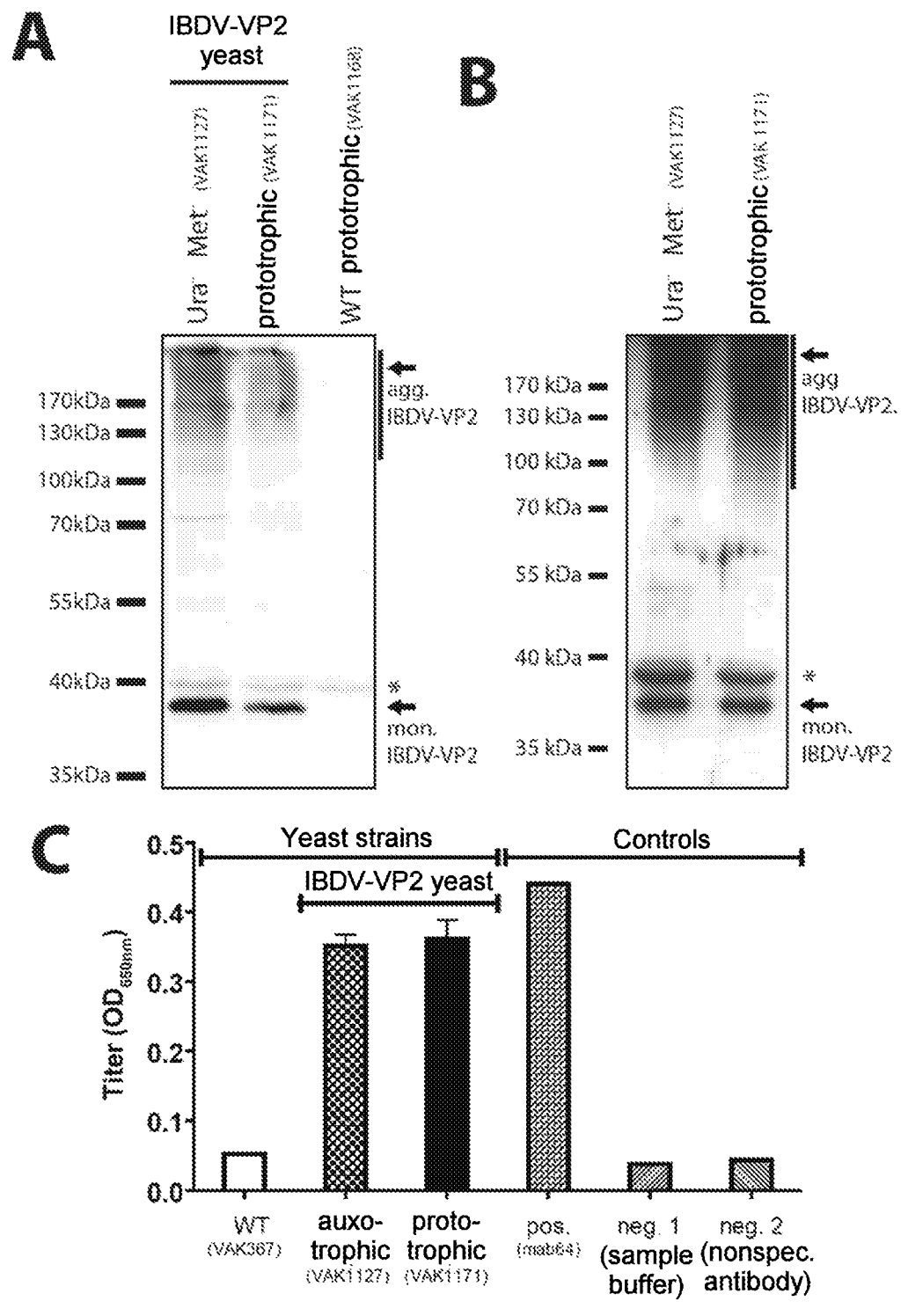

FIG. 10 shows the effect of the genetic modifications for restoring prototrophy on the amount of recombinant protein production and immunogenicity of a tandem IBDV-VP2 yeast strain. The auxotrophic tandem IBDV-VP2 yeast strain VAK1127 and the prototrophic yeast strain VAK1171 derived therefrom were compared with regard to efficiency of recombinant protein production and immunogenicity. A: Western blotting analysis for ascertaining the IBDV-VP2 content in freshly harvested yeast material. The yeast strains were cultivated in YPLac for 8 h after a preliminary culture in YPD. 40 µg of protein extract per yeast strain were loaded onto a 12% SDS-PAGE. The immunoblotting was carried out using anti-IBDV rabbit antiserum (1:10 000) and HRP-conjugated anti-rabbit antibodies from goat (1:10 000). Aggregated (agg.) and monomeric (mon.) IBDV-VP2 are indicated on the right by arrows, nonspecific bands by asterisks. B: Western blotting analysis for ascertaining the IBDV-VP2 content in lyophilized, heat-inactivated yeast material which was used afterwards in an immunization study in BALB/c mice (C). The yeast strains were cultivated in YPLac for 15 h after a preliminary preculture in YPD. For each yeast strain, 10 µg of protein extract were loaded onto a 12% SDS-PAGE, otherwise the immunoblotting was carried out as (A) above and the bands are indicated correspondingly. C: Testing of the immunogenicity of the two yeast strains VAK1127 and VAK1171 in the immunization experiment in BALB/c mice. Groups of five mice each were vaccinated three times subcutaneously using 0.1 mg (dry weight) of the above-analyzed (B) yeast material. The control used was a wild-type strain (VAK367) without antigen. The first administration was carried out using CFA (complete Freund's adjuvant) as adjuvant, and the further two, at two-week intervals, using IFA (incomplete Freund's adjuvant) as adjuvant. One week after the third administration, the mice were euthanized and bled. The sera were analyzed by IBDV-VP2 ELISA (IDEXX). The absorption at 650 nm, correlating with the anti-IBDV-VP2 antibody titer, is shown with standard error. A monoclonal anti-IBDV-VP2 antibody (pos. mab64) was used as positive control for the ELISA, and either sample buffer (neg. 1) or a nonspecific antibody (neg. 2) was used as negative control. What is shown is that both strains exhibit a similar level of foreign protein expression and exhibit immunogenic potential.

Figure 11:
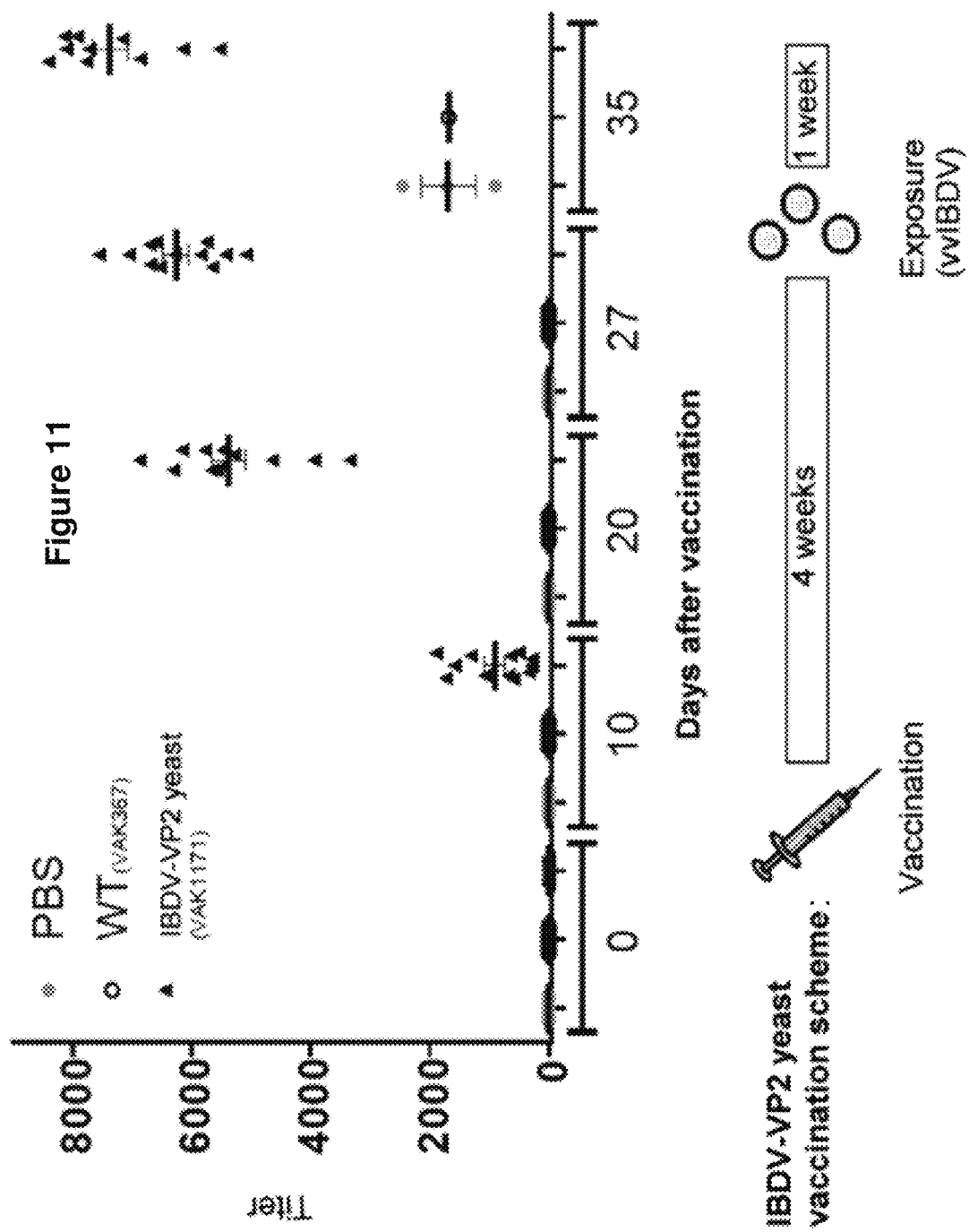

FIG. 11 shows, in combination with Table 3, the protective immunization of SPF chickens against vvIBDV by means of a single, subcutaneous administration with genetically optimized IBDV-VP2 vaccine yeast. Groups of at least 18 SPF chickens were vaccinated singly subcutaneously with 10 mg of heat-inactivated cells of the genetically optimized tandem IBDV-VP2 *K. lactis* yeast strain VAK1171 two weeks after hatching. The controls used were animals vaccinated with PBS or 10 mg of VAK367. They were vaccinated two times, two weeks and four weeks after hatching. All animals were challenged with vvIBDV six weeks after hatching. The sera were analyzed by ELISA (ProFLOK IBD Plus, Synbiotics) as described above. The antibody titers ascertained are shown. The individual points represent individual antibody titers of the twelve chickens analyzed per group, and the bar represents the mean value with standard deviation. In the case of the controls, only the antibody titer of the surviving chickens were ascertained after the challenge. What is shown is that just a 'one-shot' vaccination with the yeast subunit vaccine VAK 1171 achieves complete protection against a subsequent exposure to vvIBDV.

Figure 12:
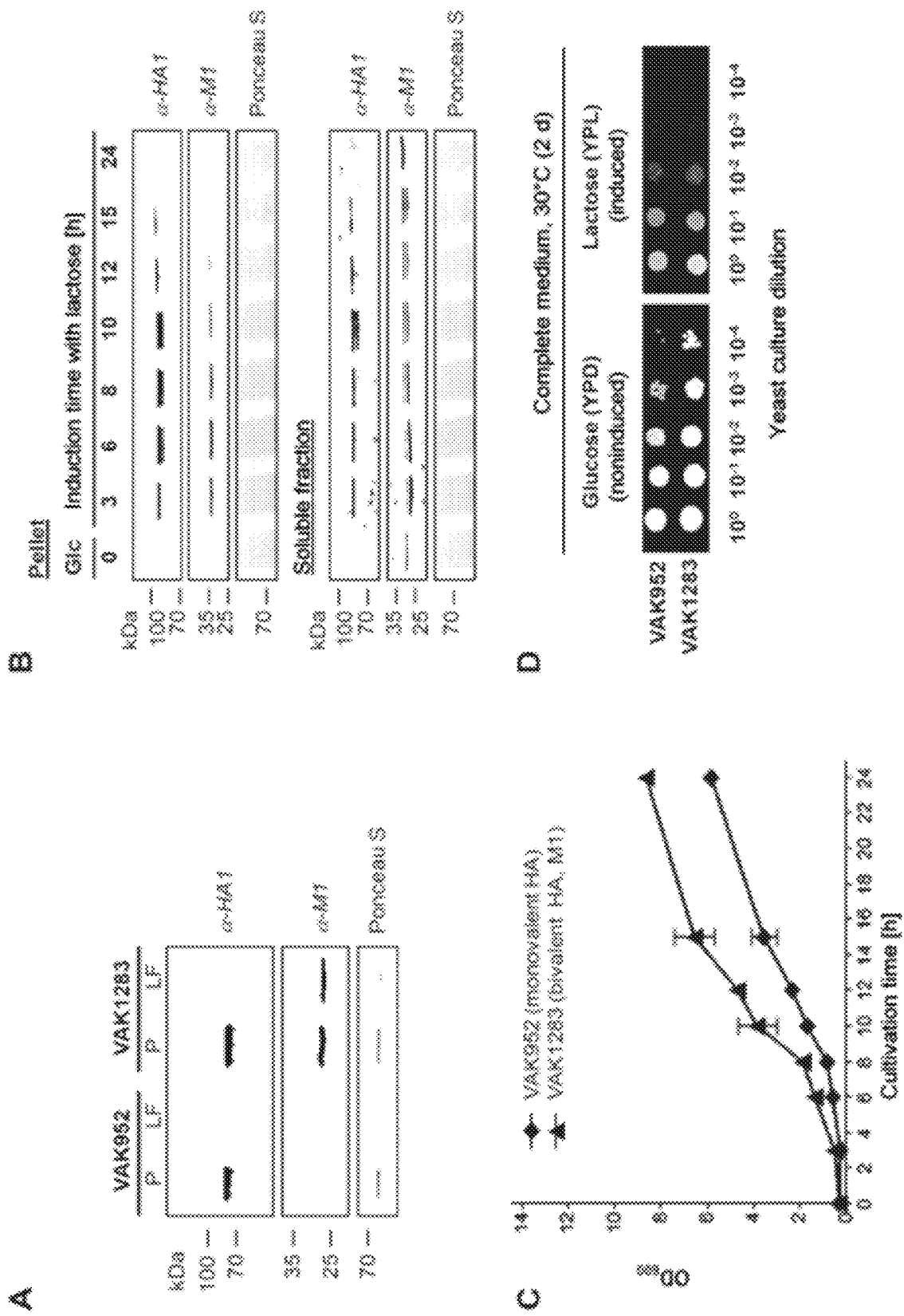

FIG. 12 shows the characterization of the strains VAK952 and VAK1283. (A) The yeast strains VAK952 (monovalent HA) and VAK1283 (bivalent HA, M1) were preincubated in a shake flask in YPD and subsequently induced in YPL for 6 h. The optical density at 600 nm was measured and 30 OD unit of the culture was harvested, the pellet was disrupted using glass beads, and the soluble protein fraction (LF) and the insoluble protein fraction (P, Pellet) were examined in an immunoblot. The primary antibody used was α-HA1 or α-M1 and the secondary antibody used was α-mouse-IRDye800CW. The signal was generated via an infrared imaging system (LI-COR Biosciences). (B, C) The yeast strains were preincubated in a shake flask in YPD and subsequently induced in YPL over a period of 24 h. At the specified time points, the optical density of the yeast culture was determined and 30 OD units were harvested. (B) The pellets of VAK1283 were disrupted using glass beads and analyzed in an immunoblot. (C) The values measured for the optical density of VAK952 and VAK1283 were combined as a growth curve as a function of time and averaged from at least two independent experiments. (D) For the dot test, the yeast strains were cultivated on YPD-containing nutrient agar plates at 30° C. for 48 h. Starting with 1 OD unit, the yeasts were serially diluted and subsequently dripped onto YPD-containing or YPL-containing nutrient agar plates. The plates were cultivated at 30° C. for 48 h and subsequently photographed. Ponceau S: staining of total yeast protein of the respective fraction, loading control. What is shown is that VAK952 (monovalent HA) and VAK1283 (bivalent HA, M1) express the HA protein in comparable quantities. Furthermore, what is shown is that VAK1283 and VAK952 have comparable growth properties, with VAK1283 having slight advantages.

Figure 13:
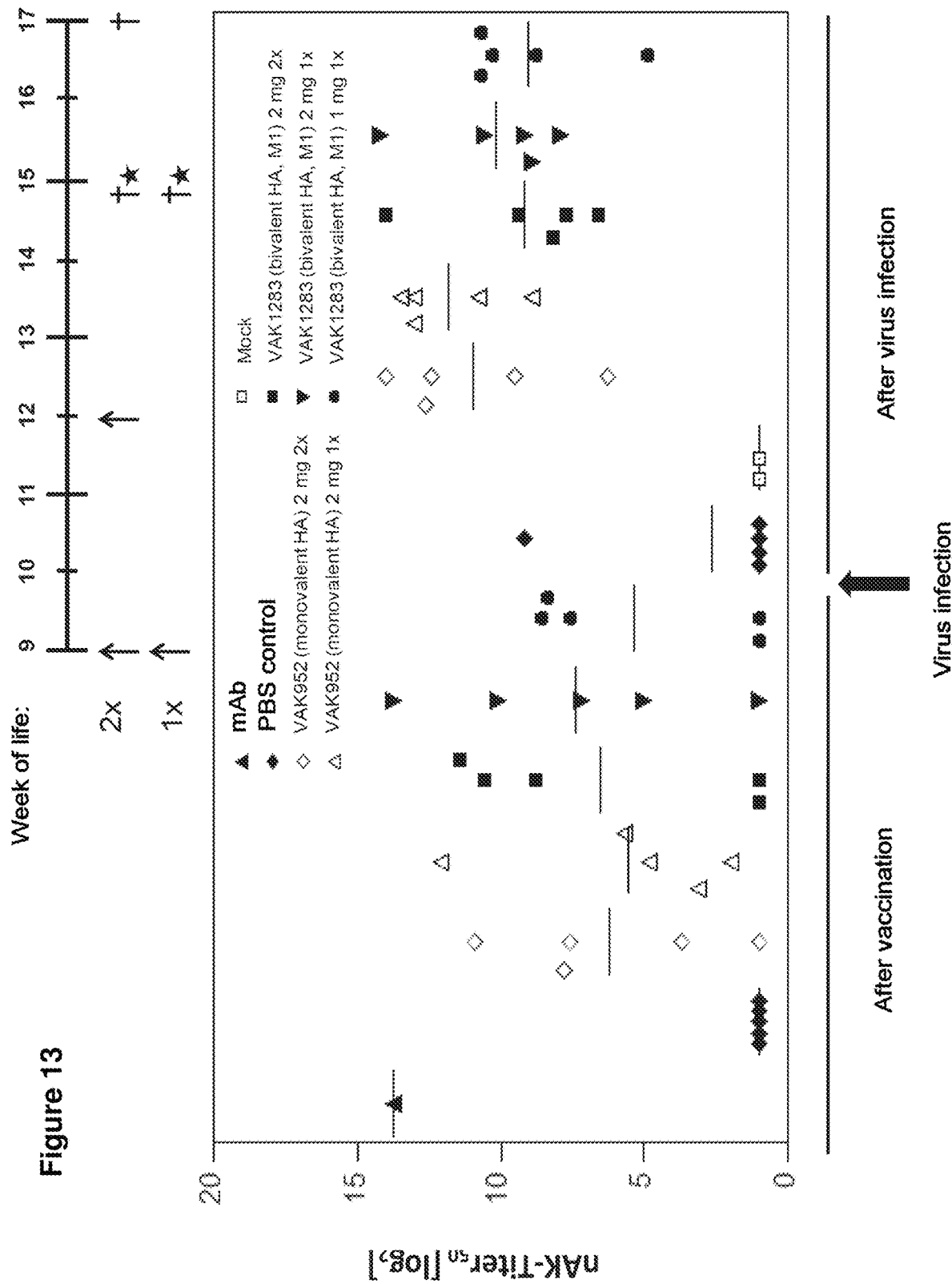

FIG. 13 illustrates the antibody titer in the serum of BALB/c mice after immunization with VAK952 (monovalent HA) and VAK1283 (bivalent HA, M1) before and after exposure infection. Both yeast strains were preincubated in a shake flask with YPD and subsequently induced in YPL for 12 h (VAK952) or 6 h (VAK1283). Thereafter, the cultures were harvested, freeze-dried and the yeast material was inactivated at 90° C. for 2 h. For the immunization, 9-week old, female BALB/c mice were vaccinated subcutaneously twice (prime-boost) or once (one shot) with 2 mg of yeast (VAK952, VAK1283) or with 1 mg of VAK1283 or twice with PBS (without adjuvant), at an interval of three weeks. The adjuvant used was AddaVax. Three or six weeks after the last administration, the animals were infected intranasally with 5×$MLD_{50}$ of the influenza A/PR/8/34 (H1N1) virus. The infection control used was mock-infected animals (Mock), to which only PBS without virus was administered intranasally. Three or six weeks after the last administration and during the exposure infection, the serum of the animals was obtained and tested for neutralizing antibodies (nAb) in a VNT. nAb $titer_{50}$: serum dilution which reduces the number of plaques by 50% in comparison with the virus-free control. The $log_2$ of the corresponding serum dilution is specified. Owing to the logarithmic plot, the value: $log_2(2)=1$ was assigned to serum samples without detectable antibodies. mAb: test system control (α-H1 (H37-66)). What is shown is that both immunization schemes lead to a significant induction of neutralizing Ab. Furthermore, it is clear that the neutralizing anti-HA antibody titers obtained in the case of the primer-boost vaccination experiments and one-shot vaccination experiments do not significantly differ for VAK952 and VAK1283.

Figure 14:
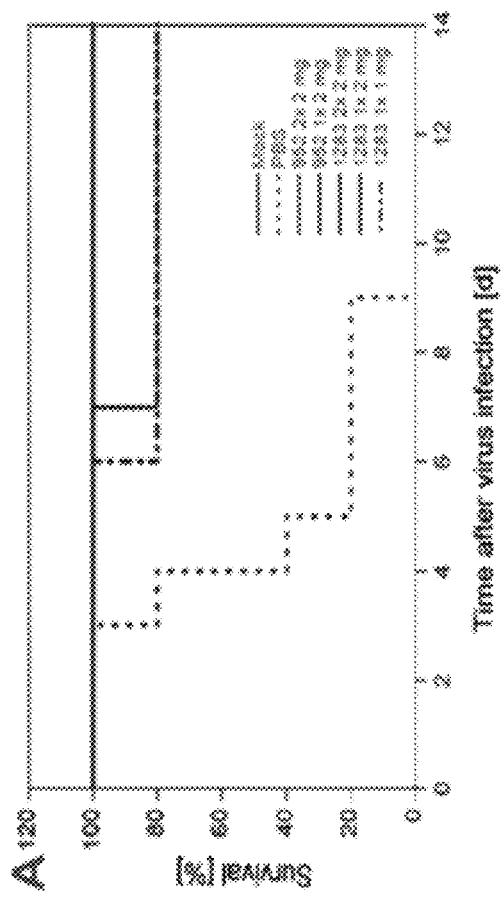
Figure 14:
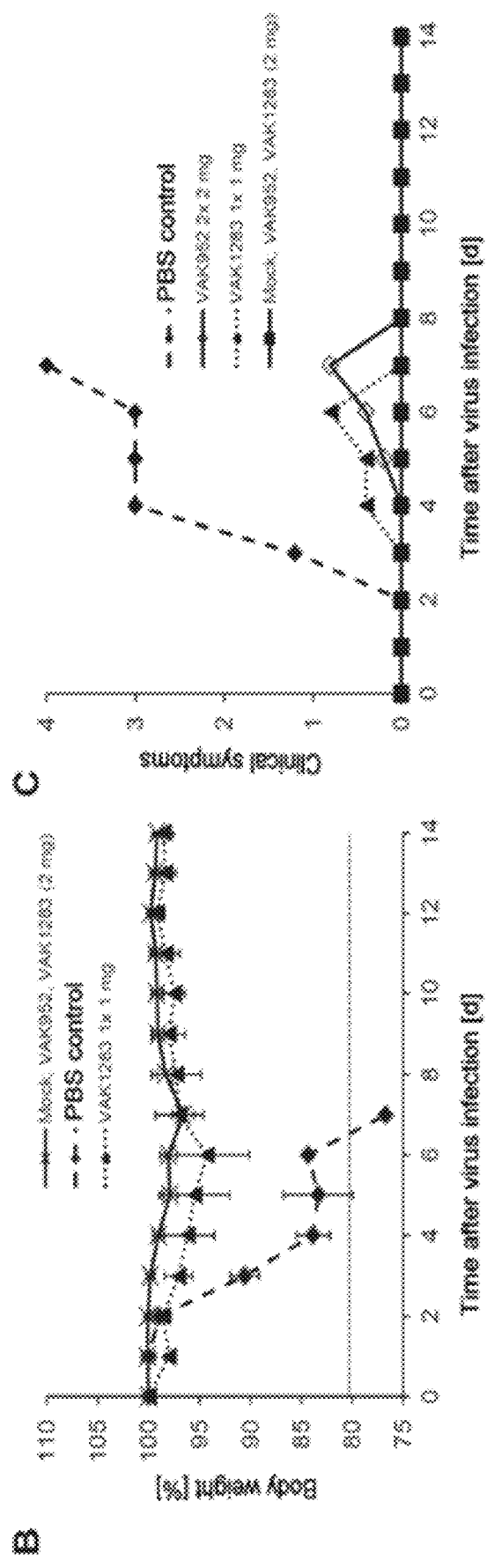

FIG. 14 shows the exposure infection with influenza A/PR/8/34 (H1N1) after immunization with VAK952 (monovalent HA) and VAK1283 (bivalent HA, M1). Three or six weeks after the last administration (see FIG. 13 for the immunization scheme), the BALB/c mice were infected intranasally with 5×$MLD_{50}$ of the influenza A/PR/8/34 (H1N1) virus. The infection control used was mock-infected animals (Mock), to which only PBS without virus was administered intranasally. Thereafter, the survival (A), the weight (B) and clinical symptoms (C) of the animals were examined multiple times every day over a period of 14 days. In the case of the clinical symptoms, a score of 0-4 was defined, which was averaged for each group (0: no anomalies; 1: slightly shaggy coat; 2: shaggy coat, reduced activity; 3: shaggy coat, 15% loss of body weight; 4: shaggy coat, >20% loss of body weight). What is shown is that the prime-boost immunization method with VAK952 does not provide optimal protection against a virus exposure, whereas this is the case for VAK1283. With both vaccines, the one-shot scheme generates optimal protection with 2 mg of administered vaccine. When 1 mg is administered, a similar protection rate is achieved with VAK1283 as with 2 mg of VAK952 in the prime-boost method.

EXEMPLARY EMBODIMENTS

Example 1: Generation of a Host Strain Having Two KIGAL4 Gene Copies, Stably Integrated, at Noncoupled Gene Loci A second KIGAL4 gene copy without a selection marker was inserted at a different gene locus (ectopically). It was possible to locate the insertion in the KIAVT3 gene (KLLA0E13795g) by sequencing (Klavt3::KIGAL4-1, SEQ ID No.: 1) (FIG. 1). The resultant strain is called VAK1111. The independent meiotic segregation of the two KIGAL4 copies, which are on chromosome E (ectopic copy) and D (genomic copy), was confirmed by a crossing experiment. Moreover, in the same experiment, the number of exactly two KIGAL4-1 gene copies in the genome was established.

To use VAK1111 for the targeted integration of an expression cassette at the LAC4 locus in analogy to VAK367-D4, the lac4::ScURA3 disruption was introduced, which makes it possible in one step, under selection for lactose growth, to integrate the desired foreign gene between LAC4 promoter and LAC4 reading frame by means of Klp vector technology without a marker (Krijger et al. (2012)). The resultant strain VAK1123 only differs from VAK367-D4 by the second, ectopic KIGAL4 gene copy.

Example 1.1: Improved Productivity of a Yeast Vaccine Strain Having an Additionally Integrated KIGAL4 Gene In one exemplary embodiment, the IBDV-o$VP2_{T2S}$ (Arnold et al. (2012)) gene was inserted into the LAC4 locus of the strain VAK1123 (resultant strain VAK1130). It was possible to establish an increased production of IBDV-VP2 compared to the otherwise isogenic strain having only one KIGAL4 copy (VAK910). As comparison, strain VAK1118, which bears only one KIGAL4 gene, but two CDS $VP2_{IBDV}$ copies (see below), is additionally shown (FIG. 2).

Example 2: $P_{LAC4-12LR2'}$ Promoter Having Reduced Basal Activity for Optimizing the Expression of Antigens Having a Cytopathic Effect Heterologous protein production in microorganisms is problematic when this leads to a cytopathic effect (CPE). Therefore, the task faced is to find a way to decouple the antigen production phase from the biomass accumulation phase. Owing to the inducible LAC4 promoter, this is partially possible by a fed-batch fermentation process, but is hampered because the promoter $P_{LAC4-12}$ is not completely closed down under noninducing conditions. In the case of antigens having a very strong CPE, what occurs is a reduction in the growth rate and an induction of the cellular stress response, with disadvantageous effects on antigen production. This problem is aggravated by the doubling of the KIGAL4 gene dose and/or the increase in the number of antigen-encoding sequences (see below). The solution was to delete the basal control region (BCR) of the promoter $P_{LAC4-12}$ (FIG. 3A) (Mehlgarten et al. (2015)) between −1065 and −1540 (LR2 deletion; $P_{LAC4-12}$-LR2'; SEQ ID No.: 2). Said deletion was introduced into the starting strains VAK367 (one KIGAL4 copy) and VAK1111 (two KIGAL4 copies) at the genomic LAC4 locus together with the lac4::ScURA3 disruption. The resultant strains VAK1109 and VAK1124 are suitable for the expression of antigens having CPE. The promoter $P_{LAC4-12}$LR2'was also inserted into the integrative vectors KlpURA3-Et and KlpMET5-Et (see below).

Example 2.1: Inhibition of the Basal (Noninduced) Expression of Antigen by a Modified Promoter After integration of a tandem IBDV-VP2 expression cassette into VAK1124 (resultant yeast strain: VAK1131; see below and FIG. 7 for an explanation of the term 'tandem expression cassette'), it was possible to show that the LR2 deletion in the LAC4-12 promoter leads to a strong reduction in VP2 protein production under noninducing conditions (FIG. 3B). With strains expressing the influenza A antigen hemagglutinin (VAK952 without LR2 deletion in the promoter, VAK1243 with LR2 deletion in the promoter), it was possible to show that the cytopathic effect of the influenza A HA antigen is suppressed and growth under noninducing conditions is improved as a result of the LR2 deletion (FIG. 3C).

Example 3: Versatile Vector System for the Targeted Integration of Multiple Expression Cassettes into the K. lactis Genome As before for VAK367-D4 (Krijger et al. (2012), WO 20101054649), the yeast strain VAK367 forms the genetic background of all *K. lactis* strains described here. This strain background has a need for uracil and methionine (uracil-and-methionine auxotrophy) owing to mutations in two genes, KlURA3 (KLLA0E22771g) and KlMET5 (KLLA0B03938g), which are referred to as alleles Klura3-20 (absent base pair at position +345) and Klmet5-1 (G2555A; and A3682T); the alleles are thus nonfunctional gene variants.

These mutated alleles were used in order to use further loci for targeted integration besides the integration site LAC4 already developed with the Klp3/Klp3-MCS (Krijger et al. (2012)) and to thereby generate multivalent vaccine strains (FIG. 4A). Selection is achieved by restoring the gene function of these mutated genes without additional insertion of a selection marker. To this end, new integration vectors were created. In said vectors, the expression cassettes (under the control of the LAC4-12 promoter or the variants thereof in each case) are flanked by gene segments which allow the upstream integration of the KlURA3 gene and downstream integration of the KlMET5 gene by homologous recombination and restore the wild-type sequences of these genes at the same time.

Further loci can be analogously developed as integration sites by mutagenesis and selection for auxotrophy for alternative growth substances.

Example 3.1: Vectors KlpURA3 and KlpMET5 for the Targeted Integration of Expression Cassettes (Having an Inducible LAC4-12 Promoter) at the KlURA3 (KLLA0E22771g) and/or KlMET5 (KLLA0B03938g) Loci of *K. lactis* Strains Having the Klura3-20 and/or Klmet5-1 Allele The integrative expression vectors KlpURA3 (SEQ ID No.: 3) and KlpMET5 (SEQ ID No.: 4) were constructed by means of suitable gene fragments (KlMET5/KlURA3 targeting sequences) which allow a targeted restoration of the functionality of the Klura3-20 and Klmet5-1 alleles, respectively.

The KlpMET5 expression vector contains the expression cassette consisting of the LAC4-12 promoter ($P_{LAC4-12}$ or the variants thereof), the encoding nucleic acid sequence of the antigen to be expressed and the AgTEF1 terminator; it is flanked upstream by the genomic KlMET5 fragment having an introduced ScCYC1 terminator and downstream by the KlAIM18 promoter having a downstream KlAI M18 gene. The KlpURA3 expression vector contains the expression cassette consisting of the LAC4-12 promoter ($P_{LAC4-12}$ or the variants thereof), the encoding nucleic acid sequence of the antigen to be expressed and the AgTEF1 terminator; it is flanked upstream by KLLA0E22749g having an associated promoter and downstream by the KlURA3 promoter having a downstream KlURA3 fragment (FIG. 4B, C).

In each case, the antigen-encoding sequence is cloned between promoter and terminator via AscI and NotI restriction sites. By Eco91I or KpnI restriction of the resultant plasmid, the entire expression cassette is separated from the KlpURA3 vector backbone, and by HindIII or BoxI restriction of the resultant plasmid, the entire expression cassette is separated from the KlpMET5 vector backbone, and the restriction material is transformed into *K. lactis* host strains having a Klura3-30 and/or Klmet5-1 allele. The foreign gene-containing expression cassette integrated in this way into KlURA3-20 or KlMET5-1 thus exactly corresponds to that which is also integrable into LAC4 in VAK367-D4 with the Klp3-MCS vector (WO 20101054649). Checking for uracil-prototrophic and/or methionine-prototrophic transformants is carried out in a standard manner via colony PCR using the primers MAB6 and VK211 for KlpMET5 transformants, and the primers MAB6 and VK71 for KlpURA3 transformants. Integration of the expression cassette at the correct target site between KlURA3 or KlMET5 and the respectively adjacent gene yields products of 1652 bp in size for KlpMET5 transformants and of 1307 bp in size for KlpURA3 transformants. No indications were obtained that the functionality of the neighboring genes is impaired by the insertion.

Primers:
  MAB6: 5'-CCCAGATGCGAAGTTAAGTG-3' (SEQ ID No.: 11)
  VK71: 5'-TACAACAGATCACGTGATCTTTTTGTAAG-3' (SEQ ID No.: 12)
  VK211: 5'-GATTTCGTAACCCTATTGTTCATGAATG-3' (SEQ ID No.: 13)

Example 3.2: Expression of a Foreign Antigen after Integration of the Encoding Gene Cassette at the KlURA3 or KlMET5 Locus A foreign gene under the control of the $P_{LAC4-12}$ promoter is induced approximately equally strongly by lactose after integration at the LAC4, KlURA3 and KlMET5 locus. The heat-labile, nontoxic, enterotoxin subunit B (Etx.B) from *E. coli* and an $(HA)_3$ epitope at the C-terminus (Etx.B-HA) was used as test protein for evaluating the vector system. The encoding sequence was cloned into the vectors KlpMET5, KlpURA3 and Klp3-MCS and integrated at the gene loci KlMET5 (VAK1251), KlURA3 (VAK1235) and LAC4 (VAK899) (FIG. 4D). As shown by western blotting, the concentration of the Etx.B-HA protein in all three strains is very similar (FIG. 4D). Therefore, it was not possible to establish any position effect, dependent on the integration site of the expression cassette in the genome, on the amount of recombinant protein production.

Example 3.3: Coexpression of Two Foreign Antigens in the Same Yeast Cell

The possibility of producing different heterologous proteins under the control of the $P_{LAC4-12}$ promoter in the same yeast strain via the new vector system was able to be shown by the construction of a yeast strain having an Etx.B-HA expression cassette at the KlURA3 locus and an expression cassette at the LAC4 locus having two VP2iBpv copies present as a tandem (VAK1234; FIG. 5; see below and FIG. 7 for an explanation of the tandem cassette). Compared to yeast strains in which only one of the expression cassettes was present in the genome in each case (VAK1235 or VAK1171), it was not possible to establish any reduction in the protein concentration of Etx.B-HA or VP2EDv in the case of VAK1234.

Example 4: LAC4 Promoter Variants for Modulating Recombinant Protein Synthesis Under Similar Induction Conditions The immunogenic effect of antigens is often based on the assembling of multiple proteins in a nonstoichiometric ratio. To make this possible in yeast-based vaccines, variants of the $P_{LAC4-12LR2'}$ promoter were generated (FIG. 6A) which can be differently induced by lactose or galactose. They are characterized by the number of binding sites for the activator KlGal4 (U1, U2, U4, U5; Gödecke et al. (1991)) and the presence/absence of the basal control region BCR. In addition to the constructs shown in FIG. 3A, which were inserted into the KlpURA3 vector, it was possible to generate promoter variants having increased promoter strength by insertion of further binding sites. The result of this is synthetic, lactose-inducible promoters for expanding the vector system and it is possible to realize different protein production or gene expression rates under the same induction conditions.

Example 4.1: Expression of a Foreign Antigen Under the Control of Various LAC4 Promoter Variants Expression of Etx.B-HA under the control of four LAC4-12 promoter variants. What were tested were four LAC4 promoter variants differing in the number of binding sites for the transcription activator KlGal4 and the presence/absence of a control region for basal expression under noninducing conditions (basal control region, BCR; FIG. 6A; SEQ ID No.: 14). Using said promoter variants, the KlpURA3-Et vector variants KlpURA3-PL412-Et, KlpURA3-PL412LR2-Et, KlpURA3-PL4-Et and KlpURA3-PL4LR2 were generated and the Etx.B-HA protein was inserted as test GOI in each case. As described above, the insertion of alternative GOIs is possible via the restriction sites AscI and NotI. The expression cassettes were integrated into the KlURA3 locus and the protein concentration of Etx.B-HA was quantified via western blotting (FIG. 6B). What is shown is that, under identical induction conditions (4 h in complete medium containing lactose), the longest promoter variant $P_{LAC4-12}$, which comprises the entire intergenic region between the LAC4 and LAC12 gene and contains four KlGal4-binding sites (U1, U2, U4, U5) (Gödecke et al. (1991)), leads to the highest protein concentration. If only the two U1 and U2 binding sites proximal to LAC4 are present (−1064 to −10), the additional deletion of the BCR (−1540 to −1065) also has a protein-reducing effect under inducing conditions.

Example 5: Raising of Antigen Production by Increasing the Copy Number of the Antigen-Encoding Gene The above-described vector system was therefore modified in order to rapidly and efficiently connect multiple gene copies in series and to introduce this expression cassette in one step at one of the three gene loci (FIG. 7A).

To produce a tandem expression cassette integrable at the LAC4 locus, three PCR-amplified fragments are fused by any desired Klp3(-MCS)-GOI template in one step (in-fusion cloning): (1 and 2) expression cassette containing $P_{LAC4-LR2}$ and $T_{TEF}$ (primers: VK30 & VK31, and VK32 & VK33) and (3) LAC4 targeting sequence (VK34 & VK35)). After restriction, for example using HpaI, the tandem expression cassette can be integrated into the lac4::URA3 locus as described (FIG. 7). After successful integration of the expression cassette, the first foreign gene copy is regulated by either $P_{LAC4-12}$ or $P_{LAC4-12-LR2}$ depending on the starting strain and the second is regulated by $P_{LAC4-LR2}$. Alternatively, insertion of a selection marker between the two expression cassettes into the restriction sites SmiI, MluI or PmeI and removal of the LAC4 targeting sequence via KpnI give rise to a tandem cassette which can be integrated into the genome in an undirected manner via NHEJ. If the expression cassette is cut out using MreI and AvaI, the compatible ends can be ligated and long, multiple expression cassettes can thereby be generated. By repeated restriction using MreI and AvaI, fragments in which the expression cassettes are arranged in tandem (head to tail) are enriched in the ligation mix. They are transformed and integrated in an undirected manner under selection for the marker.

Primers:
VK30: TATAGGGCGAATTGGAGCTCCGCCGGCG-GAAGAGGGTAACGCCTTTTGTTAAC-3' (SEQ ID No.: 15)
VK31: 5'-CTAAACGGAACTCGCATT-TAAATCTCGTTTTCGACACTGGATGG-3' (SEQ ID No.: 16)
VK32: 5'-GCGAGTTCCGTTTAGACGCGTT-TAAACTTGTTTAATTATTATGGGGCAGGCGAGA-3' (SEQ ID No.: 17)
VK33: 5'-CGGGGAATGCGCTGCTTTTCGACACTG-GATGGCGGCGTTA-3' (SEQ ID No.: 18)
VK34: 5'-GCAGCGCAT-TCCCCGGGTACCGCTCTCGACTAGGTGATT-AGCG-3' (SEQ ID No.: 19)
VK35: 5'-AAAAGCTGGGTACCGGGCC-CACTAGTCGAGAGTTAACCGTGACTACAGCTA-3' (SEQ ID No.: 20)

Example 5.1: Successful Use of the Multicopy Strategy

The strategy was confirmed using IBDV-VP2 as antigen and a Klp3-derived expression cassette containing two IBDV-VP2-encoding sequences (CDS-VP2/BEN) in tandem. The tandem IBDV-VP2 expression cassette (FIG. 7A) in the Klp3 vector (plasmid Klp3-tandem-oVP2$_{T2S}$, SEQ ID No.: 21) consists of two LAC4 promoter-regulated encoding sequences for VP2$_{IBDV}$ (CDS-VP2$_{IBDV}$) from Klp3-MCS-oVP2$_{T2S}$ (Arnold et al., (2012)). The promoter sequences consist of the region −1123 to −10 of the LAC4 promoter for the first copy, and −1099 to −10 for the second copy. Both CDS-VP2$_{IBDV}$ are flanked at the 3' end by an AgTEF1 terminator. The plasmid Klp3-tandem-oVP2$_{T2S}$ was cut using HpaI and the restriction material was transformed into strain VAK367-D4. The yeast strain VAK1118 thus generated contains the tandem expression cassette integrated at the LAC4 locus. As shown by western blotting, there is a higher IBDV-VP2 protein concentration in said strain compared to the isogenic strain having only one copy (FIG. 7B). The tandem expression cassette is genetically highly stable: after growth over 78 generations in inducing medium (YNB+Lactose), none of 100 colonies tested by PCR exhibited a genetic change to the expression cassette (data not shown).

Example 6: Tools for Producing Prototrophy in K. lactis Strains for Simplified Fermentation in Synthetic Medium and Complete Medium In studies carried out, it had become apparent that uracil-auxotrophic yeast strains grow more poorly in complete medium than uracil-prototrophic strains, an effect which could be neutralized only in part by the addition of uracil. To simplify the fermentation of the vaccines strains, to facilitate the establishment of the production processes and to make them more cost-efficient and to avoid growth effects due to insufficient uptake of methionine and/or uracil, what should therefore be found are ways of rapidly and reproducibly achieving the neutralization of these auxotrophies that are required for strain construction. For the reconstitution of KlURA3 from Klura3-20, a DNA fragment is generated via PCR with the aid of the primers VK67 and VK69 and the wild-type KlURA3 gene as template (FIG. 8A). To repair the Klmet5-1 allele, a PCR fragment is analogously generated with the aid of the primers VK74 and VK75 and the wild-type allele KlMET5 as template (FIG. 8B). Transformation of the PCR fragments into the corresponding mutated strains (individually or together) and selection on medium without methionine and/or without uracil led to reconstitution of the wild-type alleles with high efficiency. This process was carried out in order, inter alia, to generate the strains VAK1171 and VAK1400 (see above).

Primers

VK67: 5'-GACATCACTGTCTCTTCCCCTTAAT-GATC-3' (SEQ ID No.: 22)

VK69: 5'-TCAGCAAGCAT-CAATAATCCCCTTGGTTC-3' (SEQ ID No.: 23)

VK74: 5'-GAAAGAAAGACGTTGGTCTC-TACGCTTG-3' (SEQ ID No.: 24)

VK75: 5'-AGATTATAAGTTCCTGGGGCTTTACC-CAC-3' (SEQ ID No.: 25)

Example 7: Protective Immunization by Optimized, Inactivated Vaccine Yeasts

The modifications and optimizations of the *K. lactis* vaccine platform that were carried out as per Examples 1 to 5 were validated in various vaccination studies.

Example 7.1: Immunogenicity of an Optimized *K. lactis* Platform, Using the Example of an IBDV-VP2 Yeast Strain (VAK1127)

The VAK1127 strain contains a tandem IBDV-VP2 expression cassette (SEQ ID No.: 21), two KlGAL4 copies and the LR2 deletion in the LAC4 promoter. To characterize the immunogenicity of the yeast strain, immunization experiments were carried out in the target organism chicken. In challenge experiments, complete protection of SPF chickens against the very virulent (vv) IBDV strain 89163/7.3 (AFSSA, Ploufragan, France) that has been well characterized by Eterradossi and colleagues (1997) was achieved (Table 1 and 2). To this end, in the two experiments independently carried out, 1 mg of lyophilized, heat-inactivated (2 h, 90° C.) yeast (VAK1127) with incomplete Freund's adjuvant (IFA) was administered two times (FIG. 9A und B) subcutaneously (prime-boost). The administrations were carried out two weeks and four weeks after hatching, and the viral exposure (challenge) was effected six weeks after hatching. After 19 days, high titers of anti-IBDV-VP2 antibodies are already measurable in the case of the VAK1127-vaccinated animals. In the controls, titers of anti-IBDV-VP2 antibodies only occur after challenge with vvIBDV (FIG. 9). In both experiments, complete protection (0% morbidity, 0% mortality) of the VAK1127-vaccinated animals against the challenge with vvIBDV was observed (Table 1 und 2). With these experiments, it was possible to observe protection against vvIBDV using a subunit vaccine in a classic primer-boost vaccination method.

The immunogenicity of the vaccine yeasts is not influenced by the genetic back-mutation to antigen-bearing prototrophic yeast strains. It was possible to demonstrate this in a vaccination experiment in mouse with the aid of the auxotrophic form or prototrophic form of an IBDV-VP2 yeast strain (FIG. 10C). The yeast strain VAK1127 (auxotrophic) was, as described above (Example 6; FIG. 8), made prototrophic in two steps using PCR fragments for creating VAK1171. Both strain forms exhibit no significant difference in the expression level of recombinant protein (FIGS. 10A and B). The mice were vaccinated three times subcutaneously with 0.1 mg of heat-inactivated yeast subcutaneously with IFA at two-week intervals. It was not possible to establish any difference in the strength of seroconversion between the auxotrophic IBDV-VP2 strain (VAK1127) and the prototrophic descendant (VAK1171) (FIG. 10C).

Example 7.2: Complete Protection by Vaccination in a 'One-Shot' Scheme

A 'one-shot' vaccination, i.e., vaccination by a single administration of the vaccine, is normally not effective with subunit vaccines owing to lack of immunogenicity. However, the antibody titer-developing data obtained using the optimized strain VAK1127 in the prime/boost method (FIG. 9) indicate the possibility of obtaining protection even in a one-shot approach. This was checked by carrying out a one-shot vaccination with the prototrophic yeast strain VAK1171 (FIG. 11; Table 3). To this end, the yeast was administered only singly, in an elevated dose for this purpose (10 mg), and a challenge was then carried out at an interval of 4 weeks. It became apparent that, with VAK1171, complete protection against vvIBDV (0% morbidity, 0% mortality) can actually be achieved using 'one shot' (Table 3). This result could be attributed to the development of high, protective antibody titers, approx. 20 days after vaccination (FIG. 11). The fact that a one-shot vaccination scheme protects against vvIBDV with a high degree of protection shows the strong immunogenic potential of the vaccine used and provides impressive validation of the optimized vaccine platform.

Example 7.3: Improved Protection of a Bivalent Yeast Vaccine Compared to a Monovalent Yeast Vaccine when Used Against Influenza a Virus Infections To vaccinate against influenza virus type A, three different vaccines strains were generated. Firstly, VAK952 (DSM 32705) was generated, which expresses the major antigen of an influenza A strain (Puerto Rico/8/1934; PR8/34), the HA (hemagglutinin) gene. In VAK952, the gene is integrated into the genome into the LAC4 locus as described by Krijger et al. (2012) and Arnold et al. (2012). Secondly, VAK1283 (DSM 32697) was generated. Here, in addition to the HA gene from PR8/34 in the LAC4 locus, the M1 gene is additionally integrated into the URA3 locus. The M1 gene encodes a further important influenza A antigen which is distinctly more conserved than HA. Reports already published were able to show that combining both antigens can raise the immunogenicity of a vaccine against influenza A and also achieve a cross-protectivity against different influenza viruses. To also validate this aspect with a bivalent yeast vaccine, a further strain (VAK1395; DSM 32706) was generated, which likewise contains the M1 gene in the URA3 locus and where the HA gene from PR8/34 is replaced with the HA gene of the influenza virus California/4/2009. The comparable expression of HA and the additional expression of M1 of the respective strains was checked; it was also shown that the strains exhibit a comparable growth, with VAK1283 having slight advantages over VAK952 (FIG. 12). In vaccination studies in which a prime-boost scheme and one-shot scheme with different yeast concentrations in a mouse model were used in each case, it was shown that VAK952 and VAK1283 each induce comparable titers of virus-neutralizing antibodies (FIG. 13). However, in the challenge experiment, it then became clear that the bivalent VAK1283 vaccine allows maximum protection both in the prime-boost schema and in the one-shot schema, whereas this is not the case with the monovalent VAK952 vaccine. Moreover, with the vaccine VAK1283 in the one-shot experiment at half of the yeast material used, a similar protective effect was achieved as with VAK952 in the prime-boost approach (FIG. 14 and Table 3). In experiments in which VAK1395 was used as vaccine, it was also possible to establish protection against influenza PR8/34. Cross-protection against different influenza variants was thus achieved using a bivalent yeast vaccine.

(b) The histopathological bursal lesion assessment was carried out using a scale of 0-4: 0: no lesions; 1: 5-25% of follicles affected; 2: 26-50% of follicles affected; 3: 51-75% of follicles affected; 76-100% bursal damage (loss of structure).

(c) The mean value of the bursa-to-body weight index (bu/bod) was calculated using the formula: (bursa weight/body weight)*1000. The nonexposed control group consisted of at least seven chickens, the exposed group ten. The standard deviation is given.

TABLE 1

Indications for exposure protection in vaccinated SPF chickens

| Vaccination (a) | | | Histopathological bursal lesion assessment | | | | | bu/bod index (c) | | Morbidity | Mortality |
|---|---|---|---|---|---|---|---|---|---|---|---|
| Yeast strain (VAK) | VP2 amount per vaccine dose | Adjuvant | 0 | 1 | 2 | 3 | 4 | Exposed | Unexposed | (%) (d) | (%) (e) |
| 367 | none | IFA | — | — | — | 1 | 7 | 2.80 ± 1.32 | 5.36 ± 0.65 | 6/10 (60) | 4/10 (40) |
| 1127 | 4.1 ± 0.25 µg | IFA | 8 | — | — | 1 | — | 4.40 ± 0.76 | 4.89 ± 0.63 | 0/10 | 0/10 |
| — | PBS | IFA | — | — | — | — | 10 | 4.08 ± 1.91 | 4.92 ± 0.94 | 10/10 (100) | 8/10 (80) |

TABLE 2

Indications for exposure protection in vaccinated SPF chickens

| Vaccination (a) | | | Histopathological bursal lesion assessment | | | | | bu/bod index (c) | | Morbidity | Mortality |
|---|---|---|---|---|---|---|---|---|---|---|---|
| Yeast strain (VAK) | VP2 amount per vaccine dose | Adjuvant | 0 | 1 | 2 | 3 | 4 | Exposed | Unexposed | (%) (d) | (%) (e) |
| 1127 | 4.1 ± 0.71 µg | IFA | 6 | — | — | — | — | 5.10 ± 0.78 | 4.81 ± 1.20 | 0/9 (0) | 0/9 (0) |
| — | PBS | IFA | — | — | — | — | 8 | 4.09 ± 1.87 | 5.32 ± 0.85 | 9/9 (100) | 7/9 (78) |

TABLE 3

Indications for exposure protection in vaccinated SPF chickens

| Vaccination (a) | | | Histopathological bursal lesion assessment | | | | | bu/bod index (c) | | Morbidity | Mortality |
|---|---|---|---|---|---|---|---|---|---|---|---|
| Yeast strain (VAK) | VP2 amount per vaccine dose | Adjuvant | 0 | 1 | 2 | 3 | 4 | Exposed | Unexposed | (%) (d) | (%) (e) |
| PBS | none | MF59 | — | — | — | — | 9 | 3.73 ± 1.92 | 4.77 ± 1.02 | 9/9 (100) | 6/9 (66) |
| VAK367 | none | MF59 | — | — | — | — | 10 | 4.09 ± 1.58 | 3.60 ± 0.89 | 10/10 (100) | 9/10 (90) |
| VAK1171 | 35 ± 4.2 µg | IFA | 10 | — | — | — | — | 4.48 ± 0.37 | 3.96 ± 1.02 | 0/10 (0) | 0/10 (0) |

Explanatory Notes for Table 1

(a) The chickens were vaccinated subcutaneously with 1 mg of yeast (or PBS) and IFA as adjuvant two weeks after hatching. Two weeks after vaccination, they were boosted in the same manner. Another two weeks later, the viral exposure test was carried out via the oculo-nasal route with $10^4$ EID vvIBDV (very virulent 89163/7.3). Inactivated, whole yeast of the strain VAK1127 was used as vaccine yeast, and a group which was only vaccinated with PBS and IFA was used as the infection control. A group in which wild-type yeast without antigen (VAK367) was administered acted as the control for the yeast effect alone.

(d) Morbidity is represented as the number of morbid chickens per number of chickens in the group overall. The percentage of morbid chickens is shown between parentheses.

(e) Mortality is represented as the number of dead chickens per number of chickens in the group overall. The percentage of dead chickens is shown between parentheses.

Explanatory Notes for Table 2

(a) The chickens were vaccinated subcutaneously with 1 mg of yeast (or PBS) and IFA as adjuvant two weeks after hatching. Two weeks after vaccination, they were boosted in the same manner. Another two weeks later, the viral exposure test was carried out via the oculonasal route with 10 4 EID vvIBDV (very virulent 89163/7.3). Inactivated, whole yeast of the strain VAK1127 was used as vaccine yeast, and a group which was only vaccinated with PBS and IFA was used as the infection control.

(b) The histopathological bursal lesion assessment was carried out using a scale of 0-4: 0: no lesions; 1: 5-25% of follicles affected; 2: 26-50% of follicles affected; 3: 51-75% of follicles affected; 76-100% bursal damage (loss of structure).

(c) The mean value of the bursa-to-body weight index (bu/bod) was calculated using the formula: (bursa weight/body weight)*1000. The nonexposed control group consisted of at least five chickens, the exposed group nine. The standard deviation is given.

(d) Morbidity is represented as the number of morbid chickens per number of chickens in the group overall. The percentage of morbid chickens is shown between parentheses.

(e) Mortality is represented as the number of dead chickens per number of chickens in the group overall. The percentage of dead chickens is shown between parentheses.

Explanatory Notes for Table 3

(a) The chickens were vaccinated subcutaneously with 10 mg of yeast (or PBS) and IFA as adjuvant two weeks after hatching. Four weeks later, the viral exposure test was carried out via the oculonasal route with 10 4 EID vvIBDV (very virulent 89163/7.3). Inactivated, whole yeast of the strain VAK1171 was used singly yeast vaccine. The infection control used was, firstly, a group vaccinated only with PBS and MF59 and, secondly, a group vaccinated with wild-type yeast and MF59; two weeks after the first vaccination, both were administered a boost containing the same amount of yeast or PBS.

(b) The histopathological bursal lesion assessment was carried out using a scale of 0-4: 0: no lesions; 1: 5-25% of follicles affected; 2: 26-50% of follicles affected; 3: 51-75% of follicles affected; 76-100% bursal damage (loss of structure).

(c) The mean value of the bursa-to-body weight index (bu/bod) was calculated using the formula: (bursa weight/body weight)*1000. Each group consisted of at least nine chickens. The standard deviation is given.

(d) Morbidity is represented as the number of morbid chickens per number of chickens in the group overall. The percentage of morbid chickens is shown between parentheses.

(e) Mortality is represented as the number of dead chickens per number of chickens in the group overall. The percentage of dead chickens is shown between parentheses.

Sequences

The patent application contains the following sequences as part of the description:

| SEQ ID. No. | Designation |
|---|---|
| 1 | *K. lactis* avt3::LAC9 |
| 2 | $P_{LAC4-12-LR2}$ |
| 3 | KlpURA3 vector |
| 4 | KlpMET5 vector |
| 5 | LAC4-12 promoter variant PLAC4-12 |
| 6 | LAC4-12 promoter variant $P_{LAC4-12-LR2}$ |
| 7 | LAC4-12 promoter variant $P_{LAC4}$ |
| 8 | LAC4-12 promoter variant $P_{LAC4-LR2}$ |
| 9 | Primer sequence VK183 |
| 10 | Primer sequence VK184 |
| 11 | Primer sequence MAB6 |
| 12 | Primer sequence VK71 |
| 13 | Primer sequence VK211 |
| 14 | BCR from $P_{LAC4-12}$ |
| 15 | Primer sequence VK30 |
| 16 | Primer sequence VK31 |
| 17 | Primer sequence VK32 |
| 18 | Primer sequence VK33 |
| 19 | Primer sequence VK34 |
| 20 | Primer sequence VK35 |
| 21 | Klp3-tandem-oVP2T2S |
| 22 | Primer sequence VK67 |
| 23 | Primer sequence VK69 |
| 24 | Primer sequence VK74 |
| 25 | Primer sequence VK75 |

REFERENCES

Arnold, M.; Durairaj, V.; Mundt, E.; Schulze, K.; Breunig, K. D. & Behrens, S.-E. Protective Vaccination against Infectious Bursal Disease Virus with Whole Recombinant *Kluyveromyces lactis* Yeast Expressing the Viral VP2 Subunit, *PLoS ONE, Public Library of Science*, 2012, 7, e42870

Berthoud, T. K.; Hamill, M.; Lillie, P. J.; Hwenda, L.; Collins, K. A.; Ewer, K. J.; Milicic, A.; Poyntz, H. C.; Lambe, T. & Fletcher, H. A. Potent CD8+ T-cell immunogenicity in humans of a novel heterosubtypic influenza A vaccine, MVA— NP+M1, *Clinical infectious diseases, Oxford University Press*, 2011, 52, 1-7

Bathurst, I. C. Protein expression in yeast as an approach to production of recombinant malaria antigens, *The American journal of tropical medicine and hygiene, ASTMH*, 1994, 50, Breunig, K. D. Multicopy plasmids containing the gene for the transcriptional activator LAC9 are not tolerated by *K. lactis* cells, *Current genetics, Springer*, 1989, 15, 143-148 de Silva; Chandimal, U.; Tanaka, H.; Nakamura, S.; Goto, N. & Yasunaga, T. A comprehensive analysis of reassortment in influenza A virus, *Biology open, The Company of Biologists Ltd*, 2012, 1, 385-390

Eterradossi, N.; Toquin, D.; Abbassi, H.; Rivallan, G.; Cotte, J. & Guittet, M. Passive Protection of Specific Pathogen Free Chicks Against Infectious Bursal Disease by In-Ovo Injection of Semi-Purified Egg-Yolk Antiviral Immunoglobulins, *Zoonoses and Public Health, Wiley Online Library*, 1997, 44, 371-383

Gellissen, G. & Hollenberg, C. P. Application of yeasts in gene expression studies: a comparison of *Saccharomyces cerevisiae*, *Hansenula polymorpha* and *Kluyveromyces lactis*-a review, *Gene, Elsevier*, 1997, 190, 87-97

Gödecke, A.; Zachariae, W.; Arvanitidis, A. & Breunig, K. D. Coregulation of the *Kluyveromyces lactis* lactose permease and β-galactoidase genes is achieved by interaction of multiple LAC9 binding sites in a 2.6 kbp divergnent promoter, *Nucleic acids research, Oxford University Press*, 1991, 19, 5351-5358

Granzow, H.; Birghan, C.; Mettenleiter, T. C.; Beyer, J.; Kanner, B. & Mundt, E. A second form of infectious bursal disease virus-associated tubule contains VP4., *Journal of virology, Am Soc Microbiol,* 1997, 71, 8879-8885

Kasanga, C. J.; Yamaguchi, T.; Wambura, P. N.; Maeda-Machang'u, A. D.; Ohya, K. & Fukushi, H. Molecular characterization of infectious bursal disease virus (IBDV): diversity of very virulent IBDV in Tanzania, *Archives of virology, Springer,* 2007, 152, 783-790

Kirchenbaum, G. A. & Ross, T. M. Eliciting broadly protective antibody responses against influenza, *Current opinion in immunology, Elsevier,* 2014, 28, 71-76

Kirunda, H.; Erima, B.; Tumushabe, A.; Kiconco, J.; Tugume, T.; Mulei, S.; Mimbe, D.; Mworozi, E.; Bwogi, J. & Luswa, L. Prevalence of influenza A viruses in livestock and free-living waterfowl in Uganda, *BMC veterinary research, BioMed Central,* 2014, 10, 50

Krammer, F. & Palese, P. Influenza virus hemagglutinin stalk-based antibodies and vaccines, *Current opinion in virology, Elsevier,* 2013, 3, 521-530

Krijger, J.-J.; Baumann, J.; Wagner, M.; Schulze, K.; Reinsch, C.; Klose, T.; Onuma, O. F.; Simon, C.; Behrens, S.-E. & Breunig, K. D. A novel, lactase-based selection and strain improvement strategy for recombinant protein expression in Kluyveromyces lactis, *Microbial Cell Factories,* 2012, 11, 112

Kumar, K.; Singh, K. C. P. & Prasad, C. B. Immune responses to intermediate strain IBD vaccine at different levels of maternal antibody in broiler chickens, *Tropical animal health and production, Springer,* 2000, 32, 357-360

Negash, T.; Gelaye, E.; Petersen, H.; Grummer, B. & Rautenschlein, S. Molecular evidence of very virulent infectious bursal disease viruses in chickens in Ethiopia, *Avian diseases, BioOne,* 2012, 56, 605-610

Rautenschlein, S.; Kraemer, C. H.; Vanmarcke, J. & Montiel, E. Protective efficacy of intermediate and intermediate plus infectious bursal disease virus (IBDV) vaccines against very virulent IBDV in commercial broilers, *Avian diseases, BioOne,* 2005, 49, 231-237

Remington's Practice of Pharmacy, 13th edition and J. of Pharmaceutical Science & Technology, Vol. 52, No. 5, September-October, pages 238-311

Ridpath, J. F. Emerging pestiviruses infecting domestic and wildlife hosts, *Animal Health Research Reviews, Cambridge University Press,* 2015, 16, 55-59

RKI, *Influenza (Teil 2): Erkrankungen durch zoonotische Influenzaviren* [Influenza (part 2): diseases due to zoonotic influenza viruses], 2016 Schrauwen, E. J. A. & Fouchier, R. A. M. Host adaptation and transmission of influenza A viruses in mammals, *Emerging microbes & infections, Nature Publishing Group,* 2014, 3, e9

Short, K. R.; Richard, M.; Verhagen, J. H.; van Riel, D.; Schrauwen, E. J. A.; van den Brand, J. M. A.; Manz, B.; Bodewes, R. & Herfst, S. One health, multiple challenges: The inter-species transmission of influenza A virus, *One health, Elsevier,* 2015, 1,1-13

Steel, J.; Lowen, A. C.; Wang, T. T.; Yondola, M.; Gao, Q.; Haye, K.; García-Sastre, A. & Palese, P. Influenza virus vaccine based on the conserved hemagglutinin stalk domain, *MBio, Am Soc Microbiol,* 2010, 1, e00018-10

WHO, Influenza (Seasonal), 2016

WHO, Biologicals, Influenza, 2017

The invention claimed is:

1. A *Kluyveromyces lactis* (*K. lactis*) strain for targeted cloning of foreign antigen-encoding nucleic acids into the yeast genome of the *K. lactis* strain, characterized in that the *K. lactis* strain has integrated expression cassettes for foreign antigens at:

i) the KlURA3-20 locus;
   ii) the KlMET5-1 locus;
   iii) the KlURA3-20 locus and the KlMET5-1 locus;
   iv) the KlURA3-20 locus and the KlLAC4 locus;
   v) the KlMET5-1 locus and the KlLAC4 locus; or
   vi) the KlURA3-20 locus, the KlMET5-1 locus, and the KlLAC4 locus.

2. The *K. lactis* strain as claimed in claim 1, characterized in that the expression cassettes contain the *K. lactis* LAC4-12 promoter or variants of said promoter, including the intergenic region between LAC12 and LAC4, the antigen-encoding region and the AgTEF1 terminator.

3. The *K. lactis* strain as claimed in claim 1, characterized in that multiple copies of a foreign antigen-encoding nucleic acid are inserted via tandem expression cassettes or multi-expression cassettes at the KlLAC4 locus or at the KlURA3-locus or at the KlMET5-1 locus of the resultant *K. lactis* strains.

4. The *K. lactis* strain as claimed in claim 1, characterized in that the gene of the foreign antigen IBDV VP2 is present in the form of a tandem expression cassette at the locus KlLAC4 of the *K. lactis* strain.

5. The *K. lactis* strain as claimed in claim 1, characterized in that one or more copies of different foreign antigen-encoding nucleic acids are inserted via single expression cassettes, tandem expression cassettes or multi-expression cassettes at the KlLAC4 locus and/or at the KlURA3-20 locus and/or at the KlMET5-1 locus.

6. The *K. lactis* strain as claimed in claim 1, characterized in that the encoding genes of the foreign antigens influenza A HA and influenza A M1 are inserted at the KlLAC4 and KlURA3-20 loci of the *K. lactis* strain and are expressed.

7. The *K. lactis* strain as claimed in claim 1, characterized in that the *K. lactis* strain contains, in addition to the genomic KlGAL4 gene, additionally a second ectopic copy of the KlGAL4 gene.

8. The *K. lactis* strain as claimed in claim 7, characterized in that the ectopic copy of the KlGAL4 gene, which is flanked by the KlGAL4 promoter and KlGAL4 terminator, is integrated in the *K. lactis* strain at the gene locus KLLA0E13795g (SEQ ID NO: 1).

9. The *K. lactis* strain as claimed in claim 1, the *K. lactis* strain having a modified promoter structure of the LAC4-12 promoter that allows reduced or no foreign protein expression under noninduced conditions, characterized in that the basal control region (BCR) of the promoter PLAC4-12-LR2 between −1065 and −1540 (SEQ ID NO: 2) is deleted.

10. The *K. lactis* strain as claimed in claim 9, characterized in that the gene of the foreign antigen influenza A HA is present at the locus KlLAC4 of the *K. lactis* strain.

11. The *K. lactis* strain as claimed in claim 1, the *K. lactis* strain having a modified promoter structure of the LAC4-12 promoter that allows modulation of foreign protein expression, characterized in that the number of binding sites for the activator KlGal4 of the promoter varies and 1, 2, 3 or 4 KlGal4-binding sites are present.

12. The *K. lactis* strain as claimed in claim 1, characterized in that the gene of the foreign antigen IBDV VP2 is inserted at the locus KlLAC4 of the *K. lactis* strain.

13. The *K. lactis* strain as claimed in claim 1, characterized in that the gene function of the alleles Kllac4, Klura3-20 and Klmet5-1 is restored and the *K. lactis* strain is prototrophic.

14. The *K. lactis* strain as claimed in claim 1, characterized in that the genes of the foreign antigens BVDV E2 ectodomain, BVDV E2 ectodomain, and BVDV Npro-NS3 are inserted at the loci KlLAC4, KlURA3-20 and KlMet5-1 of the *K. lactis* strain.

15. A *K. lactis* strain according to claim 1, wherein said *K. lactis* strain is selected from the group consisting of:
   VAK952 DSM 32705;
   VAK1111 DSM 32696;
   VAK1118 DSM 32701;
   VAK1131 DSM 32700;
   YAK 1171 DSM 32699;
   VAK1243 DSM 32702;
   VAK1283 DSM 32697;
   VAK1395 DSM 32706 and
   VAK1400 DSM 32698.

16. An integrative expression vector selected from the group consisting of KlpURA3, KlpMET5, KlpMET5-PL4-12-Et, KlpMET5-PL4-12-LR2-Et, KlpMET5-PL4-Et, Klp- MET5-PL4-LR2-Et, KIpURA3-PL4-12-Et, KIpURA3-PL4-12-LR2-Et, KIpURA3-PL4-Et and KIpURA3-PL4-LR2-Et.

17. A pharmaceutical composition containing a *K. lactis* strain as claimed in claim 1.

* * * * *